United States Patent
Guelcher et al.

(10) Patent No.: US 10,046,086 B2
(45) Date of Patent: Aug. 14, 2018

(54) POLY(THIOKETAL-URETHANE) SCAFFOLDS AND METHODS OF USE

(71) Applicant: Vanderbilt University, Nashville, TN (US)

(72) Inventors: Scott A. Guelcher, Thompsons Station, TN (US); Madison McGough, Nashville, TN (US); Mukesh K. Gupta, Nashville, TN (US); Craig L. Duvall, Nashville, TN (US); John Martin, Nashville, TN (US); Jon Page, Mount Juliet, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/290,875

(22) Filed: Oct. 11, 2016

(65) Prior Publication Data

US 2017/0119924 A1    May 4, 2017

Related U.S. Application Data

(63) Continuation-in-part of application No. 14/430,130, filed as application No. PCT/US2013/061064 on Sep. 21, 2013, now Pat. No. 9,463,261.
(Continued)

(51) Int. Cl.
*A61L 27/18* (2006.01)
*A61L 27/58* (2006.01)
(Continued)

(52) U.S. Cl.
CPC ............. *A61L 27/18* (2013.01); *A61L 27/425* (2013.01); *A61L 27/54* (2013.01); *A61L 27/58* (2013.01);
(Continued)

(58) Field of Classification Search
CPC ........ A61K 8/23; A61K 31/185; A61K 47/20; C07C 323/12; C08G 18/3868; C08G 2230/00
See application file for complete search history.

(56) References Cited

U.S. PATENT DOCUMENTS 5,079,271 A    1/1992  Gillis
5,556,982 A *  9/1996  Fritzberg ......... A61K 47/48746
                                                     530/391.5
(Continued)

FOREIGN PATENT DOCUMENTS

WO    WO2009/140427    5/2009
WO    WO2009/140421    11/2009
(Continued)

OTHER PUBLICATIONS

Shim et al. (Angew Chem Int Ed 2013;52:6926-6929).*
(Continued)

*Primary Examiner* — Ernst V Arnold
(74) *Attorney, Agent, or Firm* — Stites & Harbison PLLC; Sean P. Ritchie

(57) ABSTRACT

A biodegradable scaffold, a low-molecular weight thioketal, and a method of forming a biodegradable scaffold are provided. The biodegradable scaffold includes a thioketal and an isocyanate, where the thioketal is linked to the isocyanate to form the scaffold. The low-molecular weight thioketal includes 2,2-dimethoxypropane and thioglycolic acid, wherein the thioketal includes at least two hydroxyl terminal groups. The method of forming the biodegradable scaffold includes blending a thioketal with an excess isocyanate, forming a quasi-prepolymer, mixing the thioketal, the quasi-prepolymer, and a ceramic, and then adding a
(Continued)

catalyst to form the biodegradable scaffold. The thioketal is a low-molecular weight thioketal having at least two hydroxyl terminal groups.

17 Claims, 17 Drawing Sheets

Related U.S. Application Data

(60) Provisional application No. 62/242,226, filed on Oct. 15, 2015, provisional application No. 61/704,351, filed on Sep. 21, 2012.

(51) Int. Cl.
| | |
|---|---|
| A61L 27/54 | (2006.01) |
| C07C 323/12 | (2006.01) |
| C08G 18/77 | (2006.01) |
| C08G 18/38 | (2006.01) |
| C08G 18/10 | (2006.01) |
| C08G 18/20 | (2006.01) |
| A61L 27/42 | (2006.01) |

(52) U.S. Cl.
CPC ............ *C07C 323/12* (2013.01); *C08G 18/10* (2013.01); *C08G 18/2063* (2013.01); *C08G 18/3868* (2013.01); *C08G 18/771* (2013.01); *A61L 2400/06* (2013.01); *A61L 2430/02* (2013.01); *C08G 2230/00* (2013.01)

(56) References Cited

U.S. PATENT DOCUMENTS

| | | |
|---|---|---|
| 8,252,846 B2 | 8/2012 | Murthy et al. |
| 2008/0028019 A1 | 1/2008 | Philyaw et al. |
| 2009/0093565 A1 | 4/2009 | Yang et al. |
| 2012/0070383 A1 | 3/2012 | Almutairi et al. |
| 2015/0231302 A1 | 8/2015 | Duvall et al. |

FOREIGN PATENT DOCUMENTS

| | | |
|---|---|---|
| WO | WO2009/140423 | 11/2009 |
| WO | WO2009/140429 | 11/2009 |
| WO | WO2010/053596 | 5/2010 |
| WO | WO2014/047524 | 3/2014 |
| WO | WO2014/066912 | 5/2014 |

OTHER PUBLICATIONS

Liu et al. (Adv Funct Mater. (Jul. 1, 2016);26:6257-6269).*
Catalysts for polyurethane foam Evonik Industries [online] retrieved on Mar. 28, 2018 from: https://www.pu-additives.com/product/pu-additives/Documents/PU-SG-Catalysts-EN.pdf; 6 pages. (Year: 2018).*
Eglin, et al.; Thiol-Containing Degradable Poly(thiourethane-urethane)s for Tissue Engineering; Journal of Biomaterials Science 21 (2010) 477-491.
Wilson, et al; Orally delivered thioketal nanoparticles loaded with TNF-a-siRNA target inflammation and inhibit gene expression in intestines; Nature Materials; 2010; vol. 9; pp. 923-928.
Pu, et al., Nanoparticles with Dual Responses to Oxidative Stress and Reduced pH for Drug Release and Anti-Inflammatory Applications; Acsnano; 2014; vol. 8; No. 2; pp. 1213-1221.
Shim, et al.; A Reactive Oxygen Species (ROS)-Responsive Polymer for Safe, Efficient, and Targeted Gene Delivery in Cancer Cells; Angew. Chem. Int. Ed. 2013, 52, 6926-6929.
Aste-Amezaga M, Ma X, Sartori A, Trinchieri G. Molecular mechanisms of the induction of il-12 and its inhibition by il-10. The Journal of Immunology. 1998;160:5936-5944.
Christenson EM, Anderson JM, Hiltner A. Oxidative mechanisms of poly(carbonate urethane) and poly(ether urethane) biodegradation: In vivo and in vitro correlations. Journal of Biomedical Materials Research Part A. 2004;70A:245-255.
de Gracia Lux C, Joshi-Barr S, Nguyen T, Mahmoud E, Schopf E, Fomina N, Almutairi A. Biocompatible polymeric nanoparticles degrade and release cargo in response to biologically relevant levels of hydrogen peroxide. Journal of the American Chemical Society. 2012;134:15758-15764.
Fernando, M. McEnery and S. Guelcher, Advances in Polyurethane Biomaterials, 2016, pp. 481-501.
Gupta MK, Meyer TA, Nelson CE, Duvall CL. Poly(ps-b-dma) micelles for reactive oxygen species triggered drug release. Journal of Controlled Release. 2012;162:591-598.
Han P, Ma N, Ren H, Xu H, Li Z, Wang Z, Zhang X. Oxidation-responsive micelles based on a selenium-containing polymeric superamphiphile. Langmuir. 2010;26:14414-14418.
Li H, Yu SS, Miteva M, Nelson CE, Werfel T, Giorgio TD, Duvall CL. Matrix metalloproteinase responsive, proximity-activated polymeric nanoparticles for sirna delivery. Advanced Functional Materials. 2013;23:3040-3052.
Napoli A, Valentini M, Tirelli N, Muller M, Hubbell JA. Oxidation-responsive polymeric vesicles. Nat Mater. 2004;3:183-189.

* cited by examiner

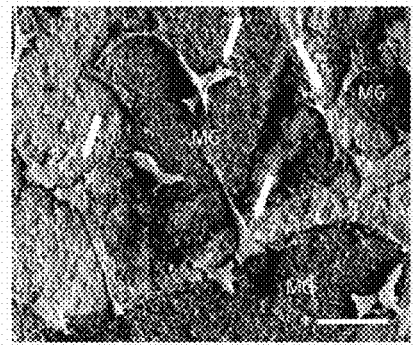
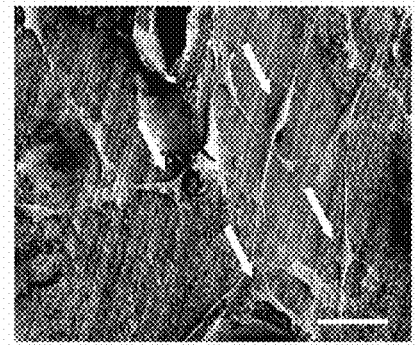
FIG. 18A          FIG. 18B
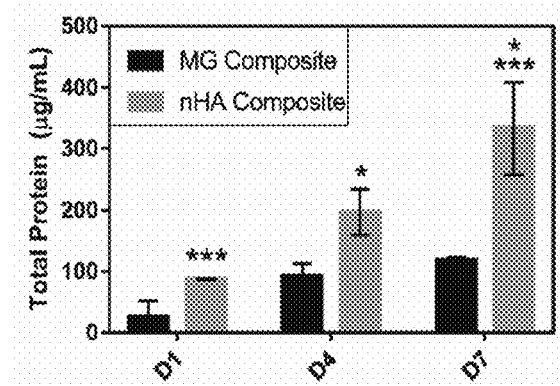
FIG. 18C
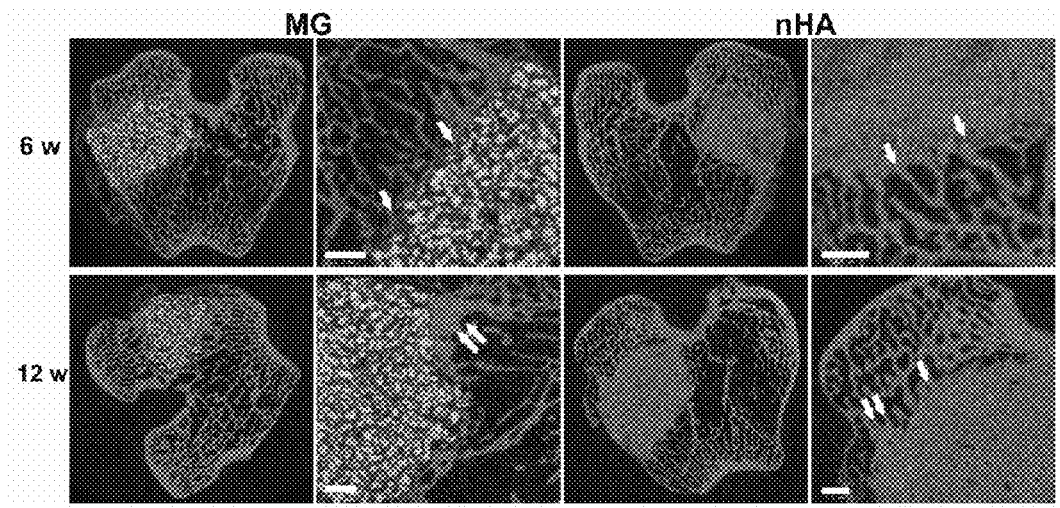
FIG. 19

POLY(THIOKETAL-URETHANE) SCAFFOLDS AND METHODS OF USE

RELATED APPLICATIONS

This application claims the benefit of U.S. Provisional Application Ser. No. 62/242,226, filed Oct. 15, 2015, and is a continuation-in-part of U.S. patent application Ser. No. 14/430,130, filed Jul. 13, 2015, which claims priority from International Patent Application No. PCT/US2013/61064, filed Sep. 20, 2013, which claims priority from U.S. Provisional Application Ser. No. 61/704,351, filed Sep. 21, 2012, the entire disclosures of which are incorporated herein by this reference.

GOVERNMENT SUPPORT

This invention was made with government support under Grant No. W81XWH-07-1-0211 awarded by the Department of Defense (DOD) Orthopedic Extremity Trauma Research Program, Grant Nos. DMR-0847711 and DMR-1006558 awarded by the National Science Foundation, and Grant Nos. R21EB012750 and R01AR056138 awarded by the National Institute of Health. The government has certain rights in the invention.

TECHNICAL FIELD

The presently-disclosed subject matter relates to poly (thioketal-urethane) scaffolds. Embodiments of the presently-disclosed subject matter further relate to method of utilizing and synthesizing polythioketal scaffolds, including poly(thioketal-urethane) scaffolds.

BACKGROUND

Wound healing is also a universal problem, particularly given the increases in immobile aging, diabetic amputees, paralyzed patients afflicted with large chronic wounds and fistulas, and trauma victims with large cutaneous defects. These well known problems indicate a need for the development of injectable biomaterials to promote restoration of tissue integrity.

One attempt to meet some of these needs includes the formation of injectable and settable bone cements. Many of these materials restore function to bone damaged by trauma or disease in a number of orthopedic procedures, such as vertebroplasty, repair of tibial plateau fractures, and screw augmentation. For example, Poly(methyl methacrylate) (PMMA) bone cements exhibit mechanical properties exceeding those of trabecular bone, and therefore provide mechanical stability to damaged bone. However, PMMA cements are non-resorbable and do not integrate with host bone. Additionally, while ceramic bone cements are osteoconductive and integrate with host bone, their brittle mechanical properties preclude their use in weight-bearing applications.

Due to the drawbacks associated with settable bone cements, composites of ceramics with resorbable polymers have emerged as an alternative approach that combines the ductile mechanical properties of polymers with the osteoconductivity of ceramics to provide mechanical stability and integration with host bone. Various biodegradable scaffolds made from synthetic polymers have been extensively investigated for use in tissue engineering and regenerative medicine. Examples include poly(lactic-co-glycolic acid) (PLGA), poly(ϑ-caprolactone) (PCL), polyanhydrides (PAA), and polyurethanes, all of which have a history of use in products approved by the FDA. These materials are applicable for a diverse range of regenerative applications because they offer a high degree of tunability, generate a minimal host inflammatory response, and degrade into non-cytotoxic components that are easily cleared from the body.

To attempt to overcome some of these known problems, polyurethane (PUR) (or poly(ester urethane) (PEUR)) scaffolds have been developed that can foam and cure in situ. Such polyurethane scaffolds can comprise polyesters that degrade hydrolytically, and have been shown to have promising properties for treating skin and bone. However, because degradation occurs primarily by acid-catalyzed hydrolysis of ester bonds in the amorphous soft segment, hydroxyl and carboxylic acid end groups are formed. The residual carboxylic acids in the polymer reduce the local pH at later stages of degradation, thereby catalyzing further hydrolysis of the polymer.

This auto-catalytic degradation of the PEUR network driven by residual carboxylic acid groups can result in a mismatch in the rates of scaffold degradation and tissue in-growth that leads to resorption gaps and compromised tissue regeneration. Various strategies have been investigated to modify the degradation rates and decrease the accumulation of acidic by-products of polyester-based scaffolds. However, the initial rate of polyester hydrolysis is primarily dictated by the presence of water, is first order with respect to the concentration of ester bonds, and does not correlate to specific cellular activities. Thus, matching the rates of scaffold degradation and tissue ingrowth is challenging for polyester-based platforms.

Biomaterials that degrade by cell-mediated mechanisms, such as materials with protease-cleavable peptides, have been exposed as potential alternatives to polyester-based platforms. However, these peptide sequences are cleaved by specific enzymes that are upregulated in specific pathological environments, making it difficult to establish this approach as a generalizable tissue engineering platform. Also, manufacturing peptides on the scale necessary to regenerate sizable tissue sections is both relatively expensive and time-consuming.

Hence, there remains a need for tissue scaffolds that do not have the same problems associated with the composites and scaffolds discussed above. Additionally, there remains a need for scaffolds that treat tissue, including bone tissue and/or skin tissue wounds, and has tunable and controlled degradation characteristics. It is also desirable to have scaffolds that are moldable, injectable, capable of implantation via minimally invasive techniques, capable of curing in situ, and/or capable of flowing to fill contours or irregular shapes.

SUMMARY

The presently-disclosed subject matter meets some or all of the above-identified needs, as will become evident to those of ordinary skill in the art after a study of information provided in this document.

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned, likewise, those features can be applied to other embodiments of the presently disclosed subject matter, whether listed in this Summary or not. To avoid excessive repetition, this Summary does not list or suggest all possible combinations of such features.

The presently-disclosed subject matter includes biodegradable scaffolds that comprise a plurality of polythioketal polymers and a plurality of polyisocyanates. In some embodiments the scaffolds comprise a cross-linked network of the polythioketal polymers and the polyisocyanates, wherein at least one polyisocyanate is linked to at least one polythioketal polymer to form the scaffold. Embodiments of scaffolds can degrade at rates that are partially or exclusively dependent on the concentration of reactive oxygen species (ROS) that the scaffolds are exposed to. In some embodiments the scaffolds have a half-life of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks.

In some embodiments the scaffold can further comprise a catalyst. Exemplary catalysts include those that comprise an amine, such as a solution of triethylene diamine in dipropyleneglycol (TEGOAMIN33).

With respect to the polythioketal polymers, in some embodiments the polythioketal polymers comprise one or more ether groups. In yet further embodiments the polythioketal polymers can comprise one or more terminal functional groups. Terminal functional groups include, but are not limited to, groups consisting of thiol, amine, hydroxyl, and combinations thereof. In specific embodiments the polythioketal polymer comprises two terminal functional groups, such as two thiol or two hydroxyl functional groups. Consequently, exemplary polythioketal polymers can be diols.

The polythioketal polymers can be comprised of a dithiol, of a poly(ethylene glycol) dithiol), additional subunits, or a combination thereof. The polythioketal polymers can be comprised of any dithiol subunit (monomer). For example, the poly(ethylene glycol) dithiol can be selected from the group consisting of di(ethylene glycol) dithiol, tri(ethylene glycol) dithiol, tetra(ethylene glycol) dithiol, hexa(ethylene glycol) dithiol, and combinations thereof. In some embodiments the scaffold comprises a poly(ethylene glycol) dithiol and another dithiol, and a molar ratio of the poly(ethylene glycol) dithiol to the dithiol is about 100:0 to about 0:100. In specific embodiments the polythioketal polymers are comprised of subunits selected from 2,2-dimethoxypropane (DMP), 1,4-butanedithiol (BDT), 2-mercatoethylether (MEE), and combinations thereof. In some embodiments the polythioketal polymer consist of DMP, BDT, and MEE. In embodiments of polythioketal polymers that comprise at least MEE and BDT, a molar ratio of MEE to the BDT can range from about 100:0 to about 0:100.

Further, in some embodiments the polythioketal polymers include the formula:

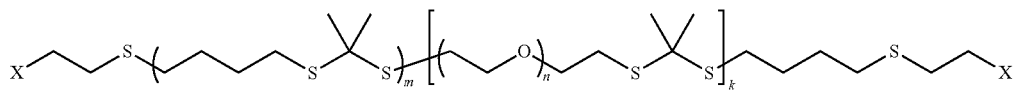

wherein n is about one to about twelve, m is about zero to about five, k is about zero to about five, and X is hydroxyl, thiol, amine, or a combination thereof.

With regard to the polyisocyanates, in some embodiments the polyisocyanates are a bifunctional polyisocyanate, a trifunctional polyisocyanate, or combinations thereof. Exemplary polyisocyanates include those selected from the group consisting of lysine methyl ester diisocyanate (LDI), lysine triisocyanate (LTI), 1,4-diisocyanatobutane (BDI), hexamethylene diisocyanate (HDI), dimers of HDI, trimers of HDI (HDIt), and combinations thereof. In specific embodiments the polyisocyanate consists of HDIt.

In further embodiments, scaffolds can also comprise a second agent to be delivered. In some embodiments the scaffolds comprise a biologically active agent. Exemplary biologically active agents include those selected from the group consisting of enzymes, organic catalysts, antibiotics, anti-cancer agents, ribozymes, organometallics, proteins, glycoproteins, peptides, polyamino acids, antibodies, nucleic acids, steroidal molecules, antibiotics, antivirals, antimycotics, anticancer agents, analgesic agents, antirejection agents, immunosuppressants, cytokines, carbohydrates, oleophobics, lipids, extracellular matrix and/or its individual components, demineralized bone matrix, mineralized bone, pharmaceuticals, chemotherapeutics, cells, viruses, siRNA, miRNA, virus vectors, prions, and combinations thereof.

Additionally, the presently-disclosed subject matter includes methods for treating tissue in a subject in need thereof by utilizing the present scaffolds. In particular, treatment methods can comprise contacting the tissue with an effective amount of a biodegradable scaffold that includes a plurality of polythioketal polymers and a plurality of polyisocyanates. The tissue can be skin, bone, or the like. The particular tissue being treated can be a wound site.

In some embodiments, in the contacting step described above, the polythioketal polymers and the polyisocyanates are contacted with the tissue in a fully-uncured (100% polyisocyanate and polythioketal polymer) or a partially-uncured state (partial conversion to polythioketal-urethane scaffold). The method for treating a subject can further comprise allowing the polythioketal polymers and the polyisocyanates to cure in contact with the tissue so that at least one polyisocyanate is linked to at least one polythioketal polymer to form the scaffold. Thus, in some embodiments the step of contacting tissue with the present scaffolds includes curing the present scaffolds in situ.

In some embodiments the method further comprises permitting the scaffold to degrade on the tissue for about 1 day to about 100 days or more.

The treatment methods described herein can further include delivering an agent to a subject and/or a tissue of a subject. For example, in some embodiments the scaffolds comprise a biologically active agent that can be delivered to a subject and/or tissue of a subject.

Further still, the presently-disclosed subject matter includes a method for manufacturing a biodegradable scaffold. In some embodiments the manufacturing method comprises providing a polythioketal polymer, mixing the polythioketal polymer with a polyisocyanate to form a reactive mixture, and curing the reactive mixture into the biodegradable scaffold. The method can further comprise mixing a catalyst or other agent (e.g., biologically active agent) into the reactive mixture. The reactive mixture can be cured such that at least one polyisocyanate is linked to at least one polythioketal polymer to form the scaffold. Thus, the method can form a cured scaffold that comprises a cross-linked network of the polythioketal polymers and the polyisocyanates.

In some embodiments the step of providing a polythioketal polymer includes reacting a mixture that includes a dithiol, a poly(ethylene glycol) dithiol, or a combination thereof to form the polythioketal polymer. In specific embodiments the of providing the polythioketal polymer includes reacting a mixture that includes 2,2-dimethoxypropane (DMP), 1,4-butanedithiol (BDT), 2-mercatoethylether (MEE), or a combination thereof to form the polythioketal polymer. In specific embodiments DMP, BDT, and MEE are reacted to from a polythioketal polymer.

In some embodiments the step of providing the polythioketal polymer includes functionalizing the polythioketal polymer to include the terminal functional group. Exemplary terminal functional groups include, thiol, amine, hydroxyl, and combinations thereof.

Further advantages of the presently-disclosed subject matter will become evident to those of ordinary skill in the art after a study of the description, Figures, and non-limiting Examples in this document.

DEFINITIONS

The term "bioactive agent" or "biologically active agent" is used herein to refer to compounds or entities that alter, promote, speed, prolong, inhibit, activate, or otherwise affect biological or chemical events in a subject (e.g., a human). For example, bioactive agents may include, but are not limited to osteogenic, osteoinductive, and osteoconductive agents, anti-HIV substances, anti-cancer substances, antibiotics, immunosuppressants, anti-viral agents, enzyme inhibitors, neurotoxins, opioids, hypnotics, anti-histamines, lubricants, tranquilizers, anti-convulsants, muscle relaxants, anti-Parkinson agents, anti-spasmodics and muscle contractants including channel blockers, miotics and anti-cholinergics, anti-glaucoma compounds, anti-parasite agents, anti-protozoal agents, and/or anti-fungal agents, modulators of cell-extracellular matrix interactions including cell growth inhibitors and anti-adhesion molecules, vasodilating agents, inhibitors of DNA, RNA, or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotics, targeting agents, chemotactic factors, receptors, neurotransmitters, proteins, cell response modifiers, cells, peptides, polynucleotides, viruses, and vaccines. In certain embodiments, the bioactive agent is a drug. In certain embodiments, the bioactive agent is a small molecule.

Antimicrobial used as bioactive agents in embodiments of the present invention may be selected from one that does little to no harm to the healing process. Clinically, antibiotics may be selected for their spectrum or ease of administration to the patient. When selecting an antibiotic for local delivery, the physical characteristics (charge and hydrophobicity) and state (liquid or powder) of the drug may also be considered. Additionally, antimicrobials' effects on eukaryotic cells may be considered when developing an embodiment of the present invention, including a dual-delivery scaffold embodiment. In vitro studies that evaluated the effect of eight concentrations (ranging from 0 to 5,000 mg/ml) of 21 antibiotics on the viability and activity of osteoblasts found that vancomycin, a tricyclic glycopeptide antibiotic that is efficacious for treating infections caused by gram-positive bacteria such as *Staph. aureus*, may have the least detrimental effects on osteoblast function. All other antibiotics in the study reduced the alkaline phosphatase (ALP) activity at doses that were 10-50 times lower than that of vancomycin. Other studies also indicate that vancomycin has less adverse effects on osteoblasts than other commonly used antibiotics in vitro. Furthermore, vancomycin may not impede bone growth in fractures in vivo. Some embodiments comprise an antibiotic selected from the group consisting of clindamycin, cefazolin, oxacillin, rifampin, trimethoprim/sulfamethoxazole, vancomycin, ceftazadime, ciprofloxacin, colistin, and imipenem.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, the United States Pharmacopeia-25/National Formulary-20, published by the United States Pharmcopeial Convention, Inc., Rockville Md., 2001, and the "Pharmazeutische Wirkstoffe", edited by Von Keemann et al., Stuttgart/New York, 1987, all of which are incorporated herein by reference. Drugs for human use listed by the U.S. Food and Drug Administration (FDA) under 21 C.F.R. § § 330.5, 331 through 361, and 440 through 460, and drugs for veterinary use listed by the FDA under 21 C.F.R. § § 500 through 589, all of which are incorporated herein by reference, are also considered acceptable for use in accordance with the present invention.

The terms, "biodegradable", "bioerodable", or "resorbable" materials, as used herein, are intended to describe materials that degrade under physiological conditions to form a product that can be metabolized or excreted without damage to the subject. In certain embodiments, the product is metabolized or excreted without permanent damage to the subject. Biodegradable materials may be hydrolytically degradable, may require cellular and/or enzymatic action to fully degrade, or both. Biodegradable materials also include materials that are broken down within cells. Degradation may occur by hydrolysis, oxidation, enzymatic processes, phagocytosis, or other processes. Some degradation may occur due to the present of reactive oxygen species.

The term "biocompatible" as used herein, is intended to describe materials that, upon administration in vivo, do not induce undesirable side effects. In some embodiments, the material does not induce irreversible, undesirable side effects. In certain embodiments, a material is biocompatible if it does not induce long term undesirable side effects. In certain embodiments, the risks and benefits of administering a material are weighed in order to determine whether a material is sufficiently biocompatible to be administered to a subject.

The term "biomolecules" as used herein, refers to classes of molecules (e.g., proteins, amino acids, peptides, polynucleotides, nucleotides, carbohydrates, sugars, lipids, nucleoproteins, glycoproteins, lipoproteins, steroids, natural products, etc.) that are commonly found or produced in cells, whether the molecules themselves are naturally-occurring or artificially created (e.g., by synthetic or recombinant methods). For example, biomolecules include, but are not limited to, enzymes, receptors, glycosaminoglycans, neurotransmitters, hormones, cytokines, cell response modifiers such as growth factors and chemotactic factors, antibodies, vaccines, haptens, toxins, interferons, ribozymes, anti-sense agents, plasmids, DNA, and RNA. Exemplary growth factors include but are not limited to bone morphogenic proteins (BMP's) and their active fragments or subunits. In some embodiments, the biomolecule is a growth factor, chemotactic factor, cytokine, extracellular matrix molecule, or a fragment or derivative thereof, for example, a cell attachment sequence such as a peptide containing the sequence, RGD.

The term "carbohydrate" as used herein, refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

The term "composite" as used herein, is used to refer to a unified combination of two or more distinct materials. The composite may be homogeneous or heterogeneous. For example, a composite may be a combination of bone particles and a polymer; a combination of bone particles, polymers and antibiotics; or a combination of two different polymers. In certain embodiments, the composite has a particular orientation.

The term "contacting" refers to any method of providing or delivering a scaffold on to or near tissue to be treated. Such methods are described throughout this document, and include injection of a biodegradable scaffold on to a tissue wound and/or molding a biodegradable scaffold in a mold and then placing the molded scaffold on a tissue wound. In some embodiments contacting refers to completely covering a skin wound, and optionally the surrounding skin, with a biodegradable polyurethane scaffold. In some embodiments contacting refers to placing a biodegradable polyurethane scaffold between two or more bone fragments that have fractured. In various aspects, a scaffold can be contact an existing tissue wound, and in further various aspects a polyurethane scaffold can be contacted prophylactically; that is, to prevent a wound from forming on tissue.

The term "flowable polymer material" as used herein, refers to a flowable composition including one or more of monomers, pre-polymers, oligomers, low molecular weight polymers, uncross-linked polymers, partially cross-linked polymers, partially polymerized polymers, polymers, or combinations thereof that have been rendered formable. One skilled in the art will recognize that a flowable polymer material need not be a polymer but may be polymerizable. In some embodiments, flowable polymer materials include polymers that have been heated past their glass transition or melting point. Alternatively or in addition, a flowable polymer material may include partially polymerized polymer, telechelic polymer, or prepolymer. A pre-polymer is a low molecular weight oligomer typically produced through step growth polymerization. The pre-polymer is formed with an excess of one of the components to produce molecules that are all terminated with the same group. For example, a diol and an excess of a diisocyanate may be polymerized to produce isocyanate terminated prepolymer that may be combined with a diol to form a polyurethane. Alternatively or in addition, a flowable polymer material may be a polymer material/solvent mixture that sets when the solvent is removed.

The term "nontoxic" is used herein to refer to substances which, upon ingestion, inhalation, or absorption through the skin by a human or animal, do not cause, either acutely or chronically, damage to living tissue, impairment of the central nervous system, severe illness or death.

The term "osteoconductive" as used herein, refers to the ability of a substance or material to provide surfaces which are receptive to the growth of new bone.

The term "osteogenic" as used herein, refers to the ability of a substance or material that can induce bone formation.

The term "osteoinductive" as used herein, refers to the quality of being able to recruit cells (e.g., osteoblasts) from the host that have the potential to stimulate new bone formation. In general, osteoinductive materials are capable of inducing heterotopic ossification, that is, bone formation in extraskeletal soft tissues (e.g., muscle).

The term "osteoimplant" is used herein in its broadest sense and is not intended to be limited to any particular shapes, sizes, configurations, compositions, or applications. Osteoimplant refers to any device or material for implantation that aids or augments bone formation or healing. Osteoimplants are often applied at a bone defect site, e.g., one resulting from injury, defect brought about during the course of surgery, infection, malignancy, inflammation, or developmental malformation. Osteoimplants can be used in a variety of orthopedic, neurosurgical, dental, and oral and maxillofacial surgical procedures such as the repair of simple and compound fractures and non-unions, external, and internal fixations, joint reconstructions such as arthrodesis, general arthroplasty, deficit filling, disectomy, laminectomy, anterior cerival and thoracic operations, spinal fusions, etc.

The terms "polynucleotide", "nucleic acid", or "oligonucleotide" as used herein, refer to a polymer of nucleotides. The terms "polynucleotide", "nucleic acid", and "oligonucleotide", may be used interchangeably. Typically, a polynucleotide comprises at least three nucleotides. DNAs and RNAs are exemplary polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thithymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyriboses, arabinose, and hexose), or modified phosphate groups (e.g., phosphorothioates and 5'-N-phosphoramidite linkages). The polymer may also be a short strand of nucleic acids such as RNAi, siRNA, or shRNA.

The terms "polypeptide", "peptide", or "protein" as used herein, include a string of at least three amino acids linked together by peptide bonds. The terms "polypeptide", "peptide", and "protein", may be used interchangeably. In some embodiments, peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide" or "oligosaccharide" as used herein, refer to any polymer or oligomer of carbohydrate residues. Polymers or oligomers may consist of anywhere from two to hundreds to thousands of sugar units or more. "Oligosaccharide" generally refers to a relatively low molecular weight polymer, while "polysaccharide" typically refers to a higher molecular weight polymer. Polysaccharides may be purified from natural sources such as plants or may be synthesized de novo in the laboratory. Polysaccharides isolated from natural sources may be modified chemically to change their chemical or physical properties (e.g., reduced, oxidized, phosphorylated, cross-linked). Carbohydrate polymers or oligomers may include natural sugars (e.g., glucose, fructose, galactose, mannose, arabinose, ribose, xylose, etc.) and/or modified sugars (e.g., 2'-fluororibose, 2'-deoxyribose, etc.). Polysaccharides may also be either straight or branched. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, poly(dextrose), and fructose. In some embodiments, glycosaminoglycans are considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

The term "porogen" as used herein, refers to a chemical compound that may be part of the inventive composite and upon implantation/injection or prior to implantation/injection diffuses, dissolves, and/or degrades to leave a pore in the osteoimplant composite. A porogen may be introduced into the composite during manufacture, during preparation of the composite (e.g., in the operating room), or after implantation/injection. A porogen essentially reserves space in the composite while the composite is being molded but once the composite is implanted the porogen diffuses, dissolves, or degrades, thereby inducing porosity into the composite. In this way porogens provide latent pores. In certain embodiments, the porogen may be leached out of the composite before implantation/injection. This resulting porosity of the implant generated during manufacture or after implantation/injection (i.e., "latent porosity") is thought to allow infiltration by cells, bone formation, bone remodeling, osteoinduction, osteoconduction, and/or faster degradation of the osteoimplant. A porogen may be a gas (e.g., carbon dioxide, nitrogen, or other inert gas), liquid (e.g., water, biological fluid), or solid. Porogens are typically water soluble such as salts, sugars (e.g., sugar alcohols), polysaccharides (e.g., dextran (poly(dextrose)), water soluble small molecules, etc. Porogens can also be natural or synthetic polymers, oligomers, or monomers that are water soluble or degrade quickly under physiological conditions. Exemplary polymers include polyethylene glycol, poly(vinylpyrollidone), pullulan, poly(glycolide), poly(lactide), poly(lactide-co-glycolide), other polyesters, and starches. In certain embodiments, bone particles utilized in provided composites or compositions may act as porogens. For example, osteoclasts resorb allograft and make pores in composites.

In some embodiments, porogens may refer to a blowing agent (i.e., an agent that participates in a chemical reaction to generate a gas). Water may act as such a blowing agent or porogen.

The term "porosity" as used herein, refers to the average amount of non-solid space contained in a material (e.g., a composite of the present invention). Such space is considered void of volume even if it contains a substance that is liquid at ambient or physiological temperature, e.g., 0.5° C. to 50° C. Porosity or void volume of a composite can be defined as the ratio of the total volume of the pores (i.e., void volume) in the material to the overall volume of composites. In some embodiments, porosity ($\Box\Box$, defined as the volume fraction pores, can be calculated from composite foam density, which can be measured gravimetrically. Porosity may in certain embodiments refer to "latent porosity" wherein pores are only formed upon diffusion, dissolution, or degradation of a material occupying the pores. In such an instance, pores may be formed after implantation/injection. It will be appreciated by these of ordinary skill in the art that the porosity of a provided composite or composition may change over time, in some embodiments, after implantation/injection (e.g., after leaching of a porogen, when osteoclasts resorbing allograft bone, etc.). For the purpose of the present disclosure, implantation/injection may be considered to be "time zero" ($T_0$). In some embodiments, the present invention provides composites and/or compositions having a porosity of at least about 30%, at least about 40%, at least about 50%, at least about 60%, at least about 70%, at least about 80%, at least about 90% or more than 90%, at time zero. In certain embodiments, pre-molded composites and/or compositions may have a porosity of at least about 30%, at least about 40%, at least about 50%, at least about 60%, at least about 70%, at least about 80%, at least about 90% or more than 90%, at time zero. In certain embodiments, injectable composites and/or compositions may have a porosity of as low as 3% at time zero. In certain embodiments, injectable composites and/or compositions may cure in situ and have a porosity of at least about 30%, at least about 40%, at least about 50%, at least about 60%, at least about 70%, at least about 80%, at least about 90% or more than 90% after curing.

The term "remodeling" as used herein, describes the process by which native bone, processed bone allograft, whole bone sections employed as grafts, and/or other bony tissues are replaced with new cell-containing host bone tissue by the action of osteoclasts and osteoblasts. Remodeling also describes the process by which non-bony native tissue and tissue grafts are removed and replaced with new, cell-containing tissue in vivo. Remodeling also describes how inorganic materials (e.g., calcium-phosphate materials, such as β-tricalcium phosphate) are replaced with living bone.

The term "scaffold" as used herein refers to a substance that can be used to treat tissue and/or a wound. In some embodiments the scaffold or graft is a foam that can be injected between fractured bone fragments to help heal the fracture. In some embodiments the scaffold or graft is a material that can be placed on or near tissue to be treated. The terms "composite", "scaffold", and "graft" may be used interchangeably herein to refer to embodiments of the presently-disclosed subject matter.

The term "setting time" as used herein, is approximated by the tack-free time (TFT), which is defined as the time at which the material could be touched with a spatula with no adhesion of the spatula to the foam. At the TFT, the wound could be closed without altering the properties of the material.

The term "shaped" as used herein, is intended to characterize a material (e.g., composite) or an osteoimplant refers to a material or osteoimplant of a determined or regular form or configuration in contrast to an indeterminate or vague form or configuration (as in the case of a lump or other solid matrix of special form). Materials may be shaped into any shape, configuration, or size. For example, materials can be shaped as sheets, blocks, plates, disks, cones, pins, screws, tubes, teeth, bones, portions of bones, wedges, cylinders, threaded cylinders, and the like, as well as more complex geometric configurations.

The term "small molecule" as used herein, is used to refer to molecules, whether naturally-occurring or artificially created (e.g., via chemical synthesis), that have a relatively low molecular weight. In some embodiments, small molecules have a molecular weight of less than about 2,500 g/mol, for example, less than 1000 g/mol. In certain embodiments, small molecules are biologically active in that they produce a local or systemic effect in animals, such as mammals, e.g., humans. In certain embodiments, a small molecule is a drug. In certain embodiments, though not necessarily, a drug is one that has already been deemed safe and effective for use by an appropriate governmental agency or body (e.g., the U.S. Food and Drug Administration).

The terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The term "tissue" is used herein to refer to a population of cells, generally consisting of cells of the same kind that perform the same or similar functions. The types of cells that make the tissue are not limited. In some embodiments tissue is part of a living organism, and in some embodiments tissue is tissue excised from a living organism or artificial tissue. In some embodiments tissue can be part of skin, bone, an organ or the like.

The term "transformation" as used herein, describes a process by which a material is removed from an implant site and replaced by host tissue after implantation. Transformation may be accomplished by a combination of processes, including but not limited to remodeling, degradation, resorption, and tissue growth and/or formation. Removal of the material may be cell-mediated or accomplished through chemical processes, such as dissolution and hydrolysis.

The terms "treatment" or "treating" refer to the medical management of a patient with the intent to heal, cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. For example, in some embodiments treatment refers to the healing bone tissue that is fractured and/or healing wounded skin tissue.

The term "wet compressive strength" as used herein, refers to the compressive strength of an osteoimplant after being immersed in physiological saline (e.g., phosphate-buffered saline (PBS), water containing 0.9 g NaCl/100 ml water, etc.) for a minimum of 12 hours (e.g., 24 hours). Compressive strength and modulus are well-known measurements of mechanical properties and is measured using the procedure described herein The term "working time" as used herein, is defined in the ISO9917 standard as "the period of time, measured from the start of mixing, during which it is possible to manipulate a dental material without an adverse effect on its properties" (Clarkin et al., *J Mater Sci: Mater Med* 2009; 20:1563-1570). In some embodiments, the working time for a two-component polyurethane is determined by the gel point, the time at which the crosslink density of the polymer network is sufficiently high that the material gels and no longer flows. According to the present invention, the working time is measured by loading the syringe with the reactive composite and injecting <0.25 ml every 30 s. The working time is noted as the time at which the material was more difficult to inject, indicating a significant change in viscosity.

The term "wound" as used herein refers to any defect, injury, disorder, damage, or the like of tissue. In some embodiments a wound can be a bone fracture. In some embodiments a wound is damaged skin or skin that must heal from a particular disorder.

BRIEF DESCRIPTION OF THE DRAWINGS

FIGS. 18A-C show graphs and images of MC3T3 cell proliferation on MG and nHA composites. (A) Image showing cells (arrows) attached and spread on MG composites after 24 h incubation. (B) Image showing cells (arrows) attached and spread on nHA composites after 24 h incubation. Scale bar=50 μm. (C) Measurements of total protein versus time indicate that cells proliferated faster on nHA composites.

FIG. 19 shows images of transverse μCT sections of PTKUR/MG and PTKUR/nHA composite cements explanted at 6 and 12 weeks. Higher magnification images of the defect periphery show evidence of trabecular infiltration (single white arrows) and trabecular densification (double white arrows). Scale bar=1 mm.

DESCRIPTION OF EXEMPLARY EMBODIMENTS

Figure 1:
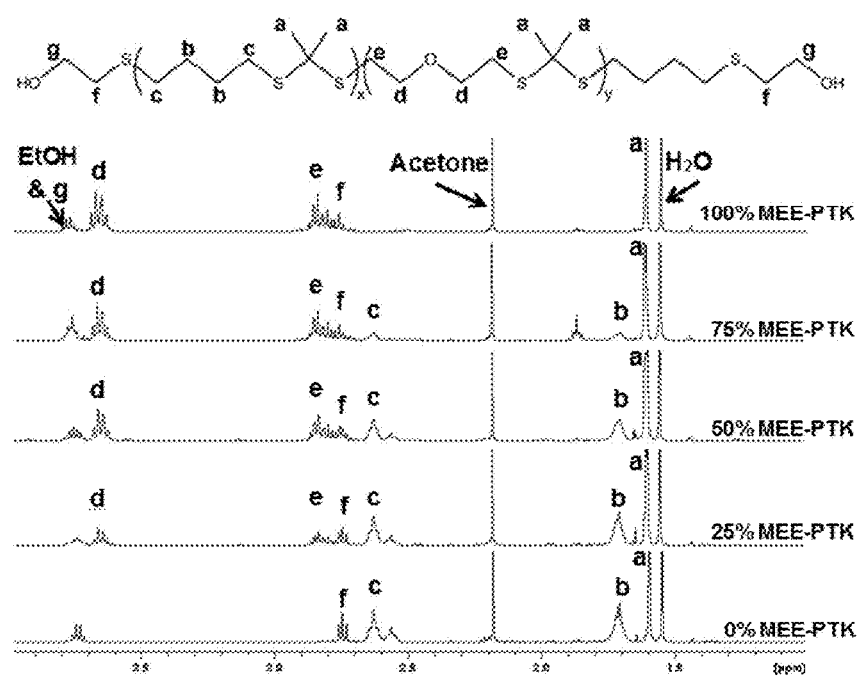
FIG. 1 includes $^1$H-NMR spectra of the synthesized PTK polymers that are copolymer diols, where peaks associated with MEE and BDT monomers correlated with molar composition used in the polymer feed.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Aspects of the presently-disclosed subject matter include biodegradable poly(thioketal-urethane) (PTK-UR) tissue scaffolds. In some embodiments the scaffolds comprise a polythioketal polymer and polyisocyanates. Exemplary scaffolds can be used to treat tissue. Other exemplary scaffolds can also be used as delivery systems for biologically active agents to promote tissue healing and regeneration.

The present inventors discovered a more ubiquitous cell-mediated signal for scaffold degradation. ROS are key mediators of cell function in both health and disease, especially at sites of inflammation and tissue healing. Utilizing these cell-generated molecules as triggers for selective polymer degradation, the present inventors conceived of a tissue scaffold with well-matched rates of tissue ingrowth and cell-mediated scaffold degradation. Novel poly(thioketal) polymers featuring tunable reactive end-chemistries, chain compositions, and ROS-mediated degradation rates have been developed towards this end. These PTK polymers can be incorporated into 3D porous tissue engineering scaffolds with more robust mechanical properties than similar constructs fabricated from standard polyesters. PTK-UR scaffolds can be selectively degraded by ROS and could be stable under aqueous conditions. Thus, embodiments of the present scaffolds exhibit biodegradability that is cell-mediated. Moreover, the oxidative degradation rates of the PTK-URs can follow first-order degradation kinetics and exhibit dose-dependent degradation with respect to ROS levels. PTK scaffolds can support cell growth, cell infiltration, and granulation tissue formation. PTK-URs represent a useful new class of biomaterials that provide a robust, cell-degradable substrate for guiding new tissue formation.

Some embodiments of the presently-disclosed subject matter relate to scaffolds that can be used in a large variety of clinical applications, for example, as bone void fillers, to repair or help healing of skeletal deficiencies resulting from trauma, tumors, surgery, iatrogenic, congenital, genetic, metabolic and degenerative or abnormal development, and inflammatory infection. In some embodiments, scaffolds promote cellular infiltration from adjacent osseous tissues, thus accelerating the remodeling process. In some embodiments scaffolds aid in the treatment of cutaneous wounds.

The presently-disclosed subject matter also provides methods of preparing and using inventive composites as well as kits for preparing and/or administering inventive composites. Inventive porous composites may be prepared using any of a variety of methods. In some embodiments, inventive composites are prepared using a method that includes water as a blowing agent. In one embodiment, the scaffolds are injected, extruded, molded, or similarly delivered to a tissue site (e.g., bony defect or cutaneous wound) of a subject. Inventive composites are engineered to set in situ to form a solid composite that may have a desired or predetermined mechanical strength. In certain embodiments, the scaffolds may include monomers or pre-polymers.

I) Polymer Component

Synthetic polymers can be designed with properties targeted for a given clinical application. According to the present invention, polyurethanes (PUR) are a useful class of biomaterials due to the fact that they can be injectable or moldable as a reactive liquid that subsequently cures to form a porous composite. These materials also have tunable degradation rates, which are shown to be highly dependent on the choice of polyol and isocyanate components (Hafeman et al., *Pharmaceutical Research* 2008; 25(10):2387-99; Storey et al., *J Poly Sci Pt A: Poly Chem* 1994; 32:2345-63; Skarja et al., *J App Poly Sci* 2000; 75:1522-34). Polyurethanes have tunable mechanical properties, which can also be enhanced with the addition of bone particles and/or other components (Adhikari et al., *Biomaterials* 2008; 29:3762-70; Gorna et al., *J Biomed Mater Res Pt A* 2003; 67A(3): 813-27) and exhibit elastomeric rather than brittle mechanical properties. Polyurethanes can be made by reacting together the components of a two-component composition, one of which includes a polyisocyanate while the other includes a component having two or more hydroxyl groups (i.e., polyols) to react with the polyisocyanate. For example, U.S. Pat. No. 6,306,177, discloses a method for repairing a tissue site using polyurethanes, the content of which is incorporated by reference It is to be understood that by "a two-component composition" it means a composition comprising two essential types of components. In some embodiments, such a composition may additionally comprise one or more other optional components.

In some embodiments, polyurethane is a polymer that has been rendered formable through combination of two liquid components. For example, in one embodiment, the polyurethane is rendered formable through combination of a polythioketal (PTK) polymer and a polyisocyanate. In another embodiment, a polyisocyanate or a polythioketal polymer may be a molecule with two or more isocyanate or hydroxyl groups respectively. In a further embodiment, a polyisocyanate may have at least four isocyanates. Additionally or alternatively, the polyurethane may be rendered formable through combination of a polyisocyanate and a thioketal (TK) having two or more hydroxyl end functional groups (e.g., diol, triol, etc.).

In some embodiments, the polyurethane forms a hydrolytically stable poly(thioketal urethane)s (PTKUR) that degrades in the oxidative environments, such as those associated with bone defects. For example, in one embodiment, the PTKUR is hydrolytically stable for at least 1 month, at least 2 months, at least 3 months, at least 4 months, at least 5 months, at least 6 months, up to 6 months, or any combination, sub-combination, range, or sub-range thereof. In another embodiment, the PTKUR degrades rapidly under oxidative conditions (e.g., <1 week). In some embodiments, the polyurethanes form cell-degradable bone cements with initial bone-like strength. For example, in one embodiment, the cement formed from the polyurethane including the polyisocyanate and thioketal exhibited initial compressive strength exceeding that of trabecular bone, working times comparable to commercial bone cements (5-10 min), and degradation in response to reactive oxygen species secreted by cells. In another embodiment, when implanted into femoral condyle plug defects in rabbits, the cements supported appositional new bone growth, osteoclast-mediated resorption, and integration with host bone.

As described above, the PTK-UR scaffolds described herein are the product of the reaction between at least two components, namely a polyisocyanate and a hydroxyl end functional thioketal or a polythioketal polymer, which can be a copolymer. In some embodiments, multiple different PTK and/or PTK-URs (e.g., different structures, difference molecular weights) may be used in a composite/composition of the present invention. In some embodiments, other biocompatible and/or biodegradable polymers may be used with the present scaffolds.

Polyisocyanates, hydroxyl end functional TKs, and/or PTK polymers can be selected to produce polymers having various physiochemical properties and morphologies including, for example, flexible foams, rigid foams, elastomers, coatings, adhesives, and sealants. The properties of scaffolds are controlled by choice of the raw materials and their relative concentrations. For example, PTK comprising a relatively high concentration of ether groups, for example from 2-mercaptoethylether (MEE) subunits, can degrade at relatively faster rates that other scaffolds. The molecular weights of the PTK polymer, the subunits of the PTK polymer, and/or the polyisocyanates can also be varied to manipulate the degradability, density, and other characteristics of the scaffolds. In some embodiments the present scaffolds are comprised of a network of PTK polymers and polyisocyanates that are cross-linked (i.e., covalently bound) through a curing process. In some embodiments, pores in bone/polyurethanes composites in the present invention are interconnected and have a diameter ranging from approximately 50 to approximately 1000 microns.

As discussed above, the density of the scaffolds can be varied depending on the components selected for its manufacture. In some embodiments scaffolds can comprise a density of about 50 mg/m$^3$, about 75 mg/m$^3$, about 100 mg/m$^3$, about 125 mg/m$^3$, about 150 mg/m$^3$, about 175 mg/m$^3$, about 200 mg/m$^3$, about 225 mg/m$^3$, or about 250 mg/m$^3$. In some embodiments the scaffolds preferably will comprise a density of about 80 mg/m$^3$ to about 200 mg/m$^3$, and even more preferably of about 80 mg/m$^3$, to about 150 mg/m$^3$. In general, the density of a scaffold will increase as its porosity decreases.

Polyisocyanate. Polyisocyanates or multi-isocyanate compounds for use in the present invention include aliphatic polyisocyanates. Exemplary aliphatic polyisocyanates include, but are not limited to, lysine diisocyanate, an alkyl ester of lysine diisocyanate (for example, the methyl ester or the ethyl ester), lysine triisocyanate, hexamethylene diisocyanate, isophorone diisocyanate (IPDI), 4,4'-dicyclohexylmethane diisocyanate (H$_{12}$MDI), cyclohexyl diisocyanate, 2,2,4-(2,2,4)-trimethylhexamethylene diisocyanate (TMDI), dimers prepared form aliphatic polyisocyanates, trimers prepared from aliphatic polyisocyanates and/or mixtures thereof. In some embodiments, hexamethylene diisocyanate (HDI) trimer (HDIt) sold as Desmodur N3300A may be a polyisocyanate utilized in the present invention. In some embodiments, polyisocyanates used in the present invention includes approximately 10 to 55% NCO by weight (wt % NCO=100*(42/Mw)). In some embodiments, polyisocyanates include approximately 15 to 50% NCO.

Polyisocyanates used herein also include aromatic polyisocyanates.

Polythioketal Polymer. Some embodiments of the present invention, instead of polyester polyols, utilize a polythioketal (PTK) polymer. Any polythioketal can be used. In some embodiments the polythioketal has a molecular weight of about 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, or 20,000 g/mol. In some embodiments the PTK polymer preferably includes molecular weight of about 1,000 to about 10,000 g/mol. As is understood by those in the art, polythioketal refers to a compound having a plurality of thioketal units, which are represented by the following formula:

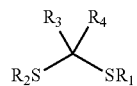

The PTK polymer itself can be made through a reaction between one or more different subunits (e.g., dithiols), as illustrated below in Scheme 1. An isocyanate can react with the terminal functional group (e.g., hydroxyl) of the PTK polymer. The relative rates of these reactions determine the scaffold morphology, working time, and setting time.

Scheme 1

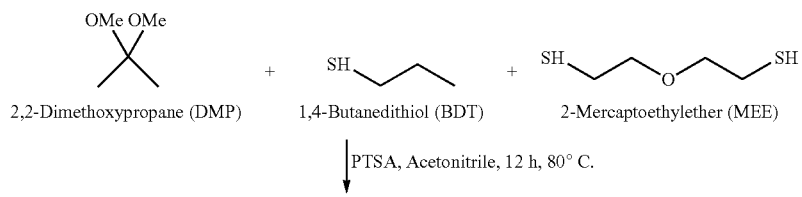

-continued

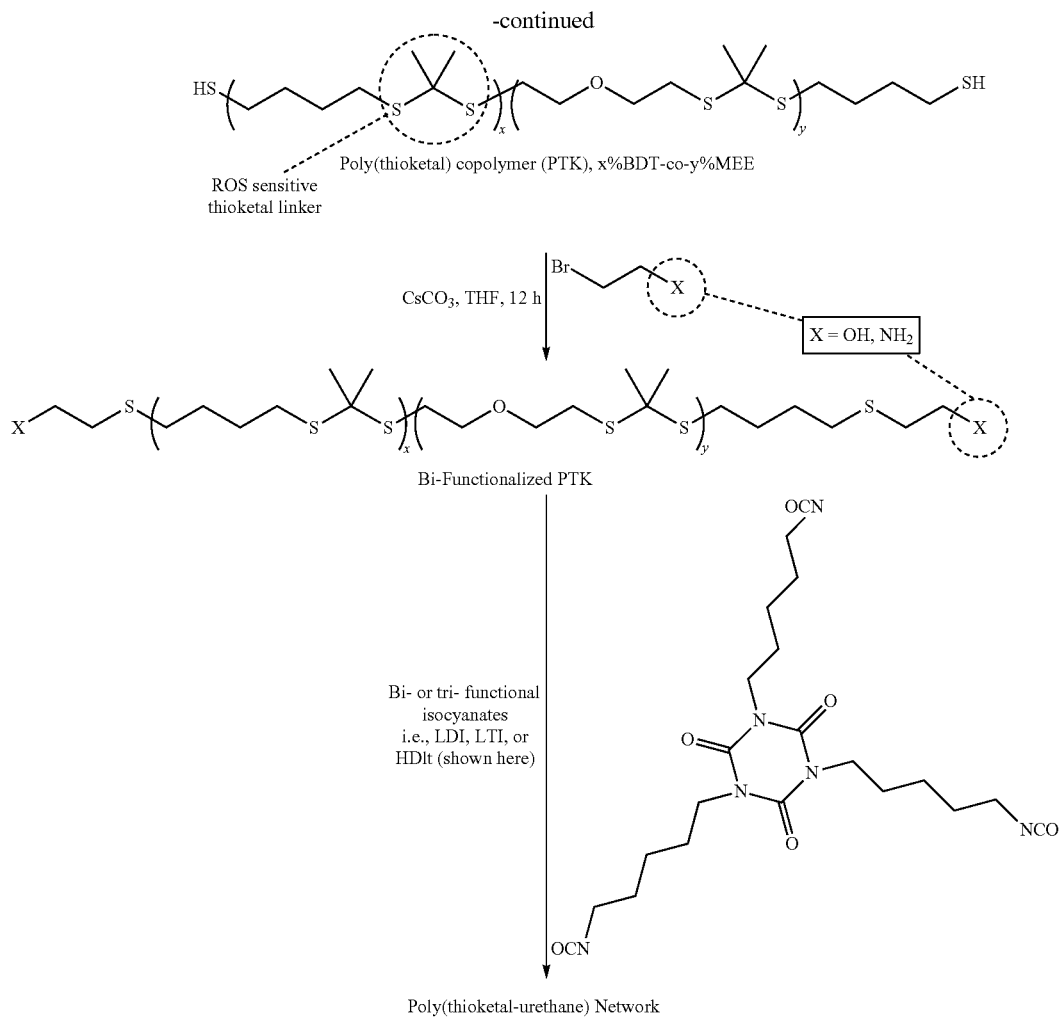

Embodiments of scaffolds that are made from a PTK advantageously do not degrade hydrolytically or at a particular pH. Embodiments of scaffolds comprising PTK also do not autocatalytically degrade. Instead, exemplary PTK scaffolds can degrade by reactive oxygen species, which are a cell-created phenomenon. Thus, the degradation rate of PTK scaffolds depends on the conditions created by the cellular environment, and is not affected by a scaffold's own degradation products. Furthermore, this mechanism helps degradation of a scaffold comprising PTK to proceed from the scaffold's exterior, where it is exposed to a biological environment, rather than from its interior where degradation products may accumulate.

The polythioketal polymer and polyisocyanate can be mixed in any proportion that results in a scaffolds having desired characteristics in terms of strength, flowability, and the like. For example, the scaffolds can comprise about 5 mol %, 10 mol %, 15 mol %, 20 mol %, 25 mol %, 30 mol %, 35 mol %, 40 mol %, 45 mol %, 50 mol %, 55 mol %, 60 mol %, 65 mol %, 70 mol %, 75 mol %, 80 mol %, 85 mol %, 90 mol %, 95 mol %, PTK polymer or polyisocyanate. Similarly to the PUR scaffolds discussed above, the ratio of PTK polymer to polyisocyanate can be optimized so there is a deficiency or an excess of the number of reactive groups of the PTK polymer in relation to the NCO equivalents on the polyisocyanate. On the other hand, in some embodiments there is an approximately stoichiometric ratio of PTK polymer functional groups to NCO groups on the polyisocyanates.

In some embodiments the reaction is balanced with use of an index. The index can be calculated using the following formula:

INDEX=100×number of NCO equivalents/number of OH, NH, or other equivalents.

Then, the relative amounts of isocyanate (e.g., HDIt) and PTK polymer can be selected so as to obtain a predetermined index. In some embodiments the index is in the range of approximately 80 to 150. In other embodiments the index is about 80, 85, 90, 95, 100, 105, 110, 115, 120, 125, 130, 135, or 140.

The tunable degradation rates of scaffolds can be varied depending on the particular environment that a scaffold comprising PTK is in. However, certain embodiments of scaffolds comprising PTK have half-lives in oxidative medium (i.e., 20 wt % hydrogen peroxide in 0.1 M cobalt chloride) of about 5 days, 10 day, 15 days, 20 days, 25 days, 30 days, 45 days, 60 days, 90 days, 120 days, 150 days, or 180 days. In other embodiments scaffolds comprising PTK have half-lives of one or more years. Preferably, for certain bone and skin treatment applications, the half-life of a scaffold comprising PTK is between 5 days and 120 days.

A further advantage of PTK scaffolds is that their degradation rates are tunable and controllable. For example, in some embodiments the degradation rate of a PTK scaffold is tuned to match the rate of cellular ingrowth and activity within the scaffold. This will allow PTK scaffolds to have superior mechanical integrity during the entire time period of tissue treatment, healing, and remodeling. Furthermore, unlike prior scaffolds, this can reduce or eliminate the extent to which gaps are formed between tissue that is growing and the scaffold that is degrading.

In some embodiments the polythioketal polymer comprises one or more ethylene glycol units, which optionally may be poly(ethylene glycol) units depending on the precursors chosen to synthesize the PTK. Thus, the PTK polymer can be a copolymer having thioketal units and ethylene glycol units, either of which may or may not be repeating in the copolymer. The polythioketal polymers can comprise any percentage of ethylene glycol units, and the scaffold may comprise about 1%, 5%, 10%, 15%, 20%, 25%, 30%, 35%, 40%, 45%, 50%, 55%, 60%, 65%, 70%, 75%, 80%, 85%, 90%, 95%, or 99% ethylene glycol units. In some embodiments the percentage of ethylene glycol in a PTK polymer is calculated based on the percentage of units in a polymer that comprising ethylene glycol (e.g., 2-mercaptoethylether).

PTK polymers can be synthesized from any number of combinations of precursor compounds (subunits). Precursors include known dithiol monomers. Notably, some PTK and ethylene glycol copolymers are synthesized from a precursor comprising one or more ethylene glycol units, which may or may not be repeating (e.g., poly(ethylene glycol) dithiols). Some PTK polymers are synthesized using precursors comprising one or more thiol groups, such as precursors that are a dithiol or, more specifically, a dithiol functional oligo-ethelyne glycol. In some embodiments a precursor can comprise one or more ketal groups. In some embodiments the precursor used to synthesize the PEG-PTK copolymer is a dithiol selected from the group consisting of 2-mercaptoethyl ether (di(ethylene glycol) dithiol), 2,2'-(ethylenedioxy)diethanethiol (tri(ethylene glycol) dithiol), 2,2'[2,2'-oxybis(ethane-2,1-diyl)bis(oxy)]diethanethiol (tetra(ethylene glycol) dithiol), 3,6,9,12,15-pentaoxaheptadecane-1,17-dithiol,tetraethylene glycol di(ethanediol)(hexa(ethylene glycol) dithiol). Of course, by varying the types and proportions of precursors utilized, desired mechanical and degradation characteristics can be obtained.

Degradation properties can be tuned by, among other things, using precursors to modify the distance between thioketal linkers in a polythioketal polymers. In other embodiments degradation can be tuned by varying the concentration of other groups in the PTK polymer and/or polyisocyanate. For example, scaffolds can degrade at a faster rate as the concentration of ether groups in the PTK polymer increases. Thus, the inclusion of poly(ethylene glycol) dithiols to a PTK polymer can increase the relatively degradation rate of the resulting PTK-UR scaffold.

In this regard, in some embodiments the present scaffolds comprise a PTK polymer that includes a poly(ethylene glycol) dithiol (e.g., di(ethylene glycol) dithiol) and another dithiol. The other dithiol can be an alkane dithiol. The alkane dithiol can have any suitable number of carbon atoms, and in some embodiments comprises 1 to 10 carbon atoms. An exemplary alkane dithiol includes 1,4-butanedithiol. Nevertheless, for PTK polymer comprise a di(ethylene glycol) dithiol and another dithiol, the molecular ratio of the di(ethylene glycol) dithiol to the other dithiol can be 100:0 (no other dithiol) to 0:100 (no di(ethylene glycol) dithiol). Thus, the resulting PTK polymer can comprise about 5, 10, 15, 20, 25, 30, 40, 45, 50, 55, 60, 65. 70, 75, 80, 85, 90, or 95 mol % of the di(ethylene glycol) dithiol.

Furthermore, some embodiments the PTK polymers can have their functional groups modified. In specific embodiments the terminal functional groups, or the function groups at opposite ends of a polymer backbone and/or branch, have modified functional groups. For example, in some embodiments the end-groups of the PTK polymer can be modified with hydroxyl or amine functional groups, rather than the sulfhydryl groups that result from the synthesis of a PTK polymer. In some embodiments the PTK polymers comprising terminal —NH groups, including nonfunctionalized PTK polymers, have relatively higher reactivities than PTK polymers having hydroxyl terminal groups. Accordingly, in some embodiments comprising thiol terminal groups can utilize 0.001-5 pphp catalyst (e.g., triethylene diamine (TEDA)) and preferably 0.001-2 pphp TEDA, whereas embodiments comprising hydroxyl terminal groups can utilize 0.1-10 pphp TEDA and preferably 0.5-5 pphp. This different reactivity is caused by, among other things, what is known in the art as "click" chemistry. Please see Shin, et al., "Thiol-Isocyanate-Ene Ternary Networks by Sequential and Simultaneous Thiol Click Reactions," *Chemistry of Materials*, (2010) 22, 2616-2625 for a discussion regarding click chemistry in thiol-terminated polymers.

In specific embodiments the polythioketal polymers include the formula:

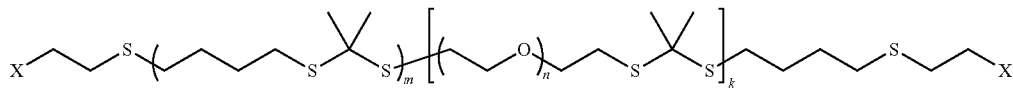

wherein n is about 1, 2, 3, 4, 5, 6, 7, 8, 9, 10, 11, or 12, m is about 0, 1, 2, 3, 4, or 5, k is about 0, 1, 2, 3, 4, or 5, X is hydroxyl, thiol, amine, or a combination thereof.

As discussed more in detail below, embodiments of scaffolds, including PTK scaffolds, can optionally comprise one or more of a catalyst, water, a stabilizer, or a pore opener. In some embodiments the catalyst comprises one or more amines, including, for example, a solution of triethylene diamine in dipropyleneglycol. In some embodiments the stabilizer is sulfated caster oil (Turkey red oil), and in some embodiments the pore opener can be calcium stearate.

These components can be added to the scaffold in any amount to achieve desired properties in the scaffold. In some embodiments the pore opener, catalyst and/or stabilizer are added so as to achieve about 0-10 parts per hundred parts polyol (pphp) of each component.

Furthermore, and as discussed herein, any isocyanate can be used in the synthesis of biodegradable scaffolds. For example, embodiments of scaffolds that comprise a PTK polymer comprise LTI or HDIt.

By manipulating the polyisocyanate and polythioketal polymer utilized to form a PTK-UR scaffold, the degradation characteristics of the scaffold can be optimized. The degradation can be further optimized by functionalizing the PTK polymer with functional groups such as hydroxyl and amine groups. Further still, degradation can be affected by varying the precursors (subunits) used to synthesize the PTK polymer, which, among other things, can change the distance between thioketal units in the PTK polymer.

Thioketal. In some embodiments, the polyisocyanate is combined with a hydroxyl end functional TK to formulate the poly(thioketal urethane) (PTKUR). The thioketal includes any hydroxyl end functional thioketal with a functionality of 2 or more, including, but not limited to, thioketal diols and/or thioketal triols. In one embodiment, the TKs are low molecular weight TK. As used herein, the term "low molecular weight" refers to compounds having an equivalent weight (i.e., molecular weight/functionality) of less than 500 grams/equivalent (g/eq), between 25 and 500 g/eq, less than 300 g/eq, between 25 and 300 g/eq, less than 150 g/eq, between 25 and 150 g/eq, between 50 and 150 g/eq, between 75 and 150 g/eq, between 90 and 150 g/eq, or any combination, sub-combination, range, or sub-range thereof. In another embodiment, the TK includes an equivalent weight of between 75 and 125 g/eq, such as, but not limited to, an equivalent weight of about 100 g/eq. In a further embodiment, for example, TK includes the formula:

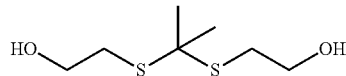

In certain embodiments, synthesizing the hydroxyl end functional TK includes reacting thioglycolic acid with a methoxy functional molecule to form a carboxyl end functional intermediate, followed by reduction of the carboxyl end functional intermediate with any suitable reducing agent, such as lithium aluminum hydride, to form a hydroxyl functional TK. For example, as shown below in Scheme 2, one method of synthesizing a low molecular weight TK diol includes reaction of thioglycolic acid and 2,2-dimethoxypropane to form a carboxyl-terminated TK, followed by reduction with lithium aluminum hydride to form the hydroxyl-terminated TK diol.

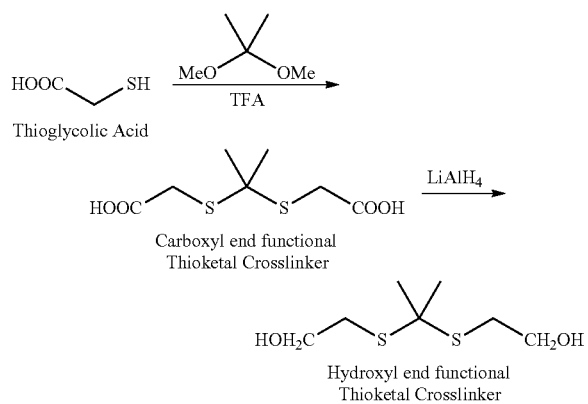

In another example, as shown below in Scheme 3, one method for synthesizing a low molecular weight TK triol includes reaction of thioglycolic acid with 1,1,1-trimethoxypentane to form a carboxyl-terminated TK, followed by reduction with lithium aluminum hydride to form the hydroxyl-terminated TK triol.

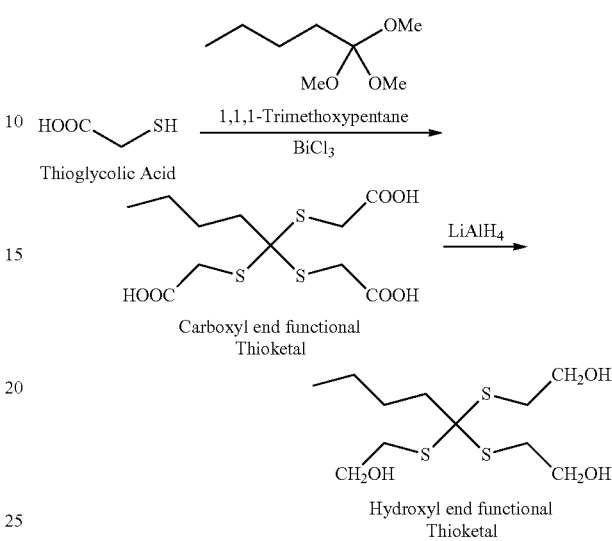

Although not described in the examples above, as will be appreciated by those of ordinary skill in the art, the step of reacting thioglycolic acid with a methoxy functional molecule may be catalyzed by bismuth(III) chloride or any other suitable catalyst.

According to one or more of the embodiments described herein, the PTKUR formed with the hydroxyl end functional TK provides a bone cement that is hydrolytically stable and degradable by cell-secreted ROS. For example, in some embodiments, the hydroxyl end functional TK provides a crosslinker that is selectively degraded by reactive oxygen species generated by cells during bone healing. Additionally, as compared to PTKUR foams synthesized from a 1000 g mol$^{-1}$ TK macrodiol, the PTKUR formed from the low molecular weight TK diol provides increased bone-like strength and number of degradable units.

As discussed in detail below, the scaffold comprising PTK polymers and/or hydroxyl end functional TKs can also be used to deliver one or more additional components, including bioactive agents, to a particular site.

Additional Components. In accordance with the present invention, two-component compositions (i.e., polyisocyanates and poly(thioketal) polymers) to form porous composites may be used with other agents and/or catalysts. Zhang et al. have found that water may be an adequate blowing agent for a lysine diisocyanate/PEG/glycerol polyurethane (see Zhang, et al., *Tissue Eng.* 2003 (6):1143-57) and may also be used to form porous structures in polyurethanes. Other blowing agents include dry ice or other agents that release carbon dioxide or other gases into the composite. Alternatively, or in addition, porogens (see detail discussion below) such as salts may be mixed in with reagents and then dissolved after polymerization to leave behind small voids.

Two-component compositions and/or the prepared composites used in the present invention may include one or more additional components. In some embodiments, inventive compositions and/or composites may include, water, a catalyst (e.g., gelling catalyst, blowing catalyst, etc.), a stabilizer, a plasticizer, a porogen, a chain extender (for making of polyurethanes), a pore opener (such as calcium stearate, to control pore morphology), a wetting or lubricating agent, etc. (See, U.S. Ser. No. 10/759,904 published under No. 2005-0013793, and U.S. Ser. No. 11/625,119 published under No. 2007-0191963; both of which are incorporated herein by reference).

In some embodiments, inventive compositions and/or composites may include and/or be combined with a solid filler (e.g., carboxymethylcellulose (CMC), hyaluronic acid (HA), bone). For example, when composites used in wound healing, solid fillers can help absorb excess moisture in the wounds from blood and serum and allow for proper foaming.

Other additional components include, but are not limited to, osteoconductivity enhancers. Suitable osteoconductivity enhancers may include ceramics, hydroxyapatite, pharmaceutically acceptable salts thereof, pharmaceutically acceptable derivatives thereof, or a combination thereof. For example, in one embodiment, 85% β-tricalcium phosphate (β-TCP)/15% hydroxyapatite (HA) ceramic mini-granules (MASTERGRAFT®, MG) is combined with hydroxyl end functional TK and polyisocyanate to form the PTKUR with increased osteoconductivity. In another embodiment, nanocrystalline hydroxyapatite is combined with hydroxyl end functional TK and polyisocyanate to form the PTKUR with increased osteoconductivity.

In certain embodiments, additional biocompatible polymers (e.g., PEG) or copolymers can be used with compositions and composites in the present invention.

Water. Water may be a blowing agent to generate porous polyurethane-based composites. Porosity of bone/polymer composites increased with increasing water content, and biodegradation rate accelerated with decreasing polyester half-life, thereby yielding a family of materials with tunable properties that are useful in the present invention. See, Guelcher et al., Tissue Engineering, 13(9), 2007, pp 2321-2333, which is incorporated by reference.

In some embodiments, an amount of water is about 0.5, 1, 1.5, 2, 3, 4 5, 6, 7, 8, 9, 10 parts per hundred parts (pphp) polyol. In some embodiments, water has an approximate range of any of such amounts.

In some embodiments, at least one catalyst is added to form reactive liquid mixture (i.e., two-component compositions). A catalyst, for example, can be non-toxic (in a concentration that may remain in the polymer).

Catalyst. A catalyst can, for example, be present in two-component compositions in a concentration in the range of approximately 0.5 to 5 parts per hundred parts polyol (pphp) and, for example, in the range of approximately 0.5 to 2, or 2 to 3 pphp. A catalyst can, for example, be an amine compound. In some embodiments, catalyst may be an organometallic compound or a tertiary amine compound. In some embodiments the catalyst may be stannous octoate (an organobismuth compound), triethylene diamine optionally in solution with dipropyleneglycol, bis(dimethylaminoethyl) ether, dimethylethanolamine, dibutyltin dilaurate, and Coscat organometallic catalysts manufactured by Vertullus (a bismuth based catalyst), or any combination thereof. In some embodiments, the catalyst includes FeAA. For example, the catalyst may include a 5% solution of FeAA with e-cap dissolved directly into TK.

Stabilizer. In some embodiments, a stabilizer is nontoxic (in a concentration remaining in the polyurethane foam) and can include a non-ionic surfactant, an anionic surfactant or combinations thereof. For example, a stabilizer can be a polyethersiloxane, a salt of a fatty sulfonic acid or a salt of a fatty acid. In certain embodiments, a stabilizer is a polyethersiloxane, and the concentration of polyethersiloxane in a reactive liquid mixture can, for example, be in the range of approximately 0.25 to 4 parts per hundred polyol. In some embodiments, polyethersiloxane stabilizer is hydrolyzable.

In some embodiments, the stabilizer can be a salt of a fatty sulfonic acid. Concentration of a salt of the fatty sulfonic acid in a reactive liquid mixture can be in the range of approximately 0.5 to 5 parts per hundred polyol. Examples of suitable stabilizers include a sulfated castor oil or sodium ricinoleicsulfonate.

Stabilizers can be added to a reactive liquid mixture of the present invention to, for example, disperse prepolymers, polyols and other additional components, stabilize the rising carbon dioxide bubbles, and/or control pore sizes of inventive composites. Although there has been a great deal of study of stabilizers, the operation of stabilizers during foaming is not completely understood. Without limitation to any mechanism of operation, it is believed that stabilizers preserve the thermodynamically unstable state of a polyurethane foam during the time of rising by surface forces until the foam is hardened. In that regard, foam stabilizers lower the surface tension of the mixture of starting materials and operate as emulsifiers for the system. Stabilizers, catalysts and other polyurethane reaction components are discussed, for example, in Oertel, Günter, ed., *Polyurethane Handbook*, Hanser Gardner Publications, Inc. Cincinnati, Ohio, 99-108 (1994). A specific effect of stabilizers is believed to be the formation of surfactant monolayers at the interface of higher viscosity of bulk phase, thereby increasing the elasticity of surface and stabilizing expanding foam bubbles.

Chain Extender. To prepare high-molecular-weight polymers, prepolymers are chain extended by adding a short-chain (e.g., <500 g/mol) polyamine or polyol. In certain embodiments, water may act as a chain extender. In some embodiments, addition of chain extenders with a functionality of two (e.g., diols and diamines) yields linear alternating block copolymers.

Plasticizer. In some embodiments, inventive compositions and/or composites include one or more plasticizers. Plasticizers are typically compounds added to polymers or plastics to soften them or make them more pliable. According to the present invention, plasticizers soften, make workable, or otherwise improve the handling properties of polymers or composites. Plasticizers also allow inventive composites to be moldable at a lower temperature, thereby avoiding heat induced tissue necrosis during implantation. Plasticizer may evaporate or otherwise diffuse out of the composite over time, thereby allowing composites to harden or set. Without being bound to any theory, plasticizer are thought to work by embedding themselves between the chains of polymers. This forces polymer chains apart and thus lowers the glass transition temperature of polymers. In general, the more plasticizer added, the more flexible the resulting polymers or composites will be.

In some embodiments, plasticizers are based on an ester of a polycarboxylic acid with linear or branched aliphatic alcohols of moderate chain length. For example, some plasticizers are adipate-based. Examples of adipate-based plasticizers include bis(2-ethylhexyl)adipate (DOA), dimethyl adipate (DMAD), monomethyl adipate (MMAD), and dioctyl adipate (DOA). Other plasticizers are based on maleates, sebacates, or citrates such as bibutyl maleate (DBM), diisobutylmaleate (DIBM), dibutyl sebacate (DBS), triethyl citrate (TEC), acetyl triethyl citrate (ATEC), tributyl citrate (TBC), acetyl tributyl citrate (ATBC), trihexyl citrate (TOC), acetyl trioctyl citrate (ATOC), trihexyl citrate (THC), acetyl trihexyl citrate (ATHC), butyryl trihexyl citrate (BTHC), and trimethylcitrate (TMC). Other plasticizers are phthalate based. Examples of phthalate-based plasticizers are N-methyl phthalate, bis(2-ethylhexyl) phthalate (DEHP), diisononyl phthalate (DINP), bis(n-butyl) phthalate (DBP), butyl benzyl phthalate (BBzP), diisodecyl phthalate (DOP), diethyl phthalate (DEP), diisobutyl phthalate (DIBP), and di-n-hexyl phthalate. Other suitable plasticizers include liquid polyhydroxy compounds such as glycerol, polyethylene glycol (PEG), triethylene glycol, sorbitol, monacetin, diacetin, and mixtures thereof. Other plasticizers include trimellitates (e.g., trimethyl trimellitate (TMTM), tri-(2-ethylhexyl) trimellitate (TEHTM-MG), tri-(n-octyl,n-decyl) trimellitate (ATM), tri-(heptyl,nonyl) trimellitate (LTM), n-octyl trimellitate (OTM)), benzoates, epoxidized vegetable oils, sulfonamides (e.g., N-ethyl toluene sulfonamide (ETSA), N-(2-hydroxypropyl) benzene sulfonamide (HP BSA), N-(n-butyl) butyl sulfonamide (BBSA-NBBS)), organophosphates (e.g., tricresyl phosphate (TCP), tributyl phosphate (TBP)), glycols/polyethers (e.g., triethylene glycol dihexanoate, tetraethylene glycol diheptanoate), and polymeric plasticizers. Other plasticizers are described in *Handbook of Plasticizers* (G. Wypych, Ed., ChemTec Publishing, 2004), which is incorporated herein by reference. In certain embodiments, other polymers are added to the composite as plasticizers. In certain particular embodiments, polymers with the same chemical structure as those used in the composite are used but with lower molecular weights to soften the overall composite. In other embodiments, different polymers with lower melting points and/or lower viscosities than those of the polymer component of the composite are used.

In some embodiments, polymers used as plasticizer are poly(ethylene glycol) (PEG). PEG used as a plasticizer is typically a low molecular weight PEG such as those having an average molecular weight of 1000 to 10000 g/mol, for example, from 4000 to 8000 g/mol. In certain embodiments, PEG 4000, PEG 5000, PEG 6000, PEG 7000, PEG 8000 or combinations thereof are used in inventive composites. For example, plasticizer (PEG) is useful in making more moldable composites that include poly(lactide), poly(D,L-lactide), poly(lactide-co-glycolide), poly(D,L-lactide-co-glycolide), or poly(caprolactone). Plasticizer may comprise 1-40% of inventive composites by weight. In some embodiments, the plasticizer is 10-30% by weight. In some embodiments, the plasticizer is approximately 10%, 15%, 20%, 25%, 30% or 40% by weight. In other embodiments, a plasticizer is not used in the composite. For example, in some polycaprolactone-containing composites, a plasticizer is not used.

In some embodiments, inert plasticizers may be used. In some embodiments, a plasticizer may not be used in the present invention.

Porosity of inventive composites may be accomplished using any means known in the art. Exemplary methods of creating porosity in a composite include, but are not limited to, particular leaching processes, gas foaming processing, supercritical carbon dioxide processing, sintering, phase transformation, freeze-drying, cross-linking, molding, porogen melting, polymerization, melt-blowing, and salt fusion (Murphy et al., *Tissue Engineering* 8(1):43-52, 2002; incorporated herein by reference). For a review, see Karageorgiou et al., *Biomaterials* 26:5474-5491, 2005; incorporated herein by reference. Porosity may be a feature of inventive composites during manufacture or before implantation, or porosity may only be available after implantation. For example, an implanted composite may include latent pores. These latent pores may arise from including porogens in the composite.

Porogens may be any chemical compound that will reserve a space within the composite while the composite is being molded and will diffuse, dissolve, and/or degrade prior to or after implantation or injection leaving a pore in the composite. Porogens may have the property of not being appreciably changed in shape and/or size during the procedure to make the composite moldable. For example, a porogen should retain its shape during the heating of the composite to make it moldable. Therefore, a porogen does not melt upon heating of the composite to make it moldable. In certain embodiments, a porogen has a melting point greater than about 60° C., greater than about 70° C., greater than about 80° C., greater than about 85° C., or greater than about 90° C.

Porogens may be of any shape or size. A porogen may be spheroidal, cuboidal, rectangular, elongated, tubular, fibrous, disc-shaped, platelet-shaped, polygonal, etc. In certain embodiments, the porogen is granular with a diameter ranging from approximately 100 microns to approximately 800 microns. In certain embodiments, a porogen is elongated, tubular, or fibrous. Such porogens provide increased connectivity of pores of inventive composite and/or also allow for a lesser percentage of the porogen in the composite.

Amount of porogens may vary in inventive composite from 1% to 80% by weight. In certain embodiments, the plasticizer makes up from about 5% to about 80% by weight of the composite. In certain embodiments, a plasticizer makes up from about 10% to about 50% by weight of the composite. Pores in inventive composites are thought to improve the osteoinductivity or osteoconductivity of the composite by providing holes for cells such as osteoblasts, osteoclasts, fibroblasts, cells of the osteoblast lineage, stem cells, etc. Pores provide inventive composites with biological in growth capacity. Pores may also provide for easier degradation of inventive composites as bone is formed and/or remodeled. In some embodiments, a porogen is biocompatible.

A porogen may be a gas, liquid, or solid. Exemplary gases that may act as porogens include carbon dioxide, nitrogen, argon, or air. Exemplary liquids include water, organic solvents, or biological fluids (e.g., blood, lymph, plasma). Gaseous or liquid porogen may diffuse out of the osteoimplant before or after implantation thereby providing pores for biological in-growth. Solid porogens may be crystalline or amorphous. Examples of possible solid porogens include water soluble compounds. Exemplary porogens include carbohydrates (e.g., sorbitol, dextran (poly(dextrose)), starch), salts, sugar alcohols, natural polymers, synthetic polymers, and small molecules.

In some embodiments, carbohydrates are used as porogens in inventive composites. A carbohydrate may be a monosaccharide, disaccharide, or polysaccharide. The carbohydrate may be a natural or synthetic carbohydrate. In some embodiments, the carbohydrate is a biocompatible, biodegradable carbohydrate. In certain embodiments, the carbohydrate is a polysaccharide. Exemplary polysaccharides include cellulose, starch, amylose, dextran, poly(dextrose), glycogen, etc.

In certain embodiments, a polysaccharide is dextran. Very high molecular weight dextran has been found particularly useful as a porogen. For example, the molecular weight of the dextran may range from about 500,000 g/mol to about 10,000,000 g/mol, preferably from about 1,000,000 g/mol to about 3,000,000 g/mol. In certain embodiments, the dextran has a molecular weight of approximately 2,000,000 g/mol. Dextrans with a molecular weight higher than 10,000,000 g/mol may also be used as porogens. Dextran may be used in any form (e.g., particles, granules, fibers, elongated fibers) as a porogen. In certain embodiments, fibers or elongated fibers of dextran are used as a porogen in inventive composites. Fibers of dextran may be formed using any known method including extrusion and precipitation. Fibers may be prepared by precipitation by adding an aqueous solution of dextran (e.g., 5-25% dextran) to a less polar solvent such as a 90-100% alcohol (e.g., ethanol) solution. The dextran precipitates out in fibers that are particularly useful as porogens in the inventive composite. Once the composite with dextran as a porogen is implanted into a subject, the dextran dissolves away very quickly. Within approximately 24 hours, substantially all of dextran is out of composites leaving behind pores in the osteoimplant composite. An advantage of using dextran in a composite is that dextran exhibits a hemostatic property in extravascular space. Therefore, dextran in a composite can decrease bleeding at or near the site of implantation.

Small molecules including pharmaceutical agents may also be used as porogens in the inventive composites. Examples of polymers that may be used as plasticizers include poly(vinyl pyrollidone), pullulan, poly(glycolide), poly(lactide), and poly(lactide-co-glycolide). Typically low molecular weight polymers are used as porogens. In certain embodiments, a porogen is poly(vinyl pyrrolidone) or a derivative thereof. Plasticizers that are removed faster than the surrounding composite can also be considered porogens.

II) Components to Deliver

Alternatively or additionally, composites of the present invention may have one or more components to deliver when implanted, including biomolecules, small molecules, bioactive agents, cells, etc., to promote tissue regeneration, growth, and healing. Examples of materials that can be incorporated include chemotactic factors, angiogenic factors, bone cell inducers and stimulators, including the general class of cytokines such as the TGF-□ superfamily of bone growth factors, the family of bone morphogenic proteins, osteoinductors, and/or bone marrow or bone forming precursor cells, isolated using standard techniques. Sources and amounts of such materials that can be included are known to those skilled in the art.

Biologically active materials, comprising biomolecules, small molecules, and bioactive agents may also be included in inventive composites to, for example, stimulate particular metabolic functions, recruit cells, or reduce inflammation. For example, nucleic acid vectors, including plasmids and viral vectors, that will be introduced into the patient's cells and cause the production of growth factors such as bone morphogenetic proteins may be included in a composite. Biologically active agents include, but are not limited to, antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, antirejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxyapatite, and penetraction enhancer. Additional exemplary substances include chemotactic factors, angiogenic factors, analgesics, antibiotics, anti-inflammatory agents, bone morphogenic proteins, and other growth factors that promote cell-directed degradation or remodeling of the polymer phase of the composite and/or development of new tissue (e.g., bone). RNAi or other technologies may also be used to reduce the production of various factors.

In some embodiments, inventive composites include antibiotics. Antibiotics may be bacteriocidial or bacteriostatic. An anti-microbial agent may be included in composites. For example, anti-viral agents, anti-protazoal agents, anti-parasitic agents, etc. may be included in composites. Other suitable biostatic/biocidal agents include antibiotics, povidone, sugars, and mixtures thereof. Exemplary antibiotics include, but not limit to, Amikacin, Gentamicin, Kanamycin, Neomycin, Netilmicin, Streptomycin, Tobramycin, Paromomycin, Geldanamycin, Herbimycin, Loravabef, etc. (See, *The Merck Manual of Medical Information—Home Edition*, 1999).

Inventive composites may also be seeded with cells. In some embodiments, a patient's own cells are obtained and used in inventive composites. Certain types of cells (e.g., osteoblasts, fibroblasts, stem cells, cells of the osteoblast lineage, etc.) may be selected for use in the composite. Cells may be harvested from marrow, blood, fat, bone, muscle, connective tissue, skin, or other tissues or organs. In some embodiments, a patient's own cells may be harvested, optionally selected, expanded, and used in the inventive composite. In other embodiments, a patient's cells may be harvested, selected without expansion, and used in the inventive composite. Alternatively, exogenous cells may be employed. Exemplary cells for use with the invention include mesenchymal stem cells and connective tissue cells, including osteoblasts, osteoclasts, fibroblasts, preosteoblasts, and partially differentiated cells of the osteoblast lineage. Cells may be genetically engineered. For example, cells may be engineered to produce a bone morphogenic protein.

In some embodiments, inventive composites may include a composite material comprising a component to deliver. For example, a composite material can be a biomolecule (e.g., a protein) encapsulated in a polymeric microsphere or nanoparticles. In certain embodiments, BMP-2 encapsulated in PLGA microspheres may be embedded in a bone/polyurethane composite used in accordance with the present invention. Sustained release of BMP-2 can be achieved due to the diffusional barriers presented by both the PLGA and Polyurethane of the inventive composite. Thus, release kinetics of growth factors (e.g., BMP-2) can be tuned by varying size of PLGA microspheres and porosity of polyurethane composite.

To enhance biodegradation in vivo, composites of the present invention can also include different enzymes. Examples of suitable enzymes or similar reagents are proteases or hydrolases with ester-hydrolyzing capabilities. Such enzymes include, but are not limited to, proteinase K, bromelaine, pronase E, cellulase, dextranase, elastase, plasmin streptokinase, trypsin, chymotrypsin, papain, chymopapain, collagenase, subtilisin, chlostridopeptidase A, ficin, carboxypeptidase A, pectinase, pectinesterase, an oxireductase, an oxidase, or the like. The inclusion of an appropriate amount of such a degradation enhancing agent can be used to regulate implant duration.

Components to deliver may not be covalently bonded to a component of the composite. In some embodiments, components may be selectively distributed on or near the surface of inventive composites using the layering techniques described above. While surface of inventive composite will be mixed somewhat as the composite is manipulated in implant site, thickness of the surface layer will ensure that at least a portion of the surface layer of the composite remains at surface of the implant. Alternatively or in addition, biologically active components may be covalently linked to the bone particles before combination with the polymer. As discussed above, for example, silane coupling agents having amine, carboxyl, hydroxyl, or mercapto groups may be attached to the bone particles through the silane and then to reactive groups on a biomolecule, small molecule, or bioactive agent.

III) Preparation of Scaffold

In general, inventive scaffolds are prepared by combining hydroxyl end functional thioketals, one or more polymers, compounds, particles, and/or any additional components. For example, in one embodiment, forming inventive scaffolds includes combining a poly(thioketal) polymer and a polyisocyanate, as discussed herein, with a reactive liquid (i.e., a two-component composition) thereby forming a naturally injectable or moldable scaffold or a scaffold that can be made injectable or moldable. In another embodiment, forming inventive scaffolds includes combining a hydroxyl end functional TK with an excess of isocyanate to form a quasi-prepolymer, combining the quasi-prepolymer and additional hydroxyl end functional TK, and then adding a catalyst to catalyze the reaction between the quasi-prepolymer and the hydroxyl end functional TK. Suitable catalysts include, but are not limited to, a low-toxicity iron (III) acetylacetonate gelling catalyst. If present, the compounds, particles, and/or additional components, including any components to be delivered, may be combined with the polyisocyanate, hydroxyl end functional TK, and/or PTK polymer at any point during the formation of the scaffold, including, but not limited to, before, during, or after the combining of the polyisocyanate with the poly(thioketal) polymer and/or the hydroxyl end functional TK.

In some embodiments, particles may be combined first with a hardener that includes a PTK polymer and, optionally, one or more of water, a catalyst, a solvent, a diluent, a stabilizer, a porogen, a plasticizer, etc., and then the hardener is combined with a polyisocyanate. In some embodiments, a hardener (e.g., a PTK polymer, water and a catalyst) may be mixed with components to be delivered (e.g., biologically active agents) or components that are to be incorporated into the scaffold (e.g., porogens, bone powder, etc.). In some embodiments, in order to enhance storage stability of two-component compositions, the two (liquid) component process may be modified to an alternative three (liquid)-component process wherein a catalyst and water may be dissolved in a solution separating from reactive PTK polymers. For example, PTK polymers may be first mixed with a solution of a catalyst and water, followed by addition of polyisocynates. The polyisocyanates described herein include various NCO-terminated compounds.

In some embodiments, additional components or components to be delivered may be combined with a reactive liquid prior to injection. In some embodiments, they may be combined with one of precursors (i.e., polyisocyanate, hydroxyl end functional TK, and PTK polymers) prior to mixing the precursors in forming of a reactive liquid/paste.

Porous scaffolds can be prepared by incorporating a small amount (e.g., <5 wt %) of water which reacts with prepolymers to form carbon dioxide, a biocompatible blowing agent. Resulting reactive liquid/paste may be injectable through a 12-ga syringe needle or the like into molds or targeted site to set in situ. In some embodiments, gel time is great than 3 min, 4 min, 5 min, 6 min, 7 min, or 8 min. In some embodiments, cure time is less than 20 min, 18 min, 16 min, 14 min, 12 min, or 10 min.

In some embodiments, catalysts can be used to assist forming porous composites. In general, the more blowing catalyst used, the high porosity of inventive composites may be achieved The precursors may be combined by any method known to those skilled in the art. For example, a homogenous mixture of precursors (e.g., PTK polymer, polyisocyanate, etc.) and particles may be pressed together at ambient or elevated temperatures. At elevated temperatures, a process may also be accomplished without pressure. In some embodiments, precursors are not held at a temperature of greater than approximately 60° C. for a significant time during mixing to prevent thermal damage to any biological component (e.g., growth factors or cells) of a scaffold. In some embodiments, temperature is not a concern because precursors used in the present invention have a low reaction exotherm.

Alternatively or in addition, components may be mixed or folded into a scaffold softened by heat or a solvent. Alternatively, a moldable scaffold may be formed into a sheet that is then covered with a layer of components to be delivered and or carried in the scaffold. Such components may then be forced into the scaffold sheet using pressure. In another embodiment, components are individually coated with scaffolds or scaffold precursors, for example, using a tumbler, spray coater, or a fluidized bed, before being mixed with a larger quantity of polymer. This facilitates even coating of the particles and improves integration of the particles and polymer component of the scaffold.

Polymers (e.g., polyisocyanate, PTK polymers, combinations thereof) may be further modified by further cross-linking or polymerization to form a scaffold in which the polymer is covalently linked to the incorporated components.

In some embodiments, an inventive scaffold is produced with an injectable composition and then set in situ. For example, cross-link density of a low molecular weight polymer may be increased by exposing it to electromagnetic radiation (e.g., UV light) or an alternative energy source. Alternatively or additionally, a photoactive cross-linking agent, chemical cross-linking agent, additional monomer, or combinations thereof may be mixed into inventive composites. Exposure to UV light after a composition is injected into an implant site will increase one or both of molecular weight and cross-link density, stiffening polymers (i.e., polyurethanes) and thereby a composite. Polymer components of inventive scaffold used in the present invention may be softened by a solvent, e.g., ethanol.

In some embodiments, it may be desirable to infiltrate a polymer or polymer precursor into vascular and/or interstitial structure of bone particles or into bone-derived tissues. Vascular structure of bone includes such structures such as osteocyte lacunae, Haversian canals, Volksmann's canals, canaliculi and similar structures. Interstitial structure of bone particles includes spaces between trabeculae and similar features. Many of monomers and precursors (e.g., polyisocyanate, PTK polymers and subunits thereof) suggested for use with the invention are sufficiently flowable to penetrate through the channels and pores of trabecular bone. Some may even penetrate into trabeculae or into mineralized fibrils of cortical bone. Thus, it may be necessary to incubate bone particles in precursors for a period of time to accomplish infiltration. In certain embodiments, the scaffold as a reactive mixture is itself sufficiently flowable that it can penetrate channels and pores of bone. In certain embodiments, scaffolds may also be heated or combined with a solvent to make it more flowable for this purpose. Other ceramic materials and/or other bone-substitute materials employed as a particulate phase may also include porosity that can be infiltrated as described herein.

Inventive scaffolds of the present invention can exhibit high degrees of porosity over a wide range of effective pore sizes. Thus, scaffolds may have, at once, macroporosity, mesoporosity and microporosity. Macroporosity is characterized by pore diameters greater than about 100 microns. Mesoporosity is characterized by pore diameters between about 100 microns about 10 microns; and microporosity occurs when pores have diameters below about 10 microns. In some embodiments, the scaffold has a porosity of at least about 30%. For example, in certain embodiments, the scaffold has a porosity of more than about 50%, more than about 60%, more than about 70%, more than about 80%, or more than about 90%. In some embodiments, inventive scaffolds have a porosity in a range of about 10%-20%, 20%-30%, 30%-40%, 40%-50%, 50%-60%, 60%-70%, 70%-80%, 80%-90%, or 90%-99%. Advantages of a porous scaffold over non-porous scaffold include, but are not limited to, more extensive cellular and tissue in-growth into the composite, more continuous supply of nutrients, more thorough infiltration of therapeutics, and enhanced revascularization, allowing tissue growth and repair to take place more efficiently. Furthermore, in certain embodiments, the porosity of the scaffold may be used to load the scaffold with biologically active agents such as drugs, small molecules, cells, cells that are encapsulated in, for example, gel beads, peptides, polynucleotides, growth factors, osteogenic factors, etc, for delivery at the implant site. Porosity may also render certain composites of the present invention compressible.

In some embodiments, pores of inventive scaffolds may be over 100 microns wide for the invasion of cells and bony in-growth (Klaitwatter et al., *J. Biomed. Mater. Res. Symp.* 2:161, 1971; which is incorporated herein by reference). In certain embodiments, the pore size may be in a range of approximately 50 microns to approximately 750 microns, for example, of approximately 100 microns to approximately 500 microns.

After implantation, inventive composites are allowed to remain at the site and can provide the strength desired and promote healing of the tissue and/or tissue growth. The scaffolds may be degraded or be resorbed as new tissue is formed at the implantation site. Polymer may be resorbed over approximately 1 week to approximately 1 year. Scaffolds may start to be remodeled in as little as a week as the composite is infiltrated with cells or new bone in-growth. A remodeling process may continue for weeks, months, or years. For example, scaffolds used in accordance with the present invention may be resorbed within about 4-8 weeks, 2-6 months, or 6-12 months. A degradation rate is defined as the mass loss as a function of time, and it can be measured by immersing the sample in phosphate buffered saline or medium and measuring the sample mass as a function of time.

One skilled in the art will recognize that standard experimental techniques may be used to test these properties for a range of compositions to optimize a composite for a desired application.

IV) Use and Application of Composite

As discussed above, polymers or polymer precursors, and other components may be supplied separately, e.g., in a kit, and mixed immediately prior to implantation, injection or molding. A surgeon or other health care professional may also combine components in a kit with autologous tissue derived during surgery or biopsy. For example, a surgeon may want to include autogenous tissue or cells, e.g., bone marrow or bone shavings generated while preparing an implant site, into a composite (see more details in co-owned U.S. Pat. No. 7,291,345 and U.S. Ser. No. 11/625,119 published under No. 2007-0191963; both of which are incorporated herein by reference).

In some embodiments a method for treating tissue in a subject in need thereof is provided. The method can comprise providing a biodegradable scaffold, including on that includes a polythioketal polymer and a polyisocyanate, and then contacting the tissue with the scaffold. In some embodiments the tissue is wound site. More specifically, in some embodiments the tissue can be bone, skin, or the like.

Scaffolds of the present invention may be used in a wide variety of clinical applications. A method of preparing and using scaffolds for orthopedic applications utilized may include the steps of providing a curable scaffolds composition (e.g., reactive mixture), mixing parts of a composition, and curing a composition in a tissue site wherein a composition is sufficiently flowable to permit injection by minimally invasive techniques. In some embodiments, a flowable composition to inject may be pressed by hand or machine. In some embodiments, a moldable composition may be pre-molded and implanted into a target site. Injectable or moldable compositions utilized in the present invention may be processed (e.g., mixed, pressed, molded, etc.) by hand or machine.

Inventive scaffolds and/or compositions may be used as injectable materials with or without exhibiting high mechanical strength (i.e., load-bearing or non-load bearing, respectively). In some embodiments, inventive scaffolds and/or compositions may be used as moldable materials. For example, compositions (e.g., PTK polymer, monomers, reactive liquids/pastes, polymers, bone particles, additional components, etc.) in the present invention can be pre-molded into predetermined shapes. Upon implantation, the pre-molded composite may further cure in situ and provide mechanical strength (i.e., load-bearing). A few examples of potential applications are discussed in more detail below.

In some embodiments, compositions and/or scaffolds may be used as a bone void filler. Bone fractures and defects, which result from trauma, injury, infection, malignancy or developmental malformation can be difficult to heal in certain circumstances. If a defect or gap is larger than a certain critical size, natural bone is unable to bridge or fill the defect or gap. These are several deficiencies that may be associated with the presence of a void in a bone. Bone void may compromise mechanical integrity of bone, making bone potentially susceptible to fracture until void becomes ingrown with native bone. Accordingly, it is of interest to fill such voids with a substance which helps voids to eventually fill with naturally grown bone. Open fractures and defects in practically any bone may be filled with composites according to various embodiments without the need for periosteal flap or other material for retaining a composite in fracture or defect. Even where a composite is not required to bear weight, physiological forces will tend to encourage remodeling of a composite to a shape reminiscent of original tissues.

Many orthopedic, periodontal, neurosurgical, oral and maxillofacial surgical procedures require drilling or cutting into bone in order to harvest autologous implants used in procedures or to create openings for the insertion of implants. In either case voids are created in bones. In addition to all the deficiencies associated with bone void mentioned above, surgically created bone voids may provide an opportunity for incubation and proliferation of any infective agents that are introduced during a surgical procedure. Another common side effect of any surgery is ecchymosis in surrounding tissues which results from bleeding of the traumatized tissues. Finally, surgical trauma to bone and surrounding tissues is known to be a significant source of post-operative pain and inflammation. Surgical bone voids are sometimes filled by the surgeon with autologous bone chips that are generated during trimming of bony ends of a graft to accommodate graft placement, thus accelerating healing. However, the volume of these chips is typically not sufficient to completely fill the void. Scaffolds and/or compositions of the present invention, for example scaffolds comprising anti-infective and/or anti-inflammatory agents, may be used to fill surgically created bone voids.

Similarly, the present scaffolds can be useful for treating skin tissue. Skin tissue that is damaged, injured, or the like can be difficult to heal, particularly if the damage or injury covers a wide area. The present scaffolds can serve to replace or supplement the need to add other tissue grafts (e.g., autologous tissue) to help treat such tissue. As will be understood by those of ordinary skill upon reviewing the present paper, the present scaffolds can be utilized to treat a variety of tissue types, conditions, injuries, and the like.

Inventive scaffolds may be administered to a subject in need thereof using any technique known in the art. A subject is typically a patient with a disorder or disease related to bone. In certain embodiments, a subject has a bony defect such as a fracture. Any bone disease or disorder may be treated using inventive composites/compositions including genetic diseases, congenital abnormalities, fractures, iatrogenic defects, bone cancer, bone metastases, inflammatory diseases (e.g., rheumatoid arthritis), autoimmune diseases, metabolic diseases, and degenerative bone disease (e.g., osteoarthritis). In certain embodiments, inventive osteoimplant composites are formulated for repair of a simple fracture, compound fracture, or non-union; as an external fixation device or internal fixation device; for joint reconstruction, arthrodesis, arthroplasty, or cup arthroplasty of hips; for femoral or humoral head replacement; for femoral head surface replacement or total joint replacement; for repair of vertebral column, spinal fusion or internal vertebral fixation; for tumor surgery; for deficit filling; for discectomy; for laminectomy; for excision of spinal tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; and, for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones, and for repair of bone surrounding cysts and tumors.

Scaffolds and/or compositions of the present invention can be used as bone void fillers either alone or in combination with one or more other conventional devices, for example, to fill the space between a device and bone. Examples of such devices include, but are not limited to, bone fixation plates (e.g., cranofacial, maxillofacial, orthopedic, skeletal, and the like); screws, tacks, clips, staples, nails, pins or rods, anchors (e.g., for suture, bone, and the like), scaffolds, scents, meshes (e.g., rigid, expandable, woven, knitted, weaved, etc), sponges, implants for cell encapsulation or tissue engineering, drug delivery (e.g., carriers, bone ingrowth induction catalysts such as bone morphogenic proteins, growth factors (e.g., PDGF, VEGF and BMP-2), peptides, antivirals, antibiotics, etc), monofilament or multifilament structures, sheets, coatings, membranes (e.g. porous, microporous, resorbable, etc), foams (e.g., open cell or close cell), screw augmentation, cranial, reconstruction, and/or combinations thereof.

In some embodiments porous scaffolds are synthesized and used by a one-shot foaming process, allowing for time to manipulate and inject the polymer, followed by rapid foaming and setting. Injectable embodiments can be advantageous because they can offer minimally invasive surgical techniques and/or increase the capacity for customization of a scaffold at the point of care. Certain embodiments can be customized to an individual patient and type of injury.

EXAMPLES

The presently-disclosed subject matter is further illustrated by the following specific but non-limiting examples. Some examples are prophetic. Some examples may include compilations of data that are representative of data gathered at various times during the course of development and experimentation related to the presently-disclosed subject matter.

Example 1

This Example describes the synthesis and characterization of embodiments of the present PTK-UR scaffolds formed from PTK polymers and polyisocyanates. All data is reported as the mean and standard deviation. Statistical analysis was performed using single factor analysis of variance (ANOVA) and Tukey post-hoc comparison tests, with p-values less than 0.05 considered statistically significant.

PTK Polymer Synthesis and Characterization

All chemicals were purchased from Sigma-Aldrich (Milwaukee, Wis., USA) except the following. 2-mercaptoethyl ether (MEE), glutaraldehyde, and cobalt chloride were purchased from Fisher Scientific (Pittsburgh, Pa.), and the tertiary amine catalyst (TEGOAMIN33) was obtained from Goldschmidt (Hopewell, Va.). Glycolide and D,L-lactide were obtained from Polysciences (Warrington, Pa.). Coscat83, an organobismuth urethane catalyst, was supplied by ChasChem, Inc. (Rutherford, N.J.). Hexamethylene diisocyanate trimer (HDIt, Desmodur N3300A) was received from Bayer Material Science (Pittsburgh, Pa.). Cell culture reagents, including Dulbecco's Modified Eagle Medium (DMEM), fetal bovine serum (FBS), and penicillin/streptomycin were supplied by Gibco Cell Culture (Carlsbad, Calif.). All materials were used as received unless otherwise indicated.

A condensation polymerization protocol was utilized to synthesize the PTK prepolymer (Scheme 1). Briefly, p-toluenesulphonic acid monohydrate (PTSA) was added to a tri-necked boiling flask equipped with an attached addition funnel. The vessels were placed under vacuum for 15 minutes before being purged with nitrogen. The boiling flask was charged with anhydrous acetonitrile and batch-specific amounts of 2-mercaptoethyl ether (MEE) (x molar eq) and 1,4 butanedithiol (BDT) (1-x molar eq) where x=1, 0.75, 0.5, 0.25, and 0 for the different synthesized PTKs. The addition funnel was also charged with anhydrous acetonitrile and 2,2-dimethoxypropane (DMP) (0.83 molar eq). Both the addition funnel and boiling flask's solutions were purged with flowing nitrogen for 30 min before submerging the boiling flask into an oil bath at 80° C. After 15 min of temperature equilibration, the addition funnel stopcock was set so that the acetonitrile-DMP solution was added dropwise into the continuously stirring boiling flask over a period of 16 h. Post synthesis, the acetonitrile was removed by rotary evaporation and the resultant PTKs were isolated by precipitation into cold ethanol and dried under vacuum. The five synthesized copolymers with varying percent molar composition of MEE and BDT are each designated by its relative mol % MEE.

Figure 2:
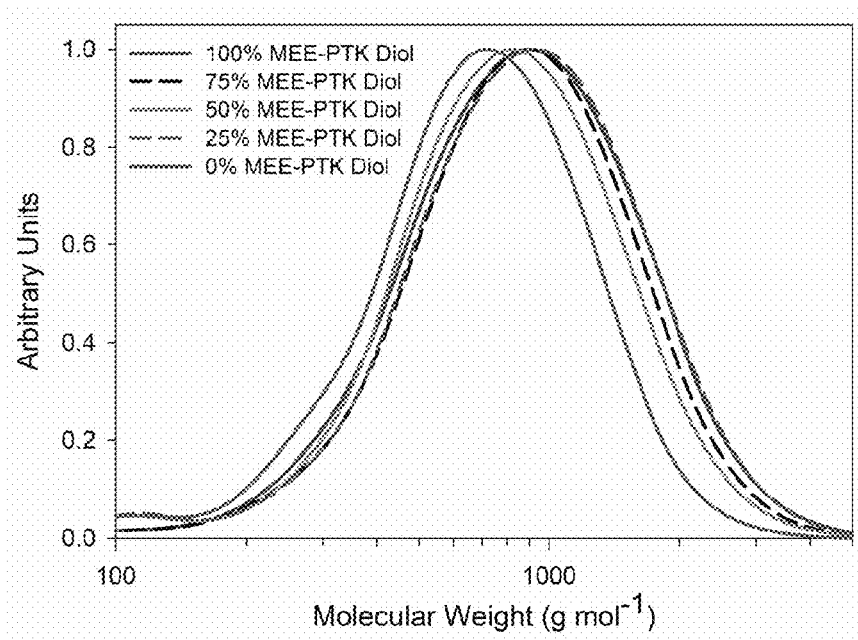
FIG. 2 includes gel permeation chromatograms of MEE-PTK diols (i.e., PTK polymers) comprising different molar concentrations of MEE.

To evaluate polymer compositions, samples of the respective PTKs were dissolved in deuterated chloroform (CDCl$_3$) and analyzed with $^1$H nuclear magnetic resonance spectroscopy (NMR, Bruker 400 MHz Spectrometer). $^1$H NMR chemical shifts were reported as δ values in ppm relative to the deuterated CDCl$_3$ (δ 7.26). Multiplicities are reported as follows: s (singlet), d (doublet), t (triplet), q (quartet), and m (multiplet). The number of protons (n) for a given resonance is indicated as nH and is based on integration values. $^1$H NMR (400 MHz, CDCl$_3$): δ 3.67-3.61 (m, 4H), δ 2.83 (t, 4H), δ 2.63 (t, 4H), δ 1.72 (t, 4H), δ 1.60 (s, 6H). $^1$H-NMR spectra confirmed that the composition of the synthesized polymers closely matched the monomer ratios in the feed (FIG. 1, Error! Reference source not found.), and gel permeation chromatography (GPC) analysis showed that the polymers had M$_n$ of ~1000 g mol$^{-1}$ with polydispersity index (PDI) values of ~1.35 (FIG. 2, Error! Reference source not found.).

TABLE 1

Characterization of PTK diols.

| Copolymer (PTK diol) | Feed MEE % | Actual MEE %$^a$ | GPC M$_n$$^b$ | PDI$^b$ | Titration M$_n$$^c$ |
|---|---|---|---|---|---|
| 100% MEE-PTK | 100% | 100% | 1027 | 1.38 | 825 |
| 75% MEE-PTK | 75% | 76% | 1005 | 1.34 | 850 |
| 50% MEE-PTK | 50% | 52% | 947 | 1.35 | 810 |
| 25% MEE-PTK | 25% | 26% | 1053 | 1.36 | 745 |
| 0% MEE-PTK | 0% | 0% | 807 | 1.32 | 680 |

$^a$Calculated from peaks at δ 1.72 and δ 3.64 ppm.
$^b$Calculated from GPC standards.
$^c$Calculated from measured titration OH numbers.

The resulting dithiol-terminated MEE-PTK polymers were converted into diols to prevent disulfide bridge formation from the reactive thiols, to generate telechelic end groups compatible with standard polyurethane synthesis, and to provide PTK polyols amenable to direct comparison with polyesters used in PEUR scaffold formation. Briefly, PTK dithiol polymers were transferred to a boiling flask, placed under vacuum, and then exposed to a nitrogen atmosphere. The flask was charged with dichloromethane (DCM) before adding a 10× molar excess of β-mercaptoethanol to the solution. This solution was stirred continuously at room temperature to reduce any disulfide bonds and recover the reactive thiol end groups. After 3 h of stirring, the DCM was evaporated off under vacuum before restoring nitrogen to the vessel, and the residue was washed three times in cold ethanol to remove residual β-mercaptoethanol. The reduced PTK polymers were dissolved in anhydrous tetrahydrofuran (THF) before adding a 10× molar excess of cesium carbonate (CsCO$_3$) under nitrogen and stirring for 30 min at room temperature. A 5× molar excess of 2-bromoethanol was next added to the solution and stirred for 18 hours under nitrogen at room temperature. After mixing, the solution was added to a separation funnel with an excess of deionized water to effectively separate the PTK-solubilizing THF layer from the water-soluble CsCO$_3$ catalyst. The hydroxyl-functionalized PTKs were extracted in THF before removing the solvent by rotary evaporation and the polymer residues were precipitated three times in cold ethanol before vacuum drying for 24 h.

Hydroxyl-functionalization was first confirmed by $^1$H NMR (400 MHz, CDCl$_3$): δ 2.74 (t, 4H). Molecular weights and polydispersities of the five synthesized PTK diols were analyzed by gel permeation chromatography (GPC, Agilent Technologies, Dover, Del.) using a mobile phase of N,N-dimethylformamide (DMF) with 100 mM LiBr and were quantified using a calibration curve generated from poly(ethylene glycol) (PEG) standards (400-4000 g mol$^{-1}$). PTK chain end-conversions from homobifunctional thiol groups to hydroxyl groups was confirmed with attenuated total reflectance Fourier transform infrared spectroscopy (ATR-FTIR; Bruker Tensor 27 FTIR, Billerica, Mass.). Thiol-terminated and hydroxyl-terminated PTK polymers were placed in contact with a ZnSe ATR crystal to quantify absorbance at 2550 cm$^{-1}$ and 3400 cm$^{-1}$, which correspond to absorbance peaks of free thiol and free hydroxyl groups, respectively. The hydroxyl (OH) numbers of the different PTK diols were determined by titration (Metrohm 798 MPT Titrino) according to ASTM E1899-08$^4$. Eq (1) was used to relate the molecular weight to the hydroxyl number of each titrated PTK:

$$M_n = \frac{56100 f}{\text{OH number}} \quad (1)$$

where 56,100 represents the molecular weight of KOH in mg/mol, f represents the hydroxyl functionality of the PTK (assumed to be 2 for the linear homobifunctional polymers in this study) and M$_n$ is the number-average molecular weight of the polymer.

Figure 3:
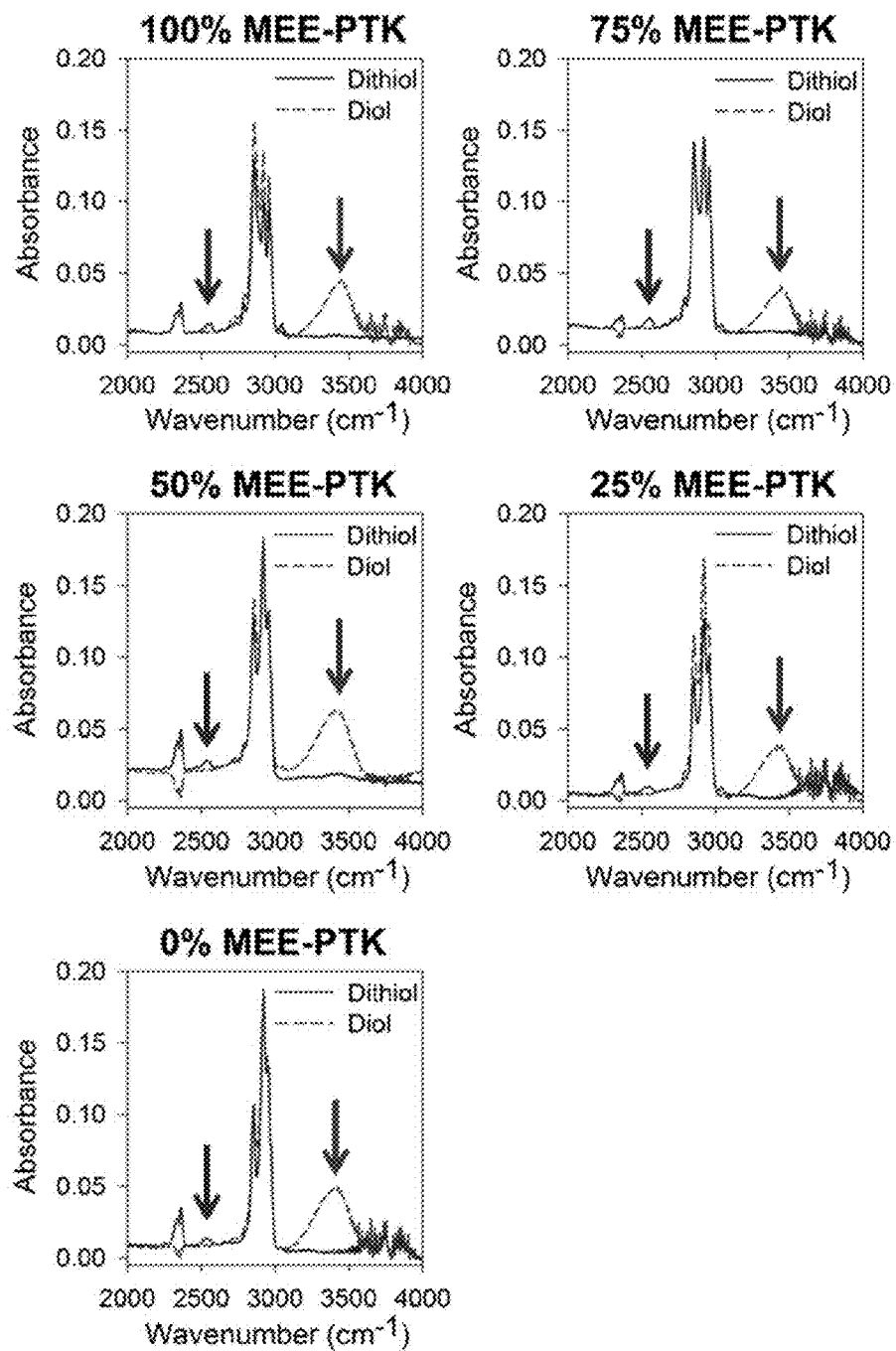
FIG. 3 includes ATR-FTIR spectra of thiol- and hydroxyl-terminated PTK polymers showing the thiol absorbance peak at 2550 cm$^{-1}$ (blue arrows) and the hydroxyl absorbance peak at 3400 cm$^{-1}$ (red arrows), and confirming the efficient conversion of PTK terminal thiols into hydroxyls.

The thiol absorbance peak at 2550 cm$^{-1}$ was apparent in the thiol-terminated, parent PTKs but did not appear with the hydroxyl-terminated polymers, which generated a characteristic ATR-FTIR hydroxyl peak at 3400 cm$^{-1}$ (FIG. 3). OH numbers experimentally measured with titration were utilized to calculate a titration M$_n$ (Error! Reference source not found.) that was used to balance the hydroxyl-isocyanate reaction used to form PTK-URs. The experimental OH numbers trended higher than theoretical values.

PTK-UR Scaffold Formation

Figure 4:
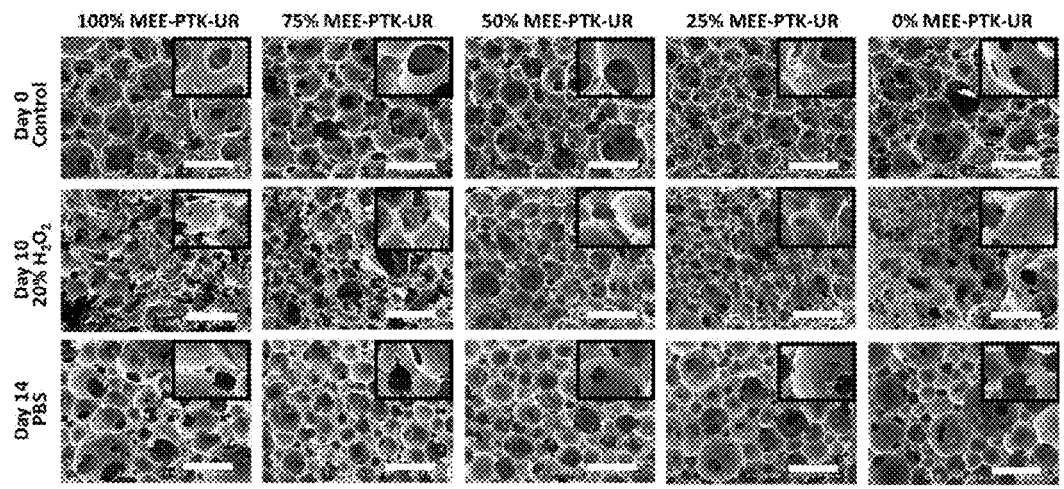
FIG. 4 includes SEM images of PTK-UR scaffolds, where day 0 samples (top row) show representative untreated scaffolds, the day 10 degradation samples (middle row) were incubated in 20% $H_2O_2$ in 0.1 M $CoCl_2$ for 10 days at 37° C. to demonstrate oxidative degradation of the PTK-URs, day 14 control samples (bottom row) were incubated in PBS for two weeks at 37° C. to demonstrate the resistance of the PTKs to hydrolytic breakdown, the white scale bar represents 600 μm, and the inset images display higher magnification views (2.6× magnification of large image).

PTK-UR scaffolds were successfully synthesized from the PTK diols and hexamethylene diisocyanate trimer (HDIt), yielding porous, mechanically robust 3D constructs as shown in FIG. 4. Specifically, the PTK-UR and PEUR (control) scaffolds were prepared using two-component reactive liquid molding of: (a) hexamethylene diisocyanate trimer (HDIt), and (b) a hardener component comprising the PTK diol, 0.5-1.5 parts per hundred parts polyol (pphp) water, 10.0 pphp TEGOAMIN33 catalyst, 0.5-3.0 pphp sulfated castor oil stabilizer, and 4.0 pphp calcium stearate pore opener. The makeup of the hardener components for the different respective PTK diols was individually optimized to yield scaffolds with mechanical integrity and an intact porous structure. The hardener component elements were first mixed for 30 s at 3300 revolutions per min (rpm) in a Hauschild DAC 150 FVZ-K SpeedMixer (FlackTek, Inc., Landrum, S.C.) before adding the HDIt and mixing for an additional 30 s. This reactive liquid mixture was allowed to rise freely for 10-20 min for complete setting and hardening. The targeted index (ratio of NCO to OH equivalents times 100) was 115, where the number of OH equivalents is calculated from the respective PTK's experimentally measured OH Number.

The PEUR scaffolds were formulated from a commercially available 900 g mol$^{-1}$ polyester triol, a synthesized 1000 g mol$^{-1}$ polyester diol, and a synthesized 1500 g mol$^{-1}$ polyester triol to serve as hydrolytically-degradable controls. These scaffolds are designated 900t-PEUR, 1000d-PEUR, and 1500t-PEUR, respectively. The commercially available 900t-PEUR represents a biological control that has been successfully used for in vivo applications, while the 1000d-PEUR and 1500t-PEUR were synthesized for a more direct material comparison to the PTK-URs because they yield PEUR scaffolds with similar crosslink densities to the PTK-UR scaffolds. To synthesize the trifunctional polyol, glycerol was vacuum dried for 48 hours at 80° C. and then added to a 100 mL three neck flask. ϑ-caprolactone, glycolide and D,L-lactide were added to the glycerol starter along with a stannous octoate catalyst. To obtain the bifunctional polyol, vacuum dried 1,4 butane diol was utilized as the starter.

Physical Properties

The core densities of PTK-UR and PEUR scaffolds were determined by measuring the mass and volume of cylindrical porous scaffold core samples, with the core porosities being subsequently calculated from these density values. The porous morphologies of the different PTK-UR scaffolds were qualitatively assessed by scanning electron microscopy (Hitachi S-4200 SEM, Finchampstead, UK). The amount of unreacted components (sol fraction) in the cross-linked network was measured from the mass loss of dried scaffold cylinders (25 mm×12 mm) previously incubated in DCM for 24 h. To measure the molecular weight between crosslinks ($M_c$), scaffold samples (n=3) were weighed dry and then incubated in DCM for 24 h. After incubation, samples were gently blotted to remove excess DCM and then the samples' swollen mass was measured. These values, along with the solvent parameters, were used in the Flory-Rhener equation to determine $M_c$. For measuring scaffold hydrophilicity, PTK-UR films of 100%, 50%, and 0% MEE-PTK diols were synthesized using an index of 105 and the gelling catalyst Coscat83 at 1000 ppm. After mixing the catalyst and PTK diol for 30 s at 3300 rpm, HDIt was added and mixed for an additional 30 s. The mixtures were cast into Teflon compression molds and allowed to cure for 18 h at 60° C. The contact angle of water on these PTK-UR films was measured using a Rame-Hart (Mountain Lakes, N.J.) Model A-100 contact angle goniometer. A 4 μL water drop was added to the film surface, and the contact angle was immediately measured. After 10 min, an equilibrium contact angle was also measured due to the molecular surface reorganization which increased the hydrophilicity at the contact site[5, 6].

The PTK-UR and PEUR formulations yield scaffolds with similar sol fraction and porosity, as seen in Error! Reference source not found. The molecular weight between crosslinks ($M_c$) for 1000d- and 1500t-PEUR was statistically equal to all of the PTK-UR scaffolds, while the 900t-PEURs had a significantly lower $M_c$ ($p<0.05$) relative to all other formulations except for the 100% and 0% MEE-PTK-UR materials (Error! Reference source not found.). The relatively low sol fraction values indicate that the isocyanates and diols are well matched for scaffold formation, while the ~90% porosity verifies that the PTK scaffolds are similar in structure to PEURs and possess an appropriate level of porosity for promoting cellular in-growth, nutrient exchange, and neo-vascularization in tissue engineering applications.

TABLE 2

Physical properties of PTK-UR and PEUR scaffolds.

| Scaffold | Sol Fraction (%) | Core Porosity (vol. %) | $M_c$ (kg mol$^{-1}$) |
| --- | --- | --- | --- |
| 100% MEE PTK-UR | 6.9% ± 1.6% | 90.9% ± 0.4% | 7.6 ± 4.2 |
| 75% MEE PTK-UR | 8.4% ± 1.4% | 89.0% ± 1.2% | 10.1 ± 4.9 |
| 50% MEE PTK-UR | 9.7% ± 6.1% | 86.9% ± 1.4% | 13.8 ± 6.5 |
| 25% MEE PTK-UR | 9.1% ± 2.7% | 90.6% ± 1.5% | 9.0 ± 5.0 |
| 0% MEE PTK-UR | 8.3% ± 3.2% | 88.8% ± 1.4% | 9.0 ± 5.8 |
| 900t PEUR | 4.1% ± 1.6% | 89.8% ± 1.2% | 2.5 ± 1.6 |
| 1500t PEUR | 4.7% ± 0.1% | 91.3% ± 0.2% | 13.2 ± 5.4 |
| 1000d PEUR | 7.7% ± 0.1% | 92.7% ± 0.7% | 7.7 ± 2.8 |

The relative surface hydrophilicity of the 100%, 50%, and 0% MEE-PTK-UR materials was assessed using contact angle measurements on PTK-UR films. After allowing 10 min to reach an equilibrium value, the contact angle values were 66°, 77°, and 80° for the 100%, 50%, and 0% MEE-PTK-UR films, respectively. As expected, scaffold contact angle was influenced by the composition of the PTK polyol, and the contact angle was inversely correlated with the mol % of the more hydrophilic MEE monomer in the PTK copolymer. These data suggest that the 100% MEE-PTK-UR is advantageous for cellular adhesion and tissue formation in vivo because relatively hydrophobic surfaces (contact angle >76°) preferentially adsorb hydrophobic serum proteins such as albumin over cellular adhesion proteins like fibronectin and vitronectin.

Thermal Analysis

Thermal transitions were measured by a TA Instruments (New Castle, Del.) Q200 DSC and Q800 DMA. For DSC analysis samples ranging in mass from 10-15 mg were heated from −80° C. to 200° C. at a rate of 10° C. min$^{-1}$, cooled to −80° C. at a rate of −20° C. min$^{-1}$, and heated a second time to 200° C. at a rate of 10° C. min$^{-1}$. All transitions were obtained from the second heating run. For DMA analysis cylindrical samples (6×6 mm) of foams were analyzed from −80° to 55° C. at a ramp rate of 1° C. min$^{-1}$. Foams were compressed at a frequency of 1 Hz with 1% strain during the thermal treatment. Glass transitions were obtained at the peak of tan δ. See Table 3.

The scaffold $T_g$ values determined by DMA exceeded those measured by DSC by 30-50° C., as has been previously reported for similar 3D polyurethane materials. The thermomechanical properties of the PTK-UR and PEUR scaffolds indicate that both materials are phase-mixed, since the 3D polyurethane scaffolds all possessed a $T_g$ exceeding that of the polyol precursor soft segment.

TABLE 3

Thermomechanical properties of PTK-UR and PEUR scaffolds and neat polymers.

| | Polymer | Scaffold | |
|---|---|---|---|
| | DSC $T_g$ (° C.) | DSC $T_g$ (° C.) | DMA $T_g$ (° C.) |
| 100% MEE-PTK | −66.1 | −25.2 | 20.7 |
| 75% MEE-PTK | −67.7 | −36.0 | 14.9 |
| 50% MEE-PTK | −78.5 | −11.1 | 13.9 |
| 25% MEE-PTK | −72.9 | −27.9 | 20.3 |
| 0% MEE-PTK | −76.8 | −19.3 | 23.1 |
| 900 Triol Polyester | −47.7 | −1.7 | 34.4 |
| 1500 Triol Polyester | −56.9 | −26.4 | 24.7 |
| 1000 Diol Polyester | −43.1 | −30.1 | 18.2 |

Mechanical Properties

The mechanical properties of the different PTK-UR and PEUR scaffold formulations was measured in compression at 37° C. under wet conditions using dynamic mechanical analysis (DMA, Q800 DMA, TA Instruments, New Castle, Del.). Cylindrical 6×6 mm scaffold samples were tested after incubation in phosphate buffered saline (PBS) for 7 days at 37° C. (wet conditions). Using a preload force of 0.1 N, samples were compressed along the longitudinal axis at a strain rate of 10%/min until 60% compressive strain was achieved. The Young's modulus for each sample was calculated from the slope of the initial linear region of each respective stress-strain curve after toe-in.

Figure 5:
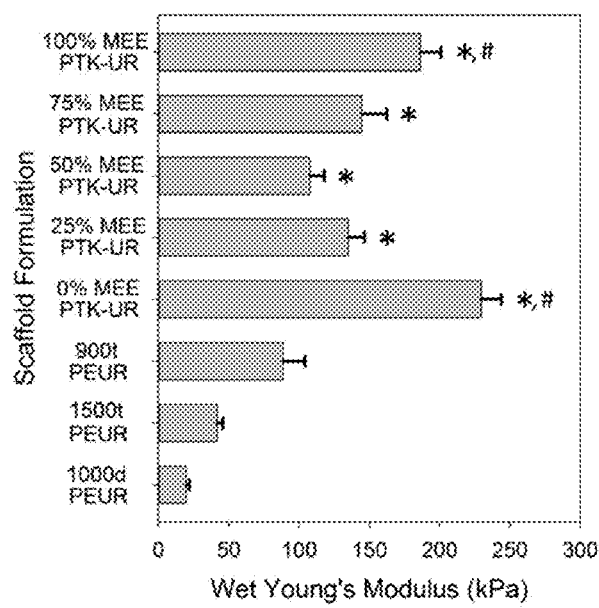
FIG. 5 includes a plot showing the compressive moduli of porous scaffolds determined under wet conditions at 37° C. (*$p<0.05$ compared to 1500t- and 1000d-PEUR; #$p<0.05$ compared to 900t-PEUR).

The wet compressive moduli of the PTK-UR samples ranged from 100-250 kPa, and the PEUR moduli ranged from 20-100 kPa (FIG. 5). Although the 1500t-PEUR, 1000d-PEUR, and PTK-UR scaffolds had similar $M_c$ values, all of the PTK-UR formulations had significantly higher modulus values than the 1500t-PEUR and 1000d-PEUR materials. However, there was no consistent trend between PTK-UR scaffold composition and modulus. Due to its higher crosslink density, the 900t-PEUR achieved stiffness values closer to the PTK-UR samples, though even this formulation was significantly less stiff than the 100% and 0% MEE-PTK-UR materials. Because of the more closely matched mechanical properties and the established precedent for their use, the 900t-PEUR scaffolds were used as a control for comparison to PTK-UR scaffolds in subsequent in vitro and in vivo studies.

In Vitro Degradation under Aqueous and Oxidative Conditions

Long-term hydrolytic stability of PTK-UR and PEUR scaffolds was determined by incubating ~10 mg samples in PBS at 37° C. on a shaker and measuring the mass loss at each time point (n=3). Before beginning the experiment, scaffolds were soaked in an excess of DCM for 24 h to remove any unreacted components before vacuum drying for 24 h. Scaffold samples were removed from the buffer at each time point, rinsed in deionized water, vacuum dried for 48 h, and weighed. The buffer medium was not changed between time points. Short term oxidative degradation rates of PTK-UR scaffolds were similarly assessed using an oxidative degradation medium that simulates in vivo oxidative degradation at an accelerated rate. This oxidative medium comprised 20 wt % hydrogen peroxide ($H_2O_2$) in 0.1 M cobalt chloride ($CoCl_2$), with the $H_2O_2$ and cobalt ion reacting to stimulate oxidative radical formation. As with the long-term study, triplicate samples were pre-soaked in DCM for 24 h before vacuum drying and incubated at 37° C. in the oxidative medium on a shaker. At specified time points over 10 d, samples were removed, rinsed with deionized water, vacuum dried, and weighed. The oxidative medium was replaced every 3 days, and the morphology of both PBS-incubated and $H_2O_2$-incubated scaffolds was qualitatively assessed with SEM.

The effect of radical concentration on PTK-UR scaffold degradation kinetics was also explored. The original 20% $H_2O_2$ in 0.1 M $CoCl_2$ degradation medium was diluted ten and one-hundred fold to yield a 2% $H_2O_2$ in 0.01 M $CoCl_2$ solution and a 0.2% $H_2O_2$ in 0.001 M $CoCl_2$ solution. These two diluted degradation media were used to incubate 100%, 50%, and 0% MEE-PTK-UR scaffolds along with 900t-PEUR control samples, with material preparation steps and incubation conditions being the same as previously described.

The oxidative degradation medium comprising $H_2O_2$ and $CoCl_2$, which produces hydroxyl radicals, destabilize the TK bond, leading to chain scission and breakdown into the original constitutive monomers (MEE and BDT) and acetone. The hypothesized degradation mechanism is seen in Scheme 4, and it is predicted that these small byproducts will be rapidly cleared in an in vivo environment. Furthermore, these thiolated monomers have been shown to cause limited in vitro cytotoxicity and a minimal host inflammatory response in vivo when incorporated into a similar polyurethane system. The isocyanate HDIt was utilized in these studies because it is stable, allowing more specific study of the degradation behavior of the polyol component.

Scheme 4

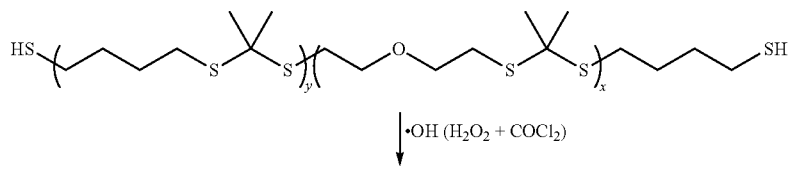

-continued

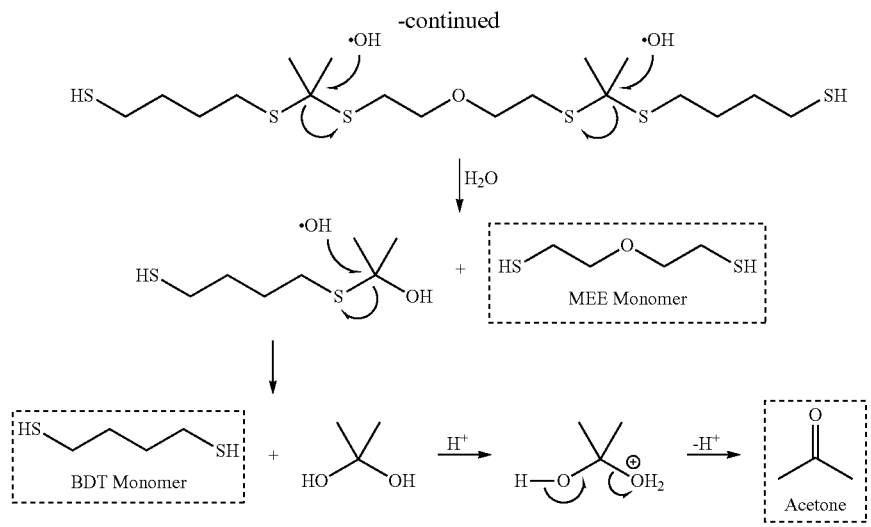

Figure 6A:
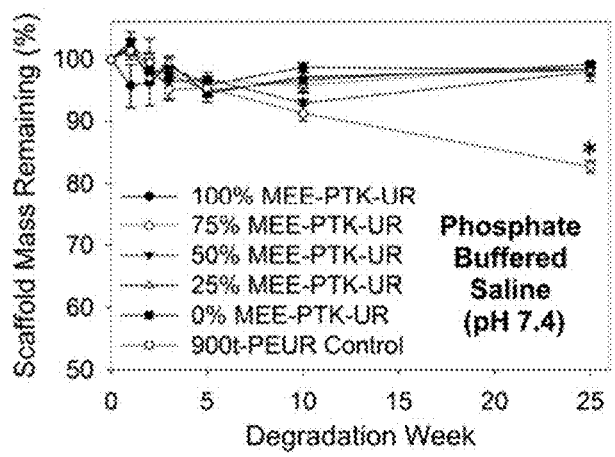
FIGS. 6A-F show plots illustrating stability and degradation properties of PTK-UR scaffolds. (A) long-term stability of PTK-UR scaffolds incubated in PBS. (B) percent degradation of PTK-UR scaffolds incubated in oxidative medium (20% $H_2O_2$ in 0.1 M $CoCl_2$; dashed lines represent best-fit curves; *$p<0.05$. (C) percent mass remaining of 100% MEE-PTK-UR scaffolds incubated in oxidative media containing 20%, 2%, and 0.2% $H_2O_2$. (D) percent mass remaining of 50% MEE-PTK-UR scaffolds incubated in oxidative media containing 20%, 2%, and 0.2% $H_2O_2$. (E) percent mass remaining of 0% MEE-PTK-UR scaffolds incubated in oxidative media containing 20%, 2%, and 0.2% $H_2O_2$. (F) degradation constants used to generate the best-fit curves in (B-E), as determined by non-linear regression analysis.
Figure 6B:
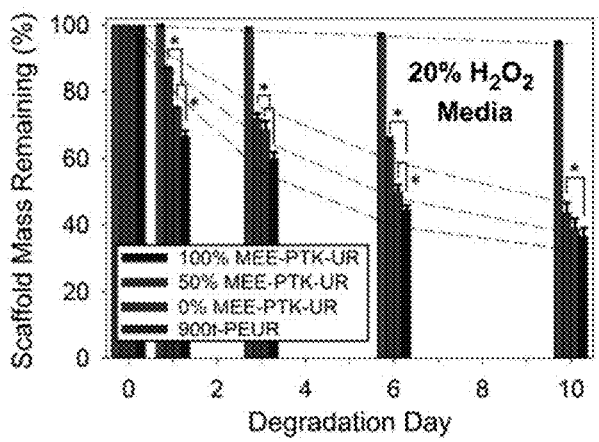
Figure 7:
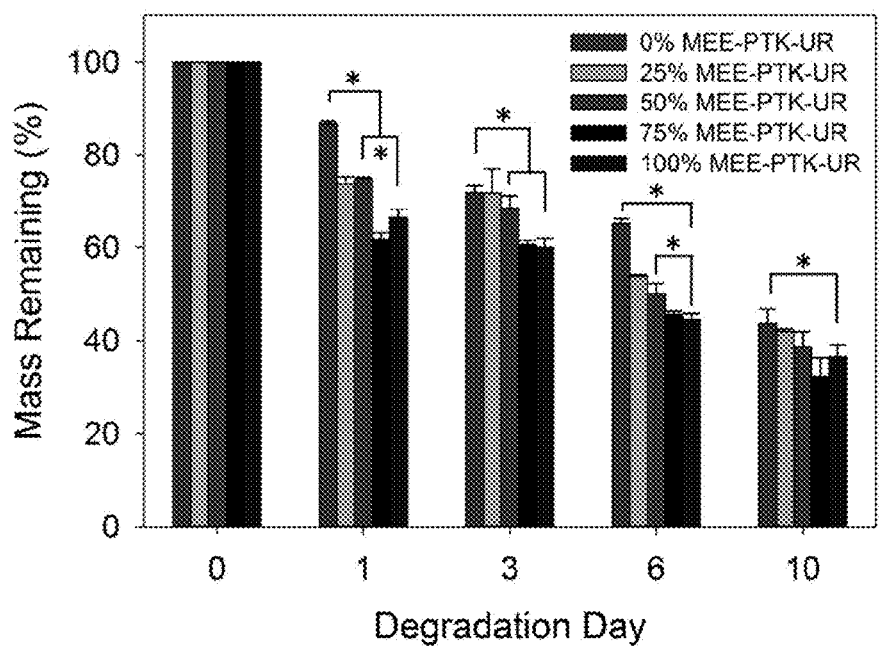
FIG. 7 includes a plot showing the in vitro degradation of a full set of PTK-UR scaffolds incubated in accelerated oxidative conditions (20% $H_2O_2$ in 0.1 M $CoCl_2$).
Figure 8A:
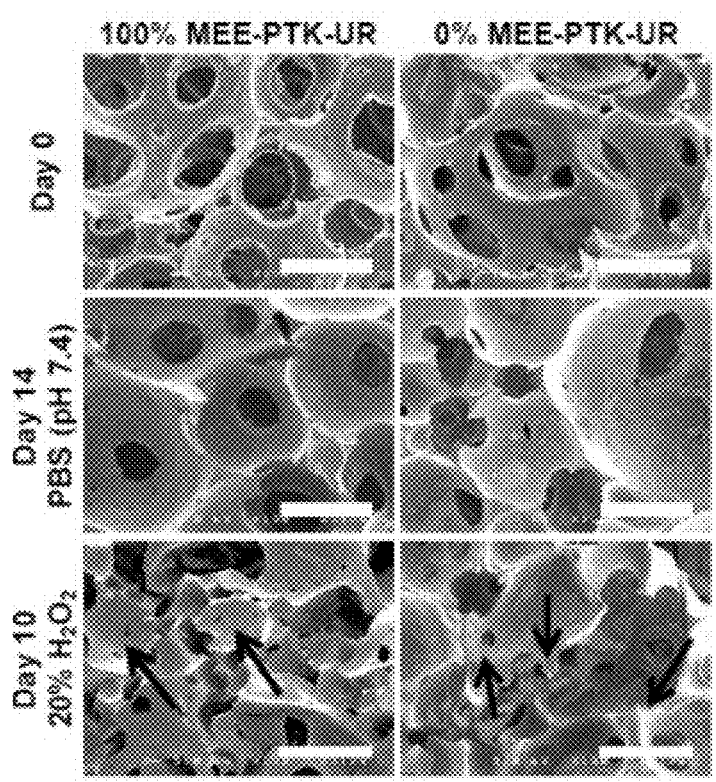
FIGS. 8A-B show images illustrating the ROS-dependent degradation of PTK-UR scaffolds. (A) PTK-UR scaffolds: freshly made (top row), incubated in PBS for 14 d (middle row), and incubated in 20% $H_2O_2$ media for 10 d (bottom row). Scale bars=231 μm. The ROS-degraded scaffolds feature irregular pore morphology and surface pitting. (B) PTK-UR scaffolds seeded with RAW 267.4 macrophages and incubated for 3 d in either control or activation media (LPS and IFN-γ). The activated macrophages generated visible pitting on the scaffold surface (black arrows), indicating ROS-mediated scaffold degradation. Scale bar=20 μm.

The PTK-UR scaffolds were stable over a long-term, 25-week study in PBS at 37° C., while the 900t-PEUR scaffolds underwent significant hydrolytic degradation over this time period (FIG. 6A). Conversely, the PTK-URs rapidly degraded under accelerated oxidative conditions (20% $H_2O_2$ in 0.1 M $CoCl_2$) as seen in FIG. 6B. Furthermore, there was a relationship between the PTK composition and degradation rate, as the scaffolds with higher MEE content in the PTK polyol degraded faster (FIG. 6B). Ethers are stable in aqueous media but that oxidative radicals can degrade them in vitro and in vivo. Thus, without being bound by theory or mechanism, it is hypothesized that the faster ROS-dependent degradation seen in both the 100% and 50% MEE-PTK-UR materials may result from a combination of oxidative degradation of both TKs and ethers, while the 0% MEE-PTK-UR scaffolds are degraded solely by TK scission. These results indicate that scaffold degradation rates can be tuned by the composition of the PTK polyol. The degradation profiles of all PTK-UR formulations in the 20% $H_2O_2$ media are seen in FIG. 7. SEM images of PTK-UR scaffolds after 10 days of incubation in oxidative media illustrated loss of the porous architecture and surface pitting (FIG. 8A), while these morphological changes in scaffold architecture were not apparent following PTK-UR scaffold incubation in PBS for 14 days (FIGS. 4 and 8A).

Mathematical Model of ROS-dependent PTK-UR Scaffold Degradation

Figure 6C:
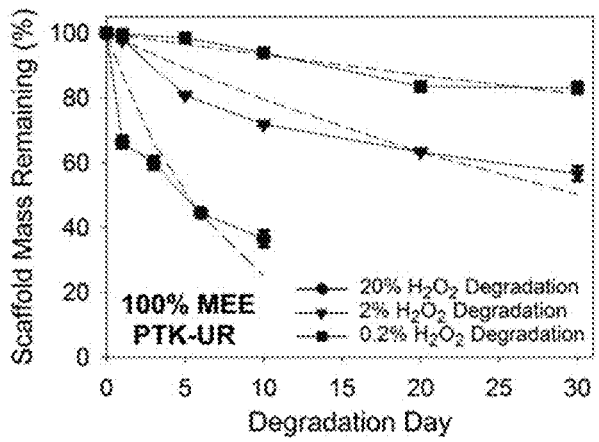
Figure 6D:
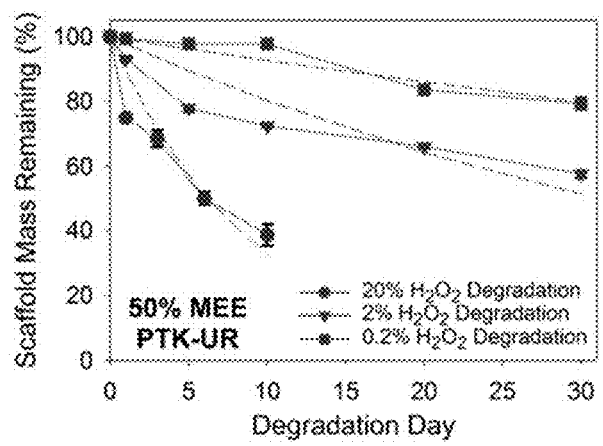
Figure 6E:
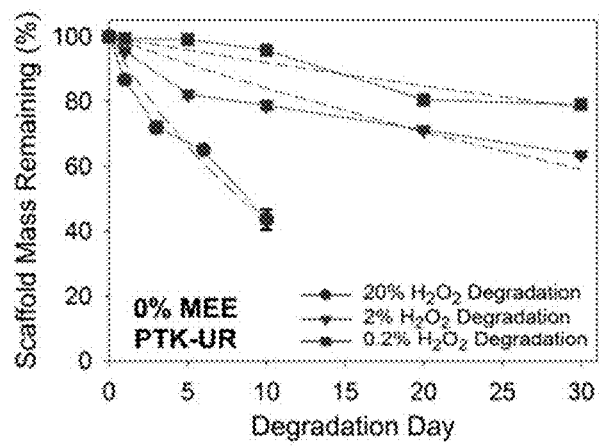

To further elucidate the relationship between ROS concentration and the degradation rates of the different PTK-UR scaffold formulations, scaffold degradation was measured in oxidative degradation media comprising 20%, 2%, and 0.2% $H_2O_2$ containing 0.1, 0.01, and 0.001 M $CoCl_2$, respectively. The degradation rates of selected PTK-UR scaffold formulations tested were dependent on the concentration of $H_2O_2$ (FIG. 6C-E). The degradation behavior of the PTK-UR scaffold formulations were fit to first-order decay kinetics equation to create a mathematical model of scaffold degradation with respect to $H_2O_2$ concentration. The first-order degradation model is given in Eq 2.

$$M_t/M_0 = e^{-kt} \quad (2)$$

Figure 6F:
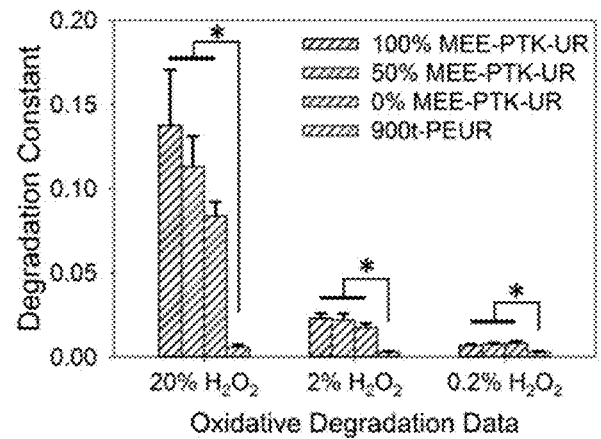
Figure 9:
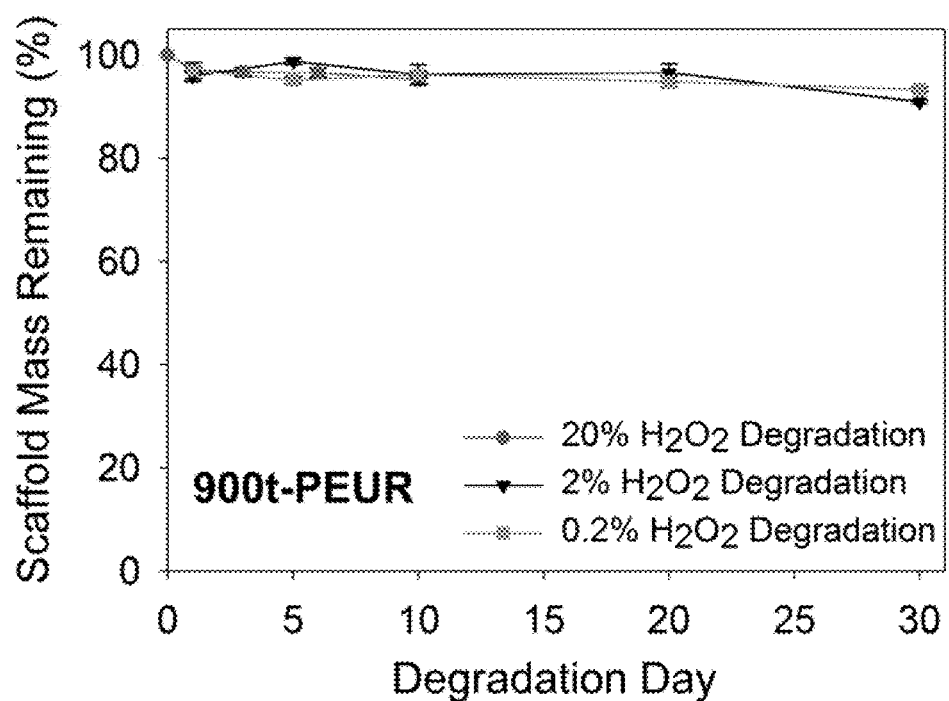
FIG. 9 includes a plot showing the $H_2O_2$ dose-dependent degradation of 900t-PEUR scaffolds.

In this equation, $M_t$ is the scaffold mass remaining at time t, $M_0$ is the initial scaffold mass, and k is the degradation rate constant. Non-linear regression was used to fit this modified first order degradation model to the experimentally determined degradation data. This method was used to determine the rate constant k for each scaffold's decay profile in the respective $H_2O_2$ oxidative medium. The fitted degradation profiles are concurrently shown with the respective experimental data as dotted lines in FIG. 6C-E. Agreement between the model and experimental data confirm that the PTK-UR scaffolds degrade by first-order kinetics with respect to ROS concentration. The degradation rate constants derived from the non-linear regression fitting of the experimental data gathered in 20% $H_2O_2$ media (FIG. 6F) also illustrate the relationship between degradation rate and the % MEE-PTK polyol used in PTK-UR scaffold fabrication. This trend is also seen in the PTK-UR samples incubated in 2% $H_2O_2$ media, though to a lesser magnitude. The degradation rate constants were significantly higher for all PTK-UR scaffolds than PEUR scaffolds in the 0.2% $H_2O_2$ media, but there was no trend between the different PTK-UR scaffolds at this dose. Contrary to the PTK-UR scaffolds, the 900t-PEUR samples incubated in these same oxidative media did not display $H_2O_2$ dose-dependent degradation (FIGS. 6F and 9). These collective data confirm that thioketal-based polyols are selectively broken down by ROS and that their rate of degradation is first order with respect to the concentration of radical species in the local environment.

Cell-mediated PTK-UR Degradation In Vitro

Figure 8B:
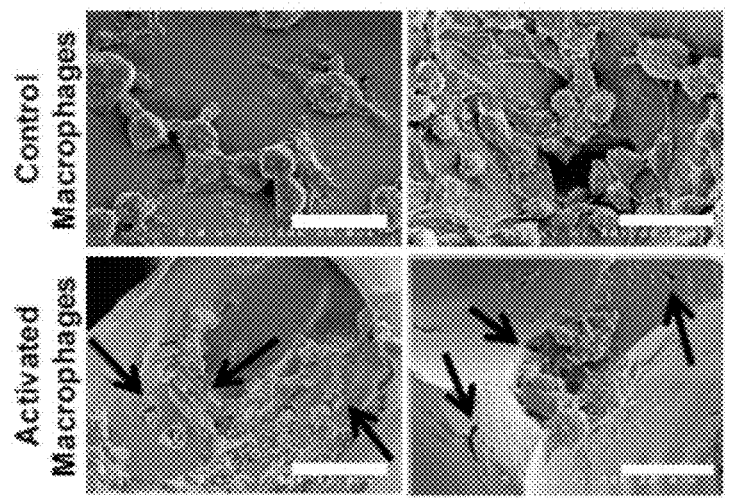

RAW 264.7 macrophages were cultured in DMEM supplemented with 10% FBS and 1% penicillin/streptomycin until the cell population reached confluence. 100% and 0% MEE-PTK-UR scaffolds were cut into 6.5×1-mm discs, sterilized by UV-radiation for 1 h (30 min per side), placed into 96-well plates, and incubated with culture medium for 30 min. Macrophages were seeded onto the scaffolds at a density of $2.5 \times 10^5$ cells/scaffold. The cells were allowed to adhere to the scaffolds for 3 h, at which point the old media were removed and the cells were treated with either fresh culture media or media containing 5 μg $mL^{-1}$ lipopolysaccharide (LPS) and 1000 U $mL^{-1}$ IFN-γ to promote classical macrophage activation and enhanced ROS production[1, 13, 14]. Cells were incubated on the scaffolds for 3 d with fresh culture media being applied daily. After the 3 d incubation, the scaffolds were fixed in 5% glutaraldehyde for 2 h followed by 2% osmium tetroxide for 1 h. These fixed scaffolds were dehydrated in ascending grades of ethanol before being vacuum dried and imaged with SEM to evaluate surface pitting. SEM imaging of scaffolds after three days illustrated surface pitting by activated macrophages, while cell-mediated remodeling of the scaffold surface was less apparent for the control cells (FIG. 8B), indicating that physiologic concentrations of ROS can degrade PTK-UR materials.

Biocompatibility of PTK-UR Scaffolds In Vitro and In Vivo

Figure 10A:
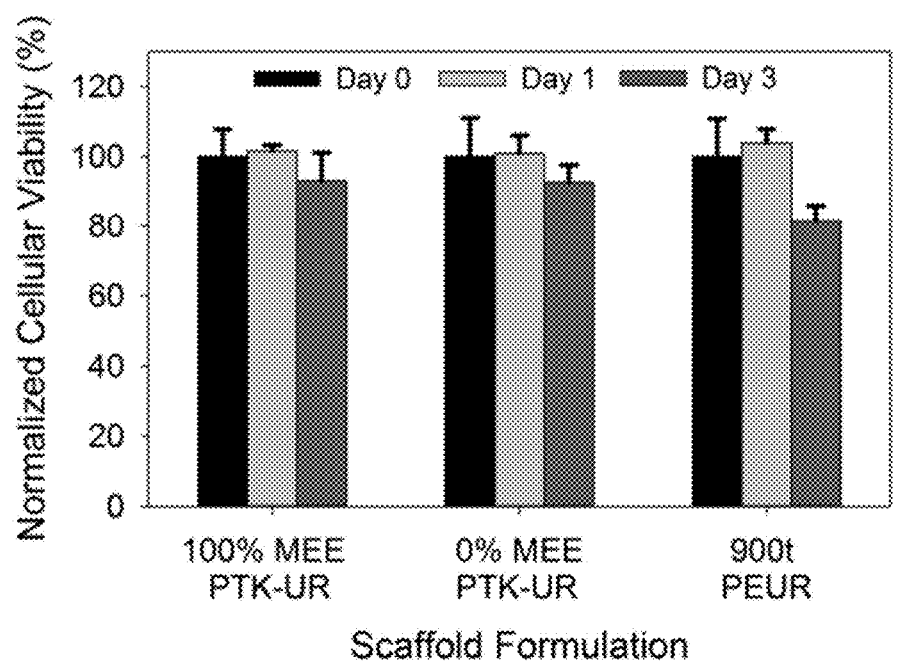
FIGS. 10A-C shows plots and images illustrating biocompatibility, cellular infiltration, and wound thickness of PTK-UR and PEUR scaffolds. (A) in vitro biocompatibility of porous 3D PTK-UR scaffolds. (B) in vivo cellular infiltration into PTK-UR and control PEUR scaffolds 21 d post-implantation in Sprague-Dawley rats. (C) wound thickness of PTK-UR vs. PEUR scaffolds.

NIH 3T3 mouse fibroblasts stably transfected with a firefly luciferase reporter gene were cultured in DMEM supplemented with 10% FBS and 1% penicillin/streptomycin until the cell population reached confluence. 100% MEE-PTK-UR, 0% MEE-PTK-UR, and 900t-PEUR scaffolds were cut into 6.5×1-mm discs, sterilized by UV-radiation for 1 h (30 min per side), placed into a black-walled 96-well plate, and incubated with culture medium for 30 min. Fibroblasts were seeded at a density of $5.0 \times 10^4$ cells/scaffold on n=3 scaffolds and allowed to grow for 0, 1, and 3 days in 200 µL of culture media per well (changed every two days). On the final day of seeding, the day 0 cells were allowed to adhere for 2 h before culture media containing a luciferin substrate was added to all cell-seeded scaffolds. After 10 min, the scaffolds were imaged with an IVIS 100 (Caliper Life Sciences, Hopkinton, Mass.) luminescent imaging system with an exposure time of 2 min to quantify the luciferase-based luminescent cell signal from each scaffold. All readings were normalized to day 0 luminescent signal values. Stably transfected NIH 3T3 mouse fibroblasts remained viable on 100% MEE-PTK-UR, 0% MEE-PTK-UR, and 900t-PEUR scaffolds over 3 days of culture in vitro (FIG. 10A), and none of the scaffold formulations displayed a significant difference in cell number over time or relative to each other. These data indicate that PTK-UR scaffolds achieved cellular viability levels analogous to PEUR scaffolds that are cytocompatible and have been successfully utilized in vivo.

Figure 10B:
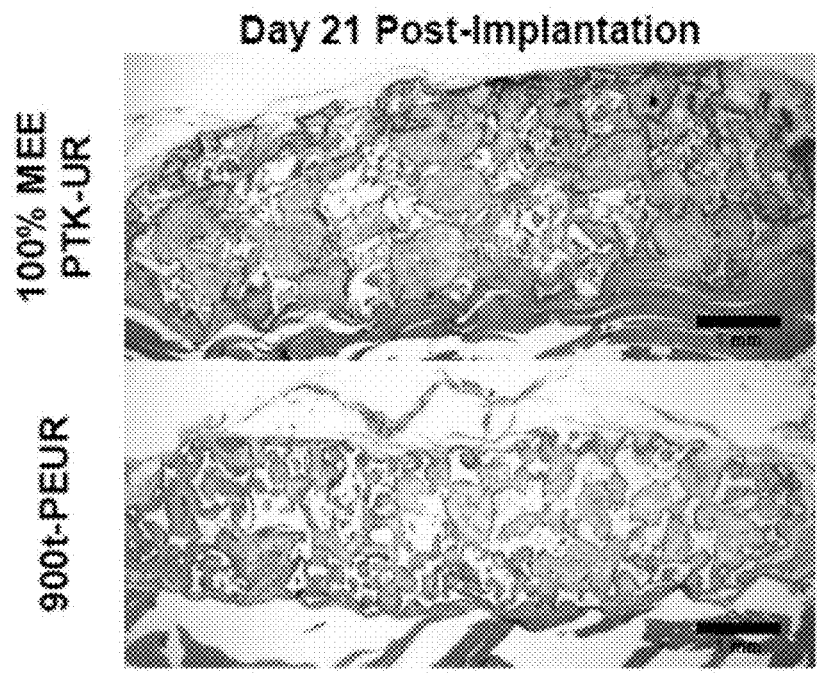

Also, 100% MEE-PTK-UR and 900t-PEUR scaffolds were fabricated as previously described. 2.5×10 mm discs were cut and sterilized with ethylene oxide prior to implantation into ventral subcutaneous sites in adult male Sprague-Dawley rats. Scaffolds were excised at day 21 to evaluate new tissue formation in the implants. The tissues were fixed in formalin for 48 h followed by incubation in 70% ethanol for 48 h, embedding in paraffin, sectioning, and staining with hematoxylin & eosin. Histological sections were evaluated with Metamorph Imaging Software (Molecular Devices Inc., Sunnyvale Calif.) to evaluate wound size and new tissue growth. All surgical procedures were reviewed and approved by the Institutional Animal Care and Use Committee. The PTK-UR scaffolds supported robust cell infiltration and granulation tissue formation, while eliciting a minimal inflammatory response (FIG. 10B).

Figure 10C:
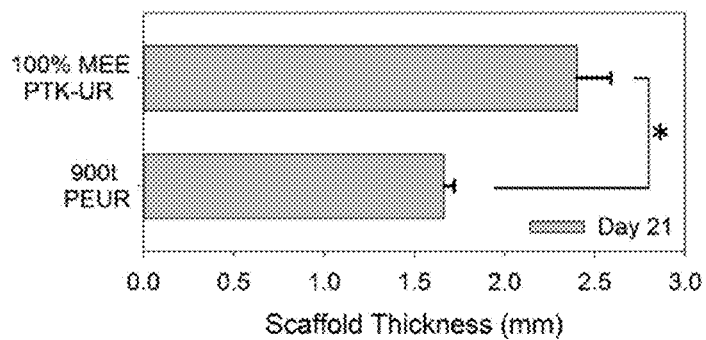

Although all implanted scaffold samples were cut to the same thickness pre-implantation (2.5 mm), PTK-UR scaffolds extracted 21 days after subcutaneous implantation had better maintenance of their original thickness relative to the PEUR scaffolds, which suffered from partial collapse of the pore structure following implantation in vivo (FIG. 10C). Though both formulations support new tissue growth into the scaffold interior, the PTK-UR samples were more mechanically resilient and more effectively stented the wound. This effect can be potentially attributed to both the significantly higher moduli of the 100% MEE-PTK-UR scaffolds relative to the 900t-PEUR formulation (FIG. 5) and also to the 900t-PEUR $T_g$ value (34.4° C.), which is close to body temperature (Table 3). This relatively high $T_g$ is predicted to make this PEUR scaffold less mechanically resilient at body temperature because it will be in its glassy transition viscoelastic region. The stenting effect seen in these PTK-UR scaffolds is advantageous for maximizing cell infiltration and new tissue formation and could potentially decrease scarring in clinical applications.

Example 2

This Example describes additional studied conducted on Sprague-Dawley rats using the scaffolds described in Example 1. Unless stated otherwise, the materials and method described in Example 1 were implemented in this Example as well.

Figure 11A:
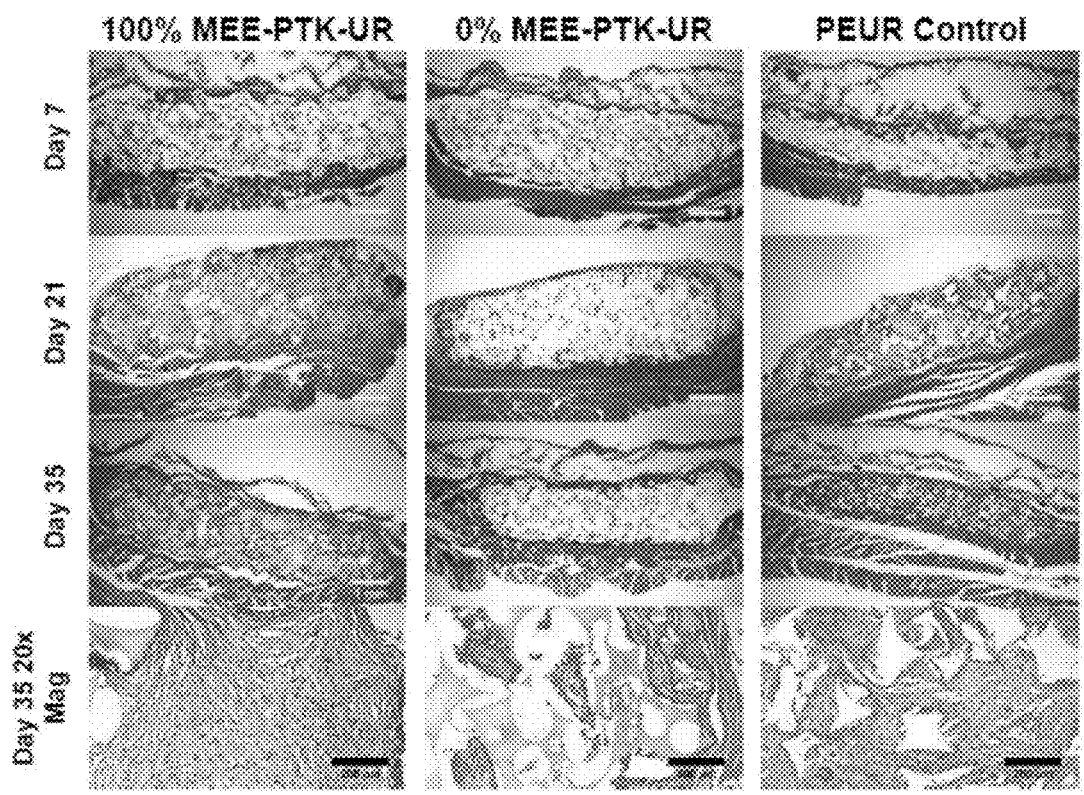
FIGS. 11A-D show graphs and images illustrating implanted scaffold behavior. (A) Histological sections showing temporal growth of new tissue into PTK-UR and control scaffolds over 35 days. (B) Plots showing the thickness of the scaffold and wound site over implantation. (C) Plots showing the total wound area of implanted scaffolds over time. (D) Plots showing the percent of the wound area occupied by scaffold. Data presented as mean±standard error (*$p<0.05$ between time points, #$p<0.05$ compared to the PEUR control at the same time point).
Figure 11B:
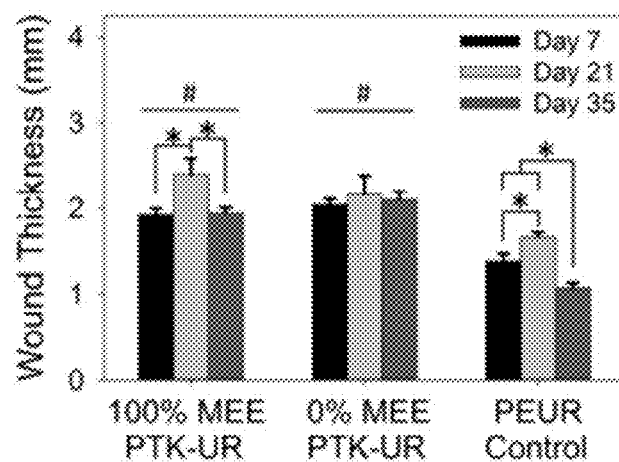
Figure 11C:
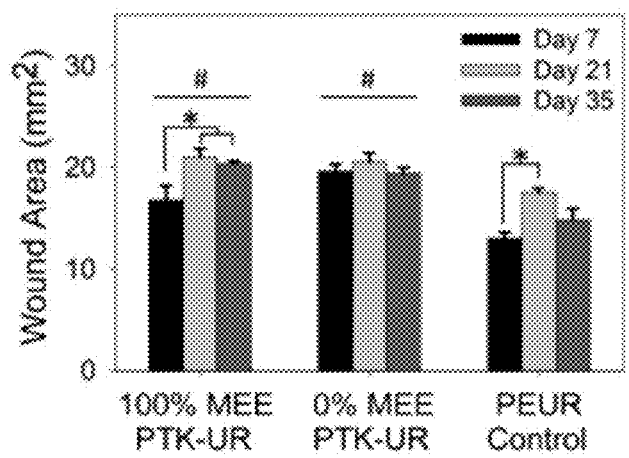
Figure 11D:
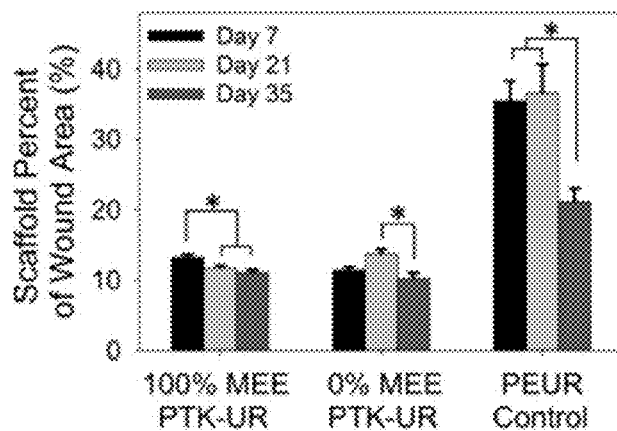

Briefly, pre-formed porous 100% and 0% MEE-PTK-UR scaffolds along with PEUR control scaffolds were implanted into ventral subcutaneous sites in male Sprague-Dawley rats for 7, 21, and 35 days. As shown in FIG. 11A, the 100% MEE-PTK-UR and PEUR scaffolds demonstrated tissue in-growth into the scaffold interiors by day 21, and both the 100% MEE-PTK-UR and PEUR scaffolds significantly degraded over the 35 day time frame. However, the PTK-UR scaffold formulations appeared to be more resilient materials in vivo as the PEUR scaffolds were significantly compressed from their initial thickness. None of the tested scaffolds led to an excessive immune response.

To test the ability of the scaffolds to treat tissue wounds in diabetic subjects, adult male Sprague-Dawley rats were injected with streptozotocin (45 mg/kg) to induce diabetes. One week post injection, the rats' blood glucose was measured and compared to previously measured baseline glucose levels to confirm diabetes development. The 100% MEE-PTK-UR formulation was chosen as the exemplary PTK-UR for implantation. Therefore, the diabetic rats were implanted with 100% MEE-PTK-UR and PEUR scaffolds and sacrificed at days 7, 21, 35, and 49 post scaffold implantation.

Figure 12:
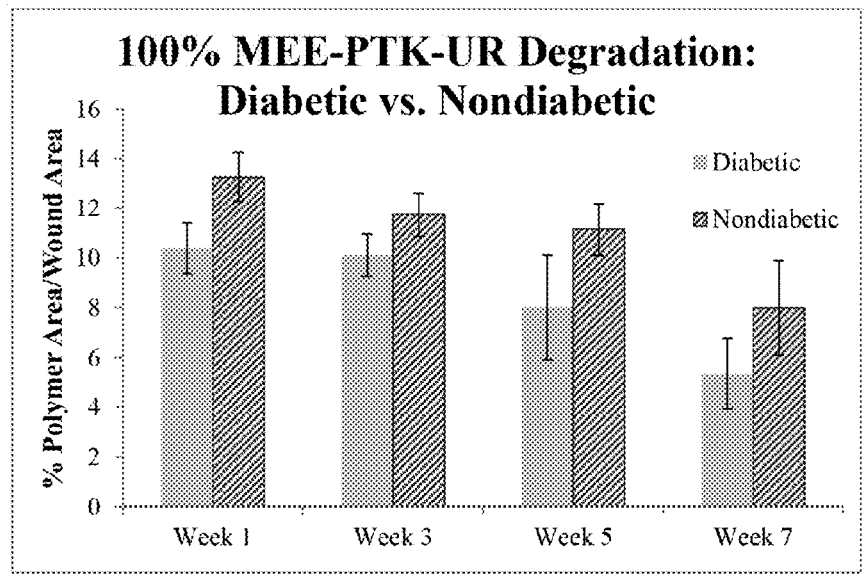
FIG. 12 includes a plot showing the degradation of 100% MEE-PTK-UR scaffolds implanted in diabetic and nondiabetic rats at 1, 3, 5, and 7 weeks post-implantation.

As diabetic rodent models have been shown to produce higher levels of reactive oxygen species (ROS), given the previous results, it was predicted that the PTK-UR scaffolds would degrade faster in the diabetic animals. Indeed, the PTK-UR scaffolds were significantly more degraded in the diabetic animals over all time points when compared to samples implanted in nondiabetic rats (FIG. 12).

Example 3

This Example describes the synthesis and characterization of embodiments of the present PTK-UR scaffolds formed from hydroxyl end functional thioketals and isocyanates. The reactivity, rheological properties, mechanical properties, degradation rate, and cell proliferation response of the cements were assessed in vitro. The biocompatibility and remodeling of PTKUR/ceramic composite cements were investigated in a rabbit femoral condyle plug defect model to assess material resorption and integration with the host bone.

Hydroxyl End Functional TK Synthesis and Characterization

Figure 13A:
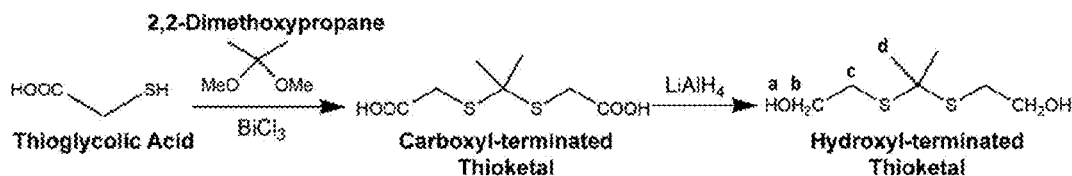
FIGS. 13A-D show synthesis and characterization of low molecular weight thioketal diol. (A) Synthesis scheme. (B-C) Characterization by (B) NMR and (C) GPC indicate that the targeted molecular structure was obtained. (D) Viscosity of the TK diol is independent of shear rate.

The schematic for thioketal diol synthesis is illustrated in FIG. 13A. Bismuth (III) chloride was added to a dry boiling flask that was subsequently dried with a hot air gun under vacuum for about 5 minutes to ensure completely dry catalyst conditions. The flask was then purged with nitrogen and left under a positive pressure with nitrogen for the remainder of the reaction. Anhydrous acetonitrile was charged to the flask to dissolve the catalyst. 2,2-dimethoxypropane and thioglycolic acid were added to the flask, and the reaction was allowed to proceed for 24 hours while stirring at room temperature.

Following the reaction, the carboxyl-terminated intermediate was filtered with a Buchner funnel, rotary evaporated (Buchi Rotovap R-200, 35° C.), and dried under vacuum overnight. The carboxyl groups were then reduced to produce a hydroxyl-terminated TK. To reduce the carboxyl groups and produce the hydroxyl-terminated TK, a 3-neck boiling flask was fitted to a 10° C. condenser capped with a 1-way glass stop-cock, a constant pressure dropping funnel, and a rubber stopper. The reactor was heated with a heat gun under vacuum for about 5 minutes to ensure completely dry reaction conditions. The reactor was then placed in an ice bath, purged with dry nitrogen, and maintained under positive pressure with nitrogen throughout the functionalization. Lithium aluminum hydride ($LiAlH_4$) was added to the 3-neck boiling flask and dissolved in diethyl ether. Using anhydrous techniques, anhydrous tetrahydrofuran was added to the boiling flask containing the carboxyl-terminated TK. The resulting solution was then transferred to the dropping funnel and added to the $LiAlH_4$ solution dropwise at 0° C. After all of the TK solution was added, the ice bath was replaced with an oil bath and the reaction mixture was refluxed at 52° C. for 6-8 hours. Unreacted $LiAlH_4$ was quenched by adding DI water dropwise followed by 1 M sodium hydroxide to aid in product extraction. By-products of the reaction were filtered using a Buchner funnel and filtration flask, and a separation funnel and diethyl ether were used to extract and isolate the TK diol product. The solvent was removed by rotary evaporation and the product dried under vacuum overnight for a completely dry, solvent-free TK diol.

Nuclear magnetic resonance spectroscopy ($^1$H NMR, Bruker 400 MHz NMR) in dimethylsulfoxide (DMSO) and attenuated total reflectance Fourier transform infrared spectroscopy (ATR-FTIR) verified the chemical structure of the TK diol. Titration of a sample reacted with excess p-toluenesulfonyl isocyanate with tetrabutylammonium hydroxide was used to determine the hydroxyl (OH) number of the TK diol according to ASTM E1899-08. The number-average molecular weight ($M_n$) was calculated from the OH number using Eq (3):

$$M_n = \frac{56,100}{\text{OH Number}} \quad (3)$$

Gel permeation chromatography (GPC) confirmed the molecular weight of the diol. Samples were run in a N,N-dimethylformamide (DMF) mobile phase and quantified using a calibration curve prepared from poly(ethylene glycol) (PEG) standards.

Quasi-Prepolymer Synthesis and Characterization

A quasi-prepolymer was prepared according to methods previously described. Briefly, a 2.5:1 molar ratio of LTI:TK (3.75:1 NCO:OH equivalent ratio) was charged to a 100-mL boiling flask and purged with nitrogen while stirring in an oil bath at 45° C. TK diol was added to LTI drop-wise from a syringe through a 16 G needle inserted through the rubber stopper. The reaction was allowed to proceed for 3 hours yielding an LTI-TK quasi-prepolymer. The NCO number was determined by titration according to ASTM D2572-97.

Polyurethane/Ceramic Composite Synthesis and Characterization

PTKUR/ceramic composites were fabricated by reactive liquid molding and catalyzed using a 5% FeAA solution in ϑ-caprolactone. The isocyanate index (NCO:OH equivalent ratio*100) was 140 for all materials. TK diol, LTI-TK prepolymer, and 55 wt % MG or 60 wt % nHA particles were hand-mixed to yield a reactive paste. These concentrations of the ceramic particles were selected as the maximum values that could be added while maintaining a cohesive reactive paste. Once homogeneous, 0.06 wt % FeAA (in solution) was added to catalyze the reaction between the LTI-TK prepolymer and the TK diol. The morphology of the composite was verified by scanning electron microscopy (Hitachi S4200 SEM) following gold sputter coating of thin sections of sample (Cressington Q108) for 45 seconds at 30 mA.

PTKUR films (without ceramic) synthesized using varying isocyanate indices were submerged in water for 2 weeks and water uptake measured periodically by weighing the samples. Swelling of films with indices of 110, 125, and 140 was calculated according to Eq (4), where $M_s$ is the swollen mass and $M_0$ is the initial mass. This information was used to determine effects of index on extent of crosslinking.

$$\% \text{ Swelling} = \frac{M_S - M_0}{M_0} \times 100\% \quad (4)$$

Reaction Kinetics and Working Time

The reaction kinetics of the composite were assessed using methods described previously. ATR-FTIR was used to evaluate the reaction rate of the isocyanate-terminated LTI-TK prepolymer with the other components of the composite individually by quantifying the disappearance of the isocyanate peak (around 2270 $cm^{-1}$). The isocyanate peaks were calibrated to a standard curve of known NCO concentrations to find an initial rate constant for each reaction during the first 6 minutes. These rate constants along with the initial concentrations of each component were input into a Matlab program to calculate the number of isocyanate and hydroxyl equivalents versus time assuming second-order chemical kinetics. Isocyanate and hydroxyl conversion versus time were determined from the calculated numbers of equivalents.

The working time for the MG composites was defined using a rheometer with 25-mm plates. A gap size of 1.5 mm and constant strain (1%) and frequency (1 Hz) were applied to the composite and the working time defined by the time of the G'-G" crossover point. This time was compared to the tack-free time which was defined as when the material no longer stuck to a metal spatula.

Compressive Mechanical Properties

Samples for compressive studies were prepared by injecting composites into 6 mm diameter tubes and compressing under a 0.96 kg weight to ensure cohesion throughout initial cure. Samples were cut to a height equal to 2 times their diameter (12 mm) using a Buehler IsoMet Low Speed Saw (Lake Bluff, Ill.). Modulus and strength were measured at various time points over a 2-week period to determine when the composites were completely crosslinked. Specimens were preloaded to 12 N and compressed at a rate of 25 mm $min^{-1}$ using an MTS 858 Bionix Servohydraulic Test System (Eden Prairie, Minn.). The engineering stress was calculated by dividing the load by the platen-contacting surface area and the engineering strain determined by dividing the displacement by initial sample height. The slope of the linear-elastic portion of the resulting stress-strain curve was identified as the compressive modulus and the maximum stress as the compressive strength. When a maximum stress could not be identified, the stress at 10% strain was reported.

Degradation

The degradation characteristics of PTKUR were assessed in hydrolytic and oxidative conditions. An accelerated degradation medium comprising 20 wt % hydrogen peroxide in 0.1 M cobalt chloride in DI water simulated the environment produced by reactive oxygen species at the implant site. PTKUR films (17 mg) were immersed in 350 µL (1 mL/50 mg initial sample) degradation media and placed on a shaker table at 37° C. PTKUR degradation was compared to lysine-derived poly(caprolactone urethane) (PCLUR), which was expected to undergo minimal hydrolytic degradation. Oxidative media was changed every 72 hours when time points exceeded 3 days to ensure the presence of oxidizing radicals. Samples were washed 3× with 100 mL DI water, dried under vacuum for at least 48 hours, and weighed at various time points to determine the degradation rate. Samples were gold sputter-coated for 45 seconds and imaged using SEM to visualize the change in architecture with degradation Rheology Viscosity was characterized using a TA Instruments AR 2000ex rheometer fitted with 25-mm parallel plates at 25° C. For the starting materials (TK diol and LTI-TK prepolymer), a small sample was injected between the plates which were subsequently depressed to a gap size of 500 µm. A frequency sweep was applied at a constant strain in the linear viscoelastic region (0.2 for the TK diol and 0.5 for the quasi prepolymer). A Cox-Merz transformation related the dynamic data to viscosity as a function of shear rate. The rheological properties of uncatalyzed (non-reactive) composites were found using a gap size of 1.5 mm. A constant strain of 1% was applied to the composite through a frequency sweep and a Cox-Merz transformation applied to characterize injectability.

In Vitro Characterization

The surface chemistry of PTKUR polymer films was observed by water contact angle using a Ramé-Hart Goniometer (Mountain Lakes, N.J.) to predict cellular behavior at the material interface. Cellular attachment was verified using SEM and proliferation was observed using a BCA Protein Assay kit. MC3T3 cells were seeded ($2 \times 10^4$ cells/mL) onto thin sections of MG and nHA composites that were conditioned in complete αMEM medium with 10% FBS and 1% P/S overnight. Samples were submerged in 5% glutaraldehyde followed by 2% osmium tetroxide and an ethanol dehydration ladder to fix for SEM after 24 hours incubation. To measure proliferation, samples were taken from culture at 1, 4, and 7 days. Samples were transferred to a new well, washed with PBS, and the cells trypsinized. Cell pellets were lysed using RIPA buffer to extract the cellular protein. The BCA kit was used to quantify total protein at each time point.

Implantation of PTKUR/Ceramic Composite Cements in Rabbits

PTKUR/ceramic composites were evaluated in cylindrical femoral condyle plug defects in eight New Zealand White rabbits weighing 4-5 kg. All surgical and care procedures were carried out at IBEX Preclinical Research, Inc. (Logan, Utah) under aseptic conditions per the approved IACUC protocol. The reactive components (TK diol, FeAA catalyst, LTI-TK prepolymer, MasterGraft, and nHA) were gamma-irradiated using a dose of approximately 25 kGY prior to use. After administration of anesthesia, bilateral defects 6-8 mm deep×5 mm diameter were drilled in the femoral condyle of the distal femurs of 8 rabbits. PTKUR/ceramic composites incorporating either MG or nHA (n=3) were mixed on site, injected into the defect, and allowed to cure for 10 minutes prior to closing the wound. Animals were euthanized and femurs harvested at 6 and 12 weeks to evaluate healing and polymer degradation. Micro-computed tomography (Scanco µCT 50) was performed with a voxel size of 17.2 µm and a threshold of 237 (386 mg $HA/cm^3$) to match the intensity of the native trabecular bone surrounding the defect. Histology preparation was performed by Histion. Calcified samples were embedded in PMMA and sections taken from the center of the defect area; the sections were stained with Stevenel's Blue or hematoxylin and eosin (H&E) to identify new bone formation and cellular activity at the defect site.

Statistical Analysis

Anova with post hoc comparisons using Tukey's multiple comparisons test was applied to compression testing data to compare statistical differences with cure time. The Holm-Sidak multiple comparison test was used to evaluate significance in total protein over time for each composite individually, and the plot shows standard error of the mean (SEM). All other data was plotted with standard deviation, and $p<0.05$ was considered statistically significant.

Results and Discussion

When combined with ceramic micro- or nanoparticles, PTKUR cements exhibited working times comparable to calcium phosphate cements and strengths exceeding those of trabecular bone. PTKUR/ceramic composite cements supported appositional bone growth and integrated with host bone near the bone-cement interface at 6 and 12 weeks post-implantation in rabbit femoral condyle plug defects. Histological evidence of osteoclast-mediated resorption of the cements was observed at 6 and 12 weeks. These findings demonstrate that a PTKUR bone cement with bone-like strength can be selectively resorbed by cells involved in bone remodeling, and thus represent an important initial step toward the development of resorbable bone cements for weight-bearing applications.

Thioketal Diol and Quasi-prepolymer Characterization

Figure 13B:
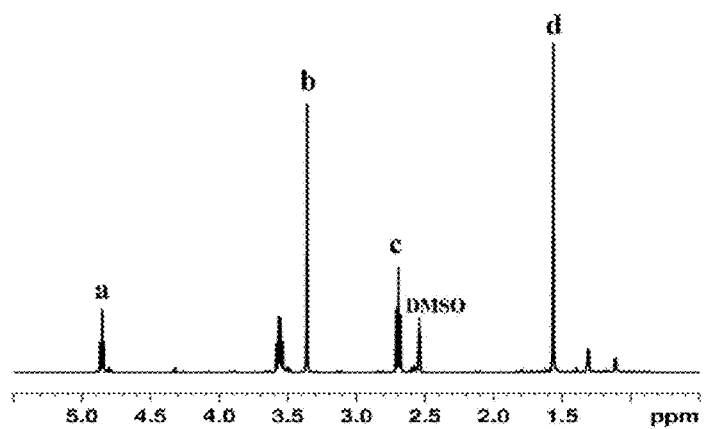
Figure 13C:
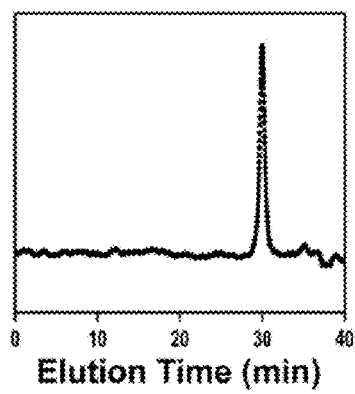
Figure 13D:
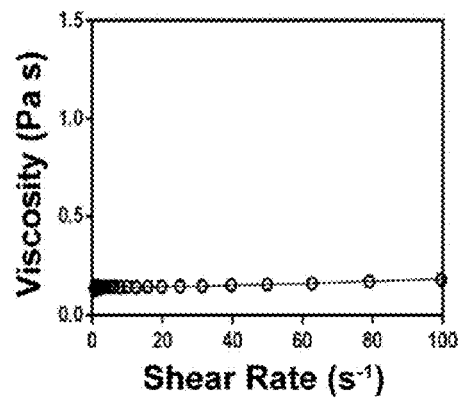

The TK diol was synthesized following the two-step reaction scheme in FIG. 13A. The characteristic NMR peak for the methyl (1.59 ppm) and hydroxyl (4.8 ppm) groups of the TK diol indicate that the targeted product was achieved (FIG. 13B), and an ATR-FTIR absorbance peak around 3400 $cm^{-1}$ confirmed hydroxyl functionalization. The OH number was found to be 574 mg KOH/g, which corresponds to a molecular weight of 196 g $mol^{-1}$ (Eq 3). GPC analysis (FIG. 13C) using a PEG standard curve showed a weight-average molecular weight of 193 g $mol^{-1}$, which is consistent with the OH number titration. These data confirm that the desired product with a theoretical molecular weight of 196.3 g $mol^{-1}$ was achieved. This low-molecular weight TK diol had a viscosity of 0.11 Pa s at a shear rate of 5 $s^{-1}$ and exhibited near Newtonian behavior at shear rates below 100 $s^{-1}$ (FIG. 13D).

Figure 14A:
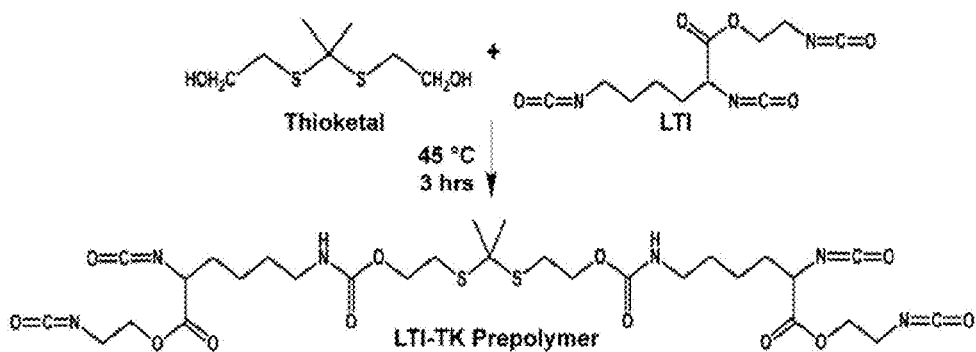
FIGS. 14A-G show synthesis of poly(thioketal urethane) (PTKUR)/ceramic composites. (A) Synthesis scheme for LTI-TK prepolymer. (B) Viscosity of the LTI-TK prepolymer is independent of shear rate. (C) Reaction of TK diol with LTI-TK prepolymer to form a crosslinked PTKUR network. (D) Fabrication of PTKUR/ceramic composites by mixing LTI-TK prepolymer, TK diol, and ceramic particles (MG or nHA). (E) The viscosity of uncatalyzed (non-reactive) LTI-TK/TK diol/ceramic mixtures decreases with increasing shear rate, providing evidence of shear-thinning behavior. (F-G) SEM images of (F) MG and (G) nHA composites show lack of porosity. Due to their relatively large size (100-300 μm), MG particles (light grey) can be distinguished from the PTKUR phase (dark grey).
Figure 14B:
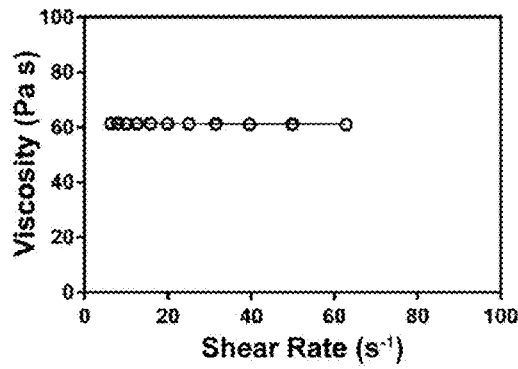

A quasi-prepolymer was synthesized to improve handling by increasing LTI viscosity, lowering the reaction exotherm, and minimizing phase separation during polymerization. TK diol was reacted with a 2.5 molar excess of LTI to form an LTI-TK prepolymer (FIG. 14A). The excess of LTI greater than 2 renders this component a quasi-prepolymer, although it will be referred to as a prepolymer in this study. The LTI-TK prepolymer exhibited Newtonian behavior, but the viscosity of 61 Pa s (measured at 5 $s^{-1}$, FIG. 14B) was considerably greater than that measured for TK diol or LTI (0.036-0.061 Pa s). The % NCO number of the prepolymer determined by titration was 25.1%, which is slightly lower than the theoretical NCO number of 26.7% based on stoichiometry.

Composite Characterization

Figure 14C:
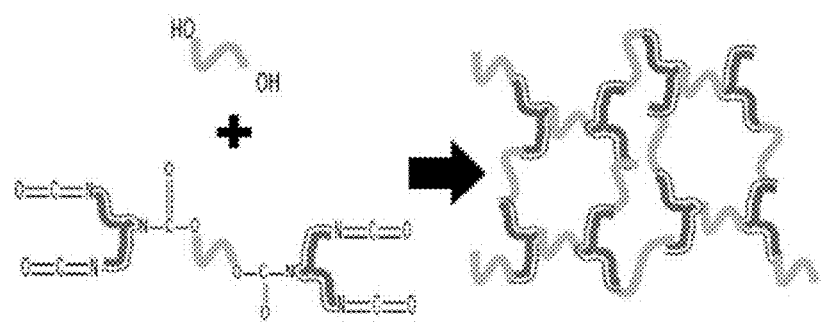
Figure 14D:
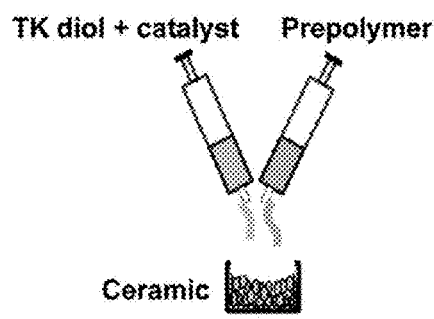
Figure 14E:
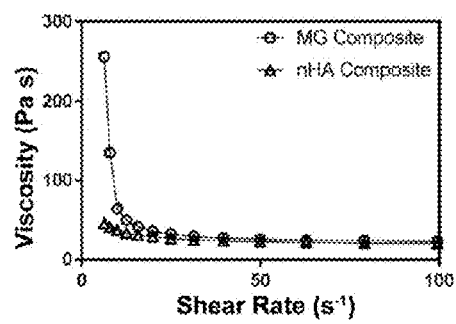
Figure 14F:
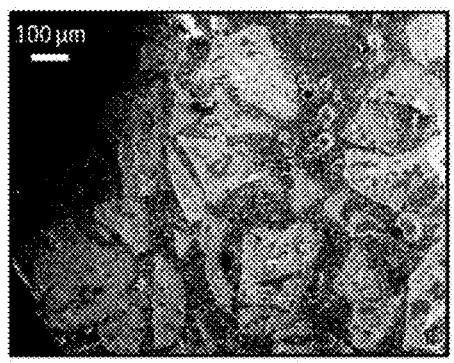
Figure 14G:
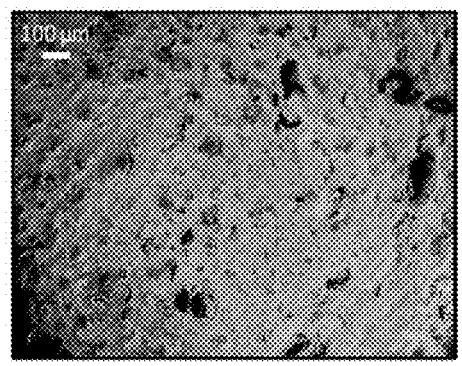

Crosslinked PTKUR composites (FIG. 14C) incorporating either MG or nHA particles were fabricated according to the schematic in FIG. 14D. FIG. 14E shows the initial (e.g., uncatalyzed) dynamic viscosities of both MG and nHA composites up to shear rates of 100 $s^{-1}$. Both materials exhibit shear thinning behavior that is more prominent at lower shear rates, which enhances injectability, and have viscosities of 20-25 Pa s at a shear rate of 100 $s^{-1}$. SEM images of the composites showed minimal porosity was achieved using a low-toxicity, iron-based gelling catalyst (25:1 gel:blow, FIG. 14 F-G) compared to previously investigated amine-based catalysts with high blowing power (1:20 gel:blow).

PTKUR films were made by mixing TK and LTI-TK prepolymer with iron catalyst without incorporating ceramic particles. The polymer film exhibited a contact angle of 70.2° indicating a moderately hydrophobic surface. Films of indices 110, 125, and 140 all swelled less than 3.5% after soaking in water for 2 weeks and the differences between them were not significant. Since there was no difference in swelling and the swelling was less than 5% for all samples, all of the indices were considered suitable for use in vivo. An index of 140 was chosen for the studies in this work to ensure complete crosslinking and a more rigid composite as reported previously.

The reactivity of the polymer was investigated using ATR-FTIR. The second-order rate constant ($k_i$, Eq (5)) of each component was calculated based on the initial isocyanate concentration ($C_0$) and the disappearance of the isocyanate peak (C).

$$\frac{1}{C} = k_i t + \frac{1}{C_0} \quad (5)$$

Figure 15A:
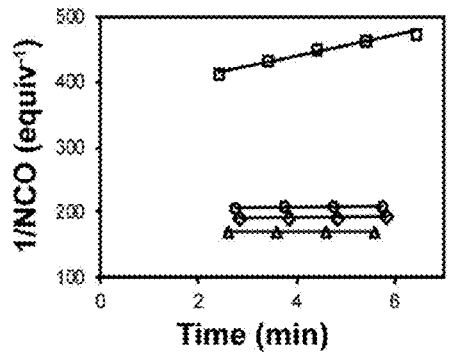
FIGS. 15A-B show kinetics of the setting reaction. (A) The reaction rate constant (k) of a second order reaction is calculated from the slope of the line of 1/[NCO] with time. The rate constant of the LTI-TK prepolymer-TK diol reaction (□) is substantially greater than that measured for MG (Δ), nHA (○), or water (◇). (B) Using the rate constant for the dominant reaction TK diol+LTI-TK prepolymer, the conversion of the NCO and OH functional groups was calculated versus time.

The catalyst was reduced by half (compared to the in vivo studies) for the reactivity experiments to slow the reaction, which was necessary to investigate the reaction mechanisms. FIG. 15A shows the calculation of the initial rate constant ($k_i$) for each reaction from the slope of the $2^{nd}$ order rate plot. The plot is linear for the first 6 minutes of the reaction, which confirms that the reactions are second order as anticipated. Further, the very small slope for MG, nHA, and water with LTI-TK indicates these components have very low reactivity, and thus they were not included in the conversion calculations. The relatively high rate constant for the LTI-TK/TK gelling reaction compared to the LTI-TK/water blowing reaction (25:1 gel:blow ratio) confirms the preferential gelling activity of the iron acetylacetonate (FeAA) catalyst compared to the triethylene diamine (TEDA) catalyst investigated previously (1:20 gel:blow). The concentration of LTI-TK prepolymer (I) and TK diol (D) were calculated as:

$$\frac{dC_D}{dt} = \frac{dC_I}{dt} = -k_D C_D C_I M \quad (6)$$

where $C_j$ is the concentration of each component (I or D, g equiv$^{-1}$ min$^{-1}$) M is the mass of the composite (g). The conversion of LTI-TK prepolymer and TK diol was calculated as:

$$\xi_j = \frac{C_{j0} - C_j}{C_{j0}} \quad (7)$$

Figure 15B:
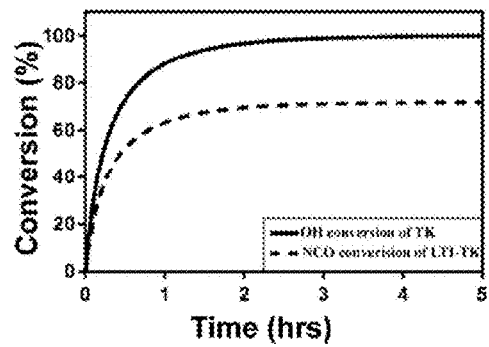

Conversion of NCO and OH groups are shown in FIG. 15B. The hydroxyl groups in the TK diol are completely converted and an excess of isocyanate functional groups remain, as anticipated from the high isocyanate index of 140. The excess isocyanate is anticipated to slowly react with the ceramic and environmental water, as reported previously for allograft bone composites, due to the substantially lower reactivity of the LTI-TK prepolymer with these components.

Figure 16A:
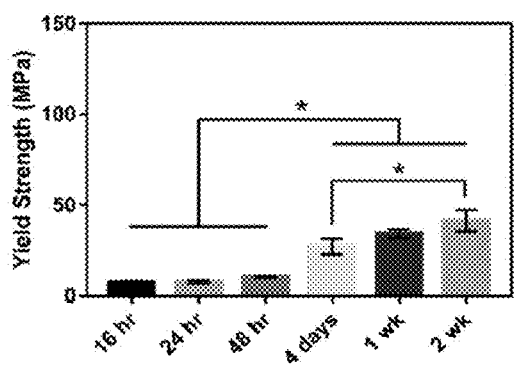
FIGS. 16A-F show mechanical properties of PTKUR/ceramic composites under static compressive loading. (A) Yield strength and (B) modulus of PTKUR/MG composites measured versus time for up to two weeks. (C) Yield strength and (D) modulus of PTKUR/nHA composites measured versus time for up to two weeks. Maximum compressive properties were achieved after 1 week cure time. The physical appearance of (E) MG and (F) nHA composites after compressive testing supports this finding.
Figure 16B:
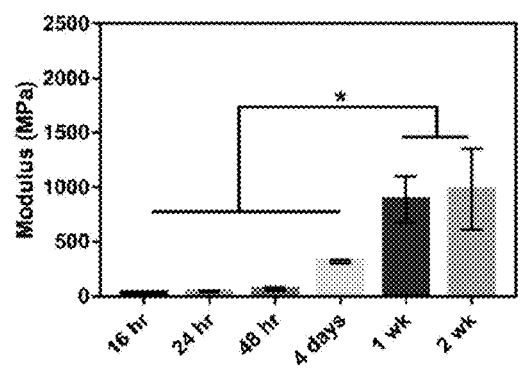
Figure 16C:
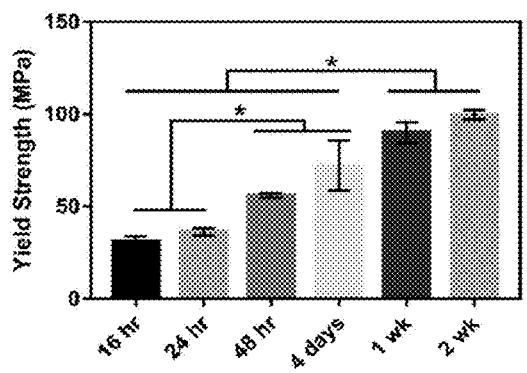
Figure 16D:
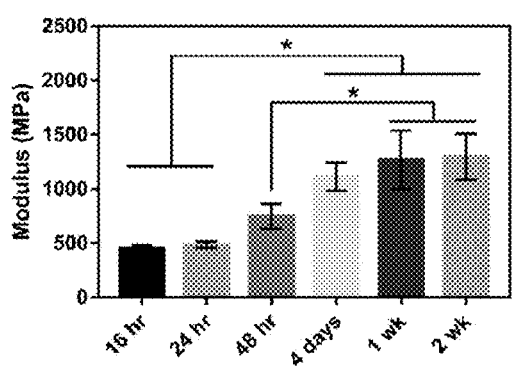
Figure 16E:
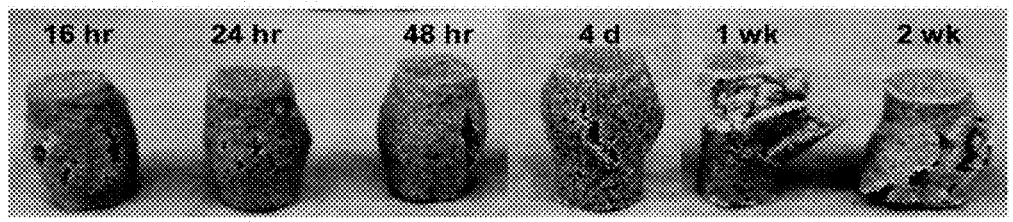
Figure 16F:
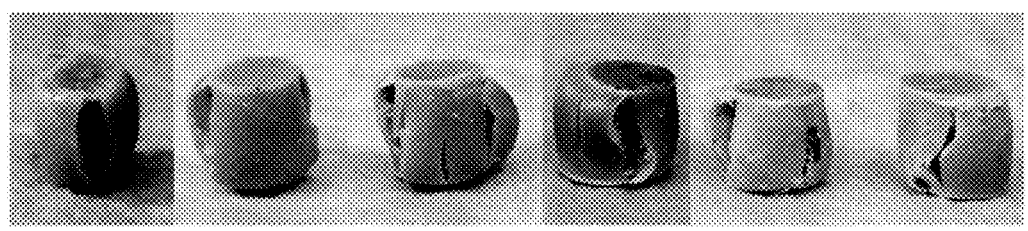

MG composites achieved a maximum compressive yield strength of 40±7 MPa and modulus of 936±46 MPa after 1 week of curing in air at RT (FIG. 16A-B). These composites had an initial strength of 7.7 MPa and modulus of 36 MPa after 16 hours curing at RT. nHA composites exhibited initial strength and moduli much greater than MG composites as expected due to the increased surface area-to-volume ratio of the mechanically robust nanoparticles. These cements had an initial compressive yield strength and modulus of 31±3 MPa and 452±35 MPa, respectively. The composites reached a yield strength of 90±6 MPa and modulus of 1267±277 MPa after 1 week (FIG. 16C-D). The mechanical properties of both composites increased over the first week, indicating that complete crosslinking was achieved 1 week after fabrication. The physical appearance of the composites post-compression supports this finding. MG composites up to 48 hours cure time experience some elastic recovery to their original shape around 30 minutes post-compression, where plastic deformation is more evident in the 1 and 2 week samples (FIG. 16E). These changes in resilience are less apparent in the stronger nHA samples (FIG. 16F). Trabecular bone is reported to have a compressive strength of 5-10 MPa and modulus of 50-400 MPa. Therefore, the initial compressive strength and modulus of MG composites are close to the properties of trabecular bone and nHA composites exceed these properties. Both composites are mechanically stronger than trabecular bone after 1 week.

Figure 17A:
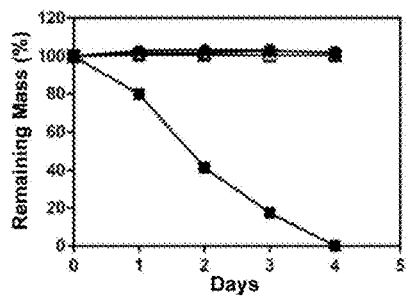
FIGS. 17A-E show degradation of PCLUR and PTKUR films. (A) PTKUR films were hydrolytically stable in PBS despite their rapid degradation in oxidative media after only 4 days. (B) After 4 months, PCLUR and PTKUR substantially degraded in oxidative medium, while no degradation was observed in PBS. (C-E) SEM images show the effects of oxidative degradation on the architecture of the PTKUR films after (C) 24 h, (D) 48 h, and (E) 72 h.
Figure 17B:
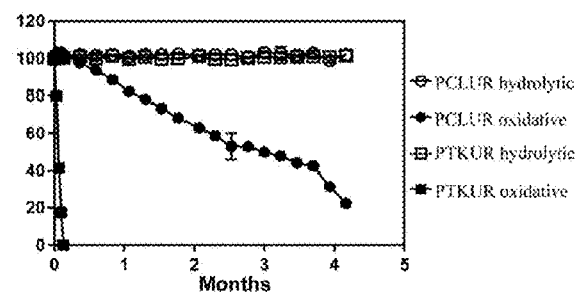
Figure 17C:
Figure 17D:
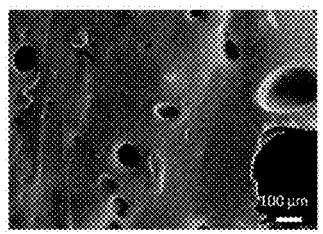
Figure 17E:
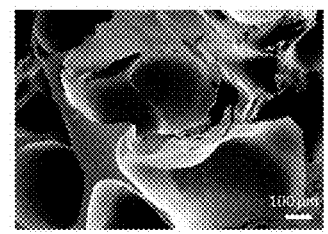

The degradation rate of PTKUR films under hydrolytic and oxidative conditions was measured in vitro. PTKUR was compared to PCLUR as this material has been shown to degrade slowly in vivo. PTKUR degraded completely after 4 days in vitro in oxidative media (FIG. 17A) but experienced minimal hydrolytic degradation in PBS after 4 months (FIG. 17B). SEM images of PTKUR after 24, 48, and 72 hours in oxidative media show morphological changes in the films in response to degradation, as evidenced by the formation of pores in the material (FIG. 17C-E). PCLUR degraded minimally in PBS as expected and did not completely degrade in oxidative media until about 5 months.

In Vitro Characterization

The osteoblast precursor MC3T3 cell line was used in all in vitro studies to assess cell attachment and proliferation. SEM images show that cells attached and spread on MG (FIG. 18A) and nHA (FIG. 18B) composites after 24 h culture. Cell proliferation on the films was assessed for up to 7 days post-seeding by measuring the change in total protein with time. FIG. 18C shows that the cell population on MG composites increased with time, but the differences were not significant. Cells proliferated on nHA composites, as evidenced by the increase in total protein from day 1 to day 7. Hydroxyapatite is the primary mineral component in bone, and therefore MC3T3 cells were expected to adhere and proliferate on scaffolds comprising 60 wt % nHA.[42] While MG contains only 15% HA, the beta-tricalcium phosphate (β-TCP) component is also an osteoconductive ceramic. The slower proliferation rate of MC3T3 cells on MG composites could potentially be explained by the relatively large size (100-300 μm) of the MG microparticles, resulting in relatively large areas of polymer that is less osteoconductive than the ceramic. In contrast, phase-separation of the nHA and polymer components was not observed in the nHA composites, suggesting that the nHA is more uniformly distributed due to its smaller particle size.

Tissue and Cellular Response in the Femoral Condyle Defect Model

Figure 20:
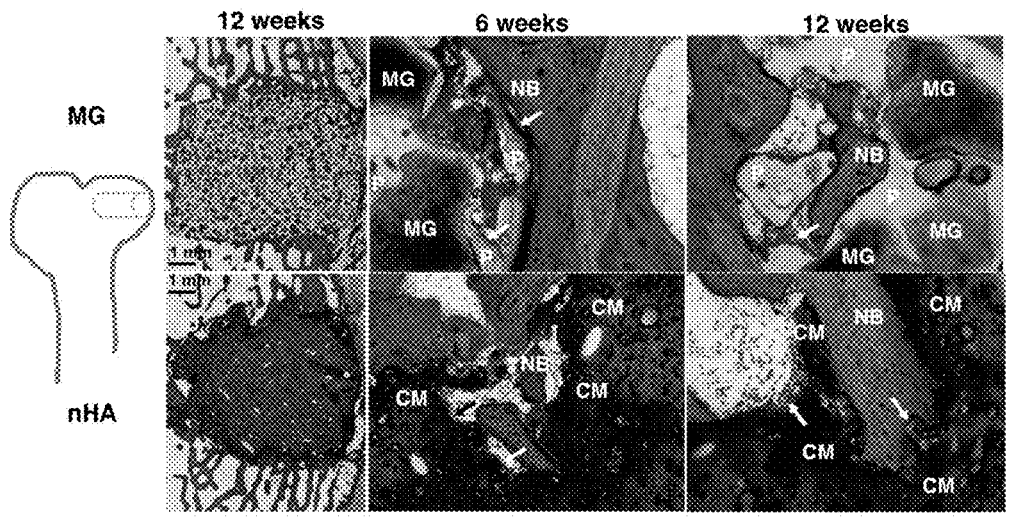
FIG. 20 shows images of transverse histological sections of PTKUR/MG and PTKUR/nHA composite cements. Low-magnification (2×) images of cements at 12 weeks show appositional growth of dense trabecular bone near the host bone-cement interface. Higher magnification (20-40×) images of PTKUR/MG cements at 6 and 12 weeks reveal evidence of residual MG (dark grey) particles, resorption of PTKUR (P, light grey), cellular infiltration (blue), osteoid (arrows), and new bone (NB, red) formation. Similar observations were made for PTKUR/nHA cements, but the nHA particles could not be distinguished due to their small size. Resorption of the cement (CM) was evident in the histological sections.

The composites were injected into femoral condyle plug defects in rabbits to assess bone healing and cement resorption. In vivo x-ray imaging immediately following the surgery indicated good placement and complete fill of the defect with the materials. μCT images of MG and nHA cements at 6 and 12 weeks are shown in FIG. 19. Trabecular densification was evident at the periphery of the defects, indicating that the material was integrated with the host bone and initiating a healing response. Low-magnification (2×) images of histological sections stained with Stevenel's Blue stain show appositional growth of dense trabecular bone near the host bone-cement interface at 12 weeks (FIG. 20). The materials were well-tolerated by the host tissue and no adverse reactions were evident. Higher magnification (20-40×) images show remodeling and integration of the cements with host bone near the surface of the cements at 6 and 12 weeks. Due to the relatively large size of MG particles (100-300 μm), the PKTUR (P) and MG particles (MG) could be distinguished in the histological sections. PTKUR resorption near the interface was observed, resulting in cellular infiltration and new bone (NB, red) formation. Osteoid (arrows) was observed near the surface of the residual PTKUR. While the nHA particles were too small to distinguish in the histological sections, similar phenomena were observed for nHA cements. Resorption of the cement (CM) near the host bone interface resulted in new bone formation and osteoid was evident near the surface of the cement.

Figure 21:
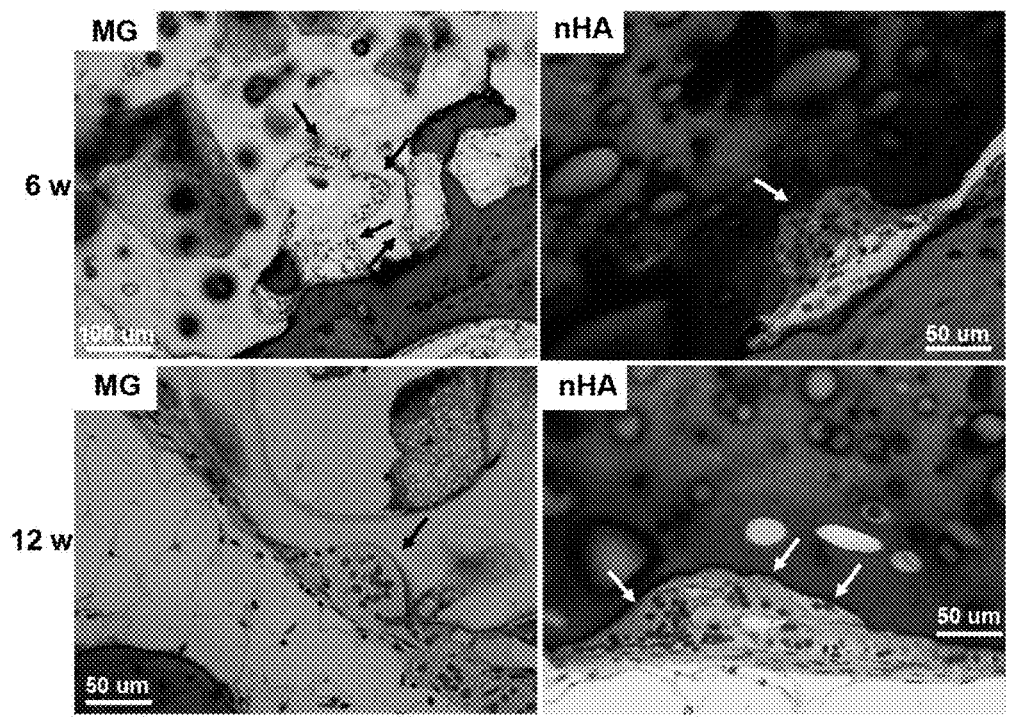
FIG. 21 shows resorption of PTKUR/MG and PTKUR/nHA cements mediated by osteoclast-like cells at 6 and 12 weeks. Osteoclasts are identified as large (>50 μm) multinucleated (nucleus stains dark blue) cells near the host bone-cement interface.

Resorption appeared to be cell-mediated, as indicated by the irregular morphology of the cement (black arrows, FIG. 21) and the presence of osteoclast-like cells, identified as large (>50 μm) multi-nucleated (nuclei stained dark blue, FIG. 21) cells, near the bone-cement interface. In contrast, negligible degradation was observed in the interior of the cement. These findings are consistent with the notion that resorption of the cements was surface-mediated by osteoclasts and/or macrophages through an ROS mechanism (FIG. 17) as the instant inventors have reported previously for PTKUR scaffolds implanted in cutaneous wounds. Due to the low (<10%) porosity of the cements, the rate of cellular infiltration and remodeling was slow. Increasing the porosity would be anticipated to accelerate infiltration of cells and consequent new bone formation.

Materials

Thioglycolic acid, 2,2-dimethoxypropane, bismuth chloride, lithium aluminum hydride, ϑ-caprolactone, nanocrystalline hydroxyapatite (nHA, <200 nm), and anhydrous solvents were purchased from Sigma-Aldrich (St. Louis, Mo.). The ϑ-caprolactone was treated with magnesium sulfate, and nHA was dried under vacuum at 80° C. for at least 24 hours prior to use. Acros Organics iron (III) acetylacetonate (FeAA) was purchased from Fisher Scientific and used as received. Lysine triisocyanate (LTI) was purchased from Jinan Haohua Industry Co., LTD (Jinan, China) and carbon-treated in methyl-tert-butyl ether 3 times for 24 hours at 70° C. to remove impurities. MasterGraft (MG) particles supplied by Medtronic (Memphis, Tenn.) were ground to 100-300 μm diameter particles using a mortar and pestle and filtered between 100 and 300 μm sieves. The resulting microparticles were washed in 95% acetone, triple rinsed with water, and dried under vacuum.

MC3T3 cells were supplied by ATCC (Manassas, Va.). Gibco™ α-MEM medium, penicillin/streptomycin (P/S) and a Pierce™ bicinchoninic (BCA) Protein Assay kit were purchased from Thermo Scientific™ (Waltham, Mass.). Sterile phosphate buffered saline (PBS) and 0.25% trypsin were purchased from Corning Cellgro (Manassas, Va.) and fetal bovine serum (FBS) from HyClone (Pittsburgh, Pa.). Reagents for cell fixation including glutaraldehyde and osmium tetroxide were purchased from Fisher Scientific and Sigma Aldrich, respectively.

Throughout this application, various publications are referenced. All such references, including the follow listed references, are incorporated herein by reference.

REFERENCES

1. Whang K, Thomas C H, Healy K E, Nuber G. A novel method to fabricate bioabsorbable scaffolds. *Polymer.* 1995; 36:837-842
2. Ishaug-Riley S L, Crane-Kruger G M, Yaszemski M J, Mikos A G. Three-dimensional culture of rat calvarial osteoblasts in porous biodegradable polymers. *Biomaterials.* 1998; 19:1405-1412
3. Pitt C G. Poly-e-caprolactone and its copolymers. In: Chasin M, Langer R S, eds. *Biodegradable polymers as drug delivery systems.* New York: Marcel Dekker, Inc.; 1990:71-120.
4. Ciapetti G, Ambrosio L, Savarino L, Granchi D, Cenni E, Baldini N, Pagani S, Guizzardi S, Causa F, Giunti A. Osteoblast growth and function in porous poly ϑ-caprolactone matrices for bone repair: A preliminary study. *Biomaterials.* 2003; 24:3815-3824
5. Lowry K J, Hamson K R, Bear L, Peng Y B, Calaluce R, Evans M L, Anglen J O, Allen W C. Polycaprolactone/glass bioabsorbable implant in a rabbit humerus fracture model. *Journal of Biomedical Materials Research.* 1997; 36:536-541
6. Leong K W, Simonte V, Langer R S. Synthesis of polyanhydrides: Melt-polycondensation, dehydrochlorination, and dehydrative coupling. *Macromolecules.* 1987; 20:705-712
7. Ibim S E M, Uhrich K E, Attawia M, Shastri V R, El-Amin S F, Bronson R, Langer R, Laurencin C T. Preliminary in vivo report on the osteocompatibility of poly(anhydride-co-imides) evaluated in a tibial model. *Journal of Biomedical Materials Research.* 1998; 43:374-379
8. Nilsson A, Liljensten E, Bergstrom C, Sollerman C. Results from a degradable tmc joint spacer (artelon) compared with tendon arthroplasty. *The Journal of Hand Surgery.* 2005; 30:380-389
9. Gogolewski S, Gorna K, Turner A S. Regeneration of bicortical defects in the iliac crest of estrogen-deficient sheep, using new biodegradable polyurethane bone graft substitutes. *Journal of Biomedical Materials Research Part A.* 2006; 77A:802-810

10. Lü J-M, Wang X, Marin-Muller C, Wang H, Lin P H, Yao Q, Chen C. Current advances in research and clinical applications of plga-based nanotechnology. *Expert Review of Molecular Diagnostics.* 2009; 9:325-341
11. Bezwada R S, Jamiolkowski D D, Lee I-Y, Agarwal V, Persivale J, Trenka-Benthin S, Erneta M, Suryadevara J, Yang A, Liu S. Monocryl® suture, a new ultra-pliable absorbable monofilament suture. *Biomaterials.* 1995; 16:1141-1148
12. Dang W, Daviau T, Brem H. Morphological characterization of polyanhydride biodegradable implant Gliadel® during in vitro and in vivo erosion using scanning electron microscopy. *Pharm Res.* 1996; 13:683-691
13. Chen J, Xu J, Wang A, Zheng M. Scaffolds for tendon and ligament repair: Review of the efficacy of commercial products. *Expert Review of Medical Devices.* 2009; 6:61-73
14. Hafeman A E, Li B, Yoshii T, Zienkiewicz K, Davidson J M, Guelcher S A. Injectable biodegradable polyurethane scaffolds with release of platelet-derived growth factor for tissue repair and regeneration. *Pharm Res.* 2008; 25:2387-2399
15. Ignatius A A, Claes L E. In vitro biocompatibility of bioresorbable polymers: Poly(l, dl-lactide) and poly(l-lactide-co-glycolide). *Biomaterials.* 1996; 17:831-839
16. Hua N, Sun J. Body distribution of poly(d,l-lactide-co-glycolide) copolymer degradation products in rats. *J Mater Sci: Mater Med.* 2008; 19:3243-3248
17. Visscher G E, Robison R L, Maulding H V, Fong J W, Pearson J E, Argentieri G J. Biodegradation of and tissue reaction to 50:50 poly(dl-lactide-co-glycolide) microcapsules. *Journal of Biomedical Materials Research.* 1985; 19:349-365
18. Guelcher S A. Biodegradable polyurethanes: Synthesis and applications in regenerative medicine. *Tissue Engineering: Part B.* 2008; 14:3-17
19. Guelcher S A, Srinivasan A, Dumas J E, Didier J E, McBride S, Hollinger J O. Synthesis, mechanical properties, biocompatibility, and biodegradation of polyurethane networks from lysine polyisocyanates. *Biomaterials.* 2008; 29:1762-1775
20. Guelcher S A, Srinivasan A, Hafeman A, Gallagher K M, Doctor J S, Khetan S, McBride S, Hollinger J O. Synthesis, in vitro degradation, and mechanical properties of two-component poly(ester urethane)urea scaffolds: Effects of water and polyol composition *Tissue Engineering.* 2007; 13:2321-2333
21. Dumas J E, BrownBaer P B, Prieto E M, Guda T, Hale R G, Wenke J C, Guelcher S A. Injectable reactive biocomposites for bone healing in critical-size rabbit calvarial defects. *Biomedical Materials.* 2012; 7:024112
22. Fu K, Pack D W, Klibanov A M, Langer R. Visual evidence of acidic environment within degrading poly (lactic-co-glycolic acid) (plga) microspheres. *Pharm Res.* 2000; 17:100-106
23. Lu L, Peter S J, D. Lyman M, Lai H-L, Leite S M, Tamada J A, Uyama S, Vacanti J P, Langer R S, Mikos A G. In vitro and in vivo degradation of porous poly(dl-lactic-co-glycolic acid) foams. *Biomaterials.* 2000; 21:1837-1845
24. Antheunis H, van der Meer J-C, de Geus M, Heise A, Koning C E. Autocatalytic equation describing the change in molecular weight during hydrolytic degradation of aliphatic polyesters. *Biomacromolecules.* 2010; 11:1118-1124
25. Athanasiou K A, Niederauer G G, Agrawal C M. Sterilization, toxicity, biocompatibility and clinical applications of polylactic acid/polyglycolic acid copolymers. *Biomaterials.* 1996; 17:93-102
26. An Y H, Woolf S K, Friedman R J. Pre-clinical in vivo evaluation of orthopaedic bioabsorbable devices. *Biomaterials.* 2000; 21:2635-2652
27. Dumas J E, Prieto E M, Zienkiewicz K J, Guda T, Wenke J C, Bible J E, Holt G E, Guelcher S A. Balancing the rates of new bone formation and polymer degradation enhances healing of weight-bearing allograft/polyurethane composites in rabbit femoral defects. *Tissue Engineering Part A.* 2013
28. Renouf-Glauser A C, Rose J, Farrar D F, Cameron R E. Comparison of the hydrolytic degradation and deformation properties of a plla-lauric acid based family of biomaterials. *Biomacromolecules.* 2006; 7:612-617
29. Hakkarainen M, Höglund A, Odelius K, Albertsson A-C. Tuning the release rate of acidic degradation products through macromolecular design of caprolactone-based copolymers. *Journal of the American Chemical Society.* 2007; 129:6308-6312
30. Harris T J, von Maltzahn G, Lord M E, Park J-H, Agrawal A, Min D-H, Sailor M J, Bhatia S N. Protease-triggered unveiling of bioactive nanoparticles. *Small.* 2008; 4:1307-1312
31. Li H, Yu S S, Miteva M, Nelson C E, Werfel T, Giorgio T D, Duvall C L. Matrix metalloproteinase responsive, proximity-activated polymeric nanoparticles for sirna delivery. *Advanced Functional Materials.* 2013; 23:3040-3052
32. West J L, Hubbell J A. Polymeric biomaterials with degradation sites for proteases involved in cell migration. *Macromolecules.* 1998; 32:241-244
33. Kim S, Healy K E. Synthesis and characterization of injectable poly(n-isopropylacrylamide-co-acrylic acid) hydrogels with proteolytically degradable cross-links. *Biomacromolecules.* 2003; 4:1214-1223
34. Lutolf M P, Weber F E, Schmoekel H G, Schense J C, Kohler T, Muller R, Hubbell J A. Repair of bone defects using synthetic mimetics of collagenous extracellular matrices. *Nat Biotech.* 2003; 21:513-518
35. Skarja G A, Woodhouse K A. In vitro degradation and erosion of degradable, segmented polyurethanes containing an amino acid-based chain extender. *Journal of Biomaterials Science, Polymer Edition.* 2001; 12:851-873
36. Guan J, Wagner W R. Synthesis, characterization and cytocompatibility of polyurethaneurea elastomers with designed elastase sensitivity. *Biomacromolecules.* 2005; 6:2833-2842
37. Patterson J, Hubbell J A. Enhanced proteolytic degradation of molecularly engineered peg hydrogels in response to mmp-1 and mmp-2. *Biomaterials.* 2010; 31:7836-7845
38. Thayer A M. Improving peptides. *Chemical & Engineering News.* 2011; 89:13-20
39. Hensley K, Robinson K A, Gabbita S P, Salsman S, Floyd R A. Reactive oxygen species, cell signaling, and cell injury. *Free Radical Biology and Medicine.* 2000; 28:1456-1462
40. auf dem Keller U, Kumin A, Braun S, Werner S. Reactive oxygen species and their detoxification in healing skin wounds. *J Investig Dermatol Symp P.* 2006; 11:106-111
41. Pacher P, Beckman J S, Liaudet L. Nitric oxide and peroxynitrite in health and disease. *Physiological Reviews.* 2007; 87:315-424

42. Napoli A, Valentini M, Tirelli N, Muller M, Hubbell J A. Oxidation-responsive polymeric vesicles. *Nat Mater.* 2004; 3:183-189
43. Wilson D S, Dalmasso G, Wang L, Sitaraman S V, Merlin D, Murthy N. Orally delivered thioketal nanoparticles loaded with tnf-α-sirna target inflammation and inhibit gene expression in the intestines. *Nat Mater.* 2010; 9:923-928
44. de Gracia Lux C, Joshi-Barr S, Nguyen T, Mahmoud E, Schopf E, Fomina N, Almutairi A. Biocompatible polymeric nanoparticles degrade and release cargo in response to biologically relevant levels of hydrogen peroxide. *Journal of the American Chemical Society.* 2012; 134:15758-15764
45. Gupta M K, Meyer T A, Nelson C E, Duvall C L. Poly(ps-b-dma) micelles for reactive oxygen species triggered drug release. *Journal of Controlled Release.* 2012; 162:591-598
46. Han P, Ma N, Ren H, Xu H, Li Z, Wang Z, Zhang X. Oxidation-responsive micelles based on a selenium-containing polymeric superamphiphile. *Langmuir.* 2010; 26:14414-14418
47. Shim M S, Xia Y. A reactive oxygen species (ros)-responsive polymer for safe, efficient, and targeted gene delivery in cancer cells. *Angewandte Chemie International Edition.* 2013; 52:6926-6929
48. Yu S S, Koblin R L, Zachman A L, Perrien D S, Hofmeister L H, Giorgio T D, Sung H-J. Physiologically relevant oxidative degradation of oligo(proline) cross-linked polymeric scaffolds. *Biomacromolecules.* 2011; 12:4357-4366
49. Hafeman A E, Zienkiewicz K J, Carney E, Litzner B, Stratton C, Wenke J C, Guelcher S A. Local delivery of tobramycin from injectable biodegradable polyurethane scaffolds. *Journal of Biomaterials Science, Polymer Edition.* 2010; 21:95-112
50. Hafeman A E, Zienkiewicz K J, Zachman A L, Sung H-J, Nanney L B, Davidson J M, Guelcher S A. Characterization of the degradation mechanisms of lysine-derived aliphatic poly(ester urethane) scaffolds. *Biomaterials.* 2011; 32:419-429
51. Adolph E J, Hafeman A E, Davidson J M, Nanney L B, Guelcher S A. Injectable polyurethane composite scaffolds delay wound contraction and support cellular infiltration and remodeling in rat excisional wounds. *Journal of Biomaterials Research Part A.* 2012; 100A:450-461
52. Page J M, Prieto E M, Dumas J E, Zienkiewicz K J, Wenke J C, Brown-Baer P, Guelcher S A. Biocompatibility and chemical reaction kinetics of injectable, settable polyurethane/allograft bone biocomposites. *Acta Biomaterialia.* 2012; 8:4405-4416
53. Guelcher S A, Patel V, Gallagher K M, Connoly S, Didier J E, Doctor J S, Hollinger J O. Synthesis and in vitro biocompatibility of injectable polyurethane foam scaffolds. *Tissue Engineering.* 2006; 12:1247-1259
54. Hu Y, Grainger D W, Winn S R, Hollinger J O. Fabrication of poly(α-hydroxy acid) foam scaffolds using multiple solvent systems. *Journal of Biomedical Materials Research.* 2002; 59:563-572
55. Karageorgiou V, Kaplan D. Porosity of 3d biomaterial scaffolds and osteogenesis. *Biomaterials.* 2005; 26:5474-5491
56. Mikos A G, Temenoff J S. Formation of highly porous biodegradable scaffolds for tissue engineering. *Electronic Journal of Biotechnology.* 2000; 3:114-119
57. Pike J K, Ho T, Wynne K J. Water-induced surface rearrangements of poly(dimethylsiloxane-urea-urethane) segmented block copolymers. *Chemistry of Materials.* 1996; 8:856-860
58. Harbers G M, Grainger D W. Cell-material interactions: Fundamental design issues for tissue engineering and clinical considerations. In: Guelcher S A, Hollinger J O, eds. *An introduction to biomaterials.* CRC Press, Taylor & Francie Group; 2006.
59. Arima Y, Iwata H. Effect of wettability and surface functional groups on protein adsorption and cell adhesion using well-defined mixed self-assembled monolayers. *Biomaterials.* 2007; 28:3074-3082
60. Schubert M A, Wiggins M J, Anderson J M, Hiltner A. Role of oxygen in biodegradation of poly(etherurethane urea) elastomers. *Journal of Biomedical Materials Research.* 1997; 34:519-530
61. Eglin D, Griffon S, Alini M. Thiol-containing degradable poly(thiourethane-urethane)s for tissue engineering. *Journal of Biomaterials Science, Polymer Edition.* 2010; 21:477-491
62. Laschke M W, Strohe A, Scheuer C, Eglin D, Verrier S, Alini M, Pohlemann T, Menger M D. In vivo biocompatibility and vascularization of biodegradable porous polyurethane scaffolds for tissue engineering. *Acta Biomaterialia.* 2009; 5:1991-2001
63. Aste-Amezaga M, Ma X, Sartori A, Trinchieri G. Molecular mechanisms of the induction of il-12 and its inhibition by il-10. *The Journal of Immunology.* 1998; 160:5936-5944
64. Jayakumar A, Widenmaier R, Ma X, McDowell M A. Transcriptional inhibition of interleukin-12 promoter activity in *leishmania* spp.-infected macrophages. *Journal of Parasitology.* 2008; 94:84-93
65. Gogolewski S, Gorna K. Biodegradable polyurethane cancellous bone graft substitutes in the treatment of iliac crest defects. *Journal of Biomedical Materials Research Part A.* 2007; 80A:94-101
66. Salvatore R N, Smith R A, Nischwitz A K, Gavin T. A mild and highly convenient chemoselective alkylation of thiols using cs2co3-tbai. *Tetrahedron Letters.* 2005; 46:8931-8935.
67. ASTM-International. E1899-08. Standard test method for hydroxyl groups using reaction with p-toluenesulfonyl isocyanate (tsi) and potentiometric titration with tetrabutylammonium hydroxide. 2008.
68. Kober M, Wesslén B. Surface properties of a segmented polyurethane containing amphiphilic polymers as additives. *Journal of Applied Polymer Science.* 1994; 54:793-803
69. ASTM-International. D695-10. Standard test method for compressive properties of rigid plastics. 2010
70. Christenson E M, Anderson J M, Hiltner A. Oxidative mechanisms of poly(carbonate urethane) and poly(ether urethane) biodegradation: In vivo and in vitro correlations. *Journal of Biomedical Materials Research Part A.* 2004; 70A:245-255
71. Schubert M A, Wiggins M J, Schaefer M P, Hiltner A, Anderson J M. Oxidative biodegradation mechanisms of biaxially strained poly(etherurethane urea) elastomers. *Journal of Biomedical Materials Research.* 1995; 29:337-347
72. Zhao Q H, McNally A K, Rubin K R, Renier M, Wu Y, Rose-Caprara V, Anderson J M, Hiltner A, Urbanski P, Stokes K. Human plasma α2-macroglobulin promotes in vitro oxidative stress cracking of pellethane 2363-80a: In vivo and in vitro correlations. *Journal of Biomedical Materials Research.* 1993; 27:379-388
73. Zhao Q, Casas-Bejar J, Urbanski P, Stokes K. Glass wool-h2o2/cocl2 test system for in vitro evaluation of biodegradative stress cracking in polyurethane elastomers. *Journal of Biomedical Materials Research.* 1995; 29:467-475.
74. K.-D. Kühn, *Bone cements: up-to-date comparison of physical and chemical properties of commercial materials*, Springer 2000.
75. M. Bohner, *Eur Cell Mater,* 2010, 20, 3-10.
76. A. J. Wagoner Johnson and B. A. Herschler, *Acta Biomaterialia,* 2011, 7, 16-30.
77. R. Adhikari, P. A. Gunatillake, I. Griffiths, L. Tatai, M. Wickramaratna, S. Houshyar, T. Moore, R. T. Mayadunne, J. Field, M. McGee and T. Carbon, *Biomaterials,* 2008, 29, 3762-3770.
78. J. E. Dumas, T. Davis, G. E. Holt, T. Yoshii, D. S. Perrien, J. S. Nyman, T. Boyce and S. A. Guelcher, *Acta Biomaterialia,* 2010, 6, 2394-2406.
79. I. C. Bonzani, R. Adhikari, S. Houshyar, R. Mayadunne, P. Gunatillake and M. M. Stevens, *Biomaterials,* 2007, 28, 423-433.
80. J. E. Dumas, K. Zienkiewicz, S. A. Tanner, E. M. Prieto, S. Bhattacharyya and S. A. Guelcher, *Tissue Engineering Part A,* 2010, 16, 2505-2518.
81. J. M. Page, E. M. Prieto, J. E. Dumas, K. J. Zienkiewicz, J. C. Wenke, P. Brown-Baer and S. A. Guelcher, *Acta biomaterialia,* 2012, 8, 4405-4416.
82. J. E. Dumas, E. M. Prieto, K. J. Zienkiewicz, T. Guda, J. C. Wenke, J. Bible, G. E. Holt and S. A. Guelcher, *Tissue Engineering Part A,* 2014, 20, 115-129.
83. A. E. Hafeman, K. J. Zienkiewicz, A. L. Zachman, H.-J. Sung, L. B. Nanney, J. M. Davidson and S. A. Guelcher, *Biomaterials,* 2011, 32, 419-429.
84. P. P. de Bruyn and W. T. Kabisch, *American Journal of Anatomy,* 1955, 96, 375-417.
85. J. E. Dumas, P. B. BrownBaer, E. M. Prieto, T. Guda, R. G. Hale, J. C. Wenke and S. A. Guelcher, *Biomedical Materials,* 2012, 7, 024112.
86. E. M. Prieto, A. D. Talley, N. R. Gould, K. J. Zienkiewicz, S. J. Drapeau, K. N. Kalpakci and S. A. Guelcher, *Journal of biomedical materials research. Part B, Applied biomaterials,* 2015, DOI: 10.1002/jbm.b.33349.
87. F. Loi, L. A. Córdova, J. Pajarinen, T.-h. Lin, Z. Yao and S. B. Goodman, *Bone,* 2016, 86, 119-130.
88. K. Schmidt-Bleek, B. J. Kwee, D. J. Mooney and G. N. Duda, *Tissue Engineering Part B: Reviews,* 2015, 21, 354-364.
89. S. Nukavarapu, J. Freeman and C. Laurencin, *Regenerative Engineering of Musculoskeletal Tissues and Interfaces*, Woodhead Publishing, 2015.
90. S. A. Sheweita, K. I. Khoshhal and H. H. Baghdadi, in *Systems Biology of Free Radicals and Antioxidants*, Springer, 2014, pp. 2973-2995.
91. I. Garrett, B. Boyce, R. Oreffo, L. Bonewald, J. Poser and G. Mundy, *Journal of Clinical Investigation,* 1990, 85, 632.
92. L. L. Key, W. C. Wolf, C. M. Gundberg and W. L. Ries, *Bone,* 1994, 15, 431-436.
93. J. R. Martin, M. K. Gupta, J. M. Page, F. Yu, J. M. Davidson, S. A. Guelcher and C. L. Duvall, *Biomaterials,* 2014, 35, 3766-3776.
94. R. Z. LeGeros, *Clinical orthopaedics and related research,* 2002, 395, 81-98.
95. A. D. Talley, M. A. P. Mcenery, K. N. Kalpakci, K. J. Zienkiewicz, D. A. Shimko and S. A. Guelcher, *Journal of Biomedical Materials Research Part B: Applied Biomaterials,* 2016, in press.
96. A. International, *Journal,* 2016, E1899-16.
97. S. A. Guelcher, A. Srinivasan, J. E. Dumas, J. E. Didier, S. McBride and J. O. Hollinger, *Biomaterials,* 2008, 29, 1762-1775.
98. A. International, *Journal,* 2010.
99. R. Guo, C. L. Ward, J. M. Davidson, C. L. Duvall, J. C. Wenke and S. A. Guelcher, *Biomaterials,* 2015, 54, 21-33.
100. A. J. Harmata, S. Uppuganti, M. Granke, S. A. Guelcher and J. S. Nyman, *Journal of the mechanical behavior of biomedical materials,* 2015, 51, 345-355.
101. A. International, *Journal,* 2016.
102. M. A. Schubert, M. J. Wiggins, J. M. Anderson and A. Hiltner, *Journal of Biomedical Materials Research,* 1997, 34, 519-530.
103. E. M. Christenson, J. M. Anderson and A. Hiltner, *Journal of Biomedical Materials Research Part A,* 2004, 70A, 245-255.
104. R. Guo, S. Lu, J. M. Page, A. R. Merkel, S. Basu, J. A. Sterling and S. A. Guelcher, *Advanced healthcare materials,* 2015, 4, 1826-1832.
105. Dow polyurethanes—prepolymer definition, http://dowac.custhelp.com/app/answers/detail/a_id/5082/~/dow-polyurethanes---prepolymer-definition, (accessed May 23, 2016, 2016).
106. S. A. Guelcher, V. Patel, K. M. Gallagher, S. Connolly, J. E. Didier, J. S. Doctor and J. O. Hollinger, *Tissue Engineering,* 2006, 12, 1247-1259.
107. A. J. Harmata, C. L. Ward, K. J. Zienkiewicz, J. C. Wenke and S. A. Guelcher, *Journal of Materials Research,* 2014, 29, 2398-2407.
108. S. Parnell, K. Min and M. Cakmak, *Polymer,* 2003, 44, 5137-5144.
109. K. Ashida, *Polyurethane and related foams: chemistry and technology*, CRC press, 2006.
110. H.-Y. Mi, X. Jing, M. R. Salick, T. M. Cordie, X.-F. Peng and L.-S. Turng, *Journal of Materials Science,* 2014, 49, 2324-2337.
111. K. Rezwan, Q. Chen, J. Blaker and A. R. Boccaccini, *Biomaterials,* 2006, 27, 3413-3431.
112. S. Fernando, M. McEnery and S. Guelcher, *Advances in Polyurethane Biomaterials,* 2016, 481.
113. V. Karageorgiou and D. Kaplan, *Biomaterials,* 2005, 26, 5474-5491.
114. D. S. Muggli, A. K. Burkoth and K. S. Anseth, *Journal of biomedical materials research,* 1999, 46, 271-278.
115. J. Buckwalter, M. Glimcher, R. Cooper and R. Recker, *J Bone Joint Surg Am,* 1995, 77, 1256-1275.
116. R. D. A. Gaasbeek, H. G. Toonen, R. J. van Heerwaarden and P. Buma, *Biomaterials,* 2005, 26, 6713-6719.
117. P. V. Giannoudis, H. Dinopoulos and E. Tsiridis, *Injury,* 2005, 36, S20-S27.

What is claimed is:
1. A thioketal of formula I:

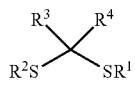

wherein $R^1$ and $R^2$ are independently selected from the group consisting of $CH_2C(O)OH$ and $CH_2CH_2OH$;

wherein $R^3$ is selected from the group consisting of $CH_3$ and $CH_2CH_2CH_2CH_3$;

wherein $R^4$ is selected from the group consisting of $CH_3$, $SCH_2C(O)OH$, and $SCH_2CH_2OH$; and wherein when $R^3$ and $R^4$ are both $CH_3$ at least one of $R^1$ and $R^2$ is $CH_2CH_2OH$.

2. The thioketal of claim 1, wherein $R^1$ and $R^2$ are both $CH_2CH_2OH$.

3. The thioketal of claim 2, wherein $R^4$ is $CH_3$.

4. The thioketal of claim 2, wherein $R^4$ is $SCH_2CH_2OH$.

5. The thioketal of claim 1, wherein $R^1$ and $R^2$ are both $CH_2C(O)OH$.

6. The thioketal of claim 5, wherein $R^4$ is $SCH_2C(O)OH$.

7. The thioketal of claim 1, wherein the low molecular weight thioketal comprises an equivalent weight of at least 95 grams/equivalent.

8. The thioketal of claim 1, wherein the low molecular weight thioketal comprises an equivalent weight of about 100 grams/equivalent.

9. A biodegradable scaffold, comprising:
the thioketal of claim 1; and
an isocyanate, where the thioketal is linked to the isocyanate to form the scaffold.

10. The scaffold of claim 9, wherein the scaffold further comprises a catalyst.

11. The scaffold of claim 10, wherein the catalyst comprises an amine.

12. The scaffold of claim 11, wherein the catalyst is a solution of triethylene diamine in dipropyleneglycol.

13. The scaffold of claim 9, further comprising a ceramic selected from the group consisting of β-tricalcium phosphate (β-TCP), hydroxyapatite, and combinations thereof.

14. The scaffold of claim 9, wherein the isocyanate comprises lysine triisocyanate (LTI).

15. The scaffHold of claim 9, wherein the thioketal provides a crosslinker that is selectively degraded by reactive oxygen species (ROS) to permit cell-mediated degradation of the scaffold.

16. The scaffold of claim 12, wherein the solution of triethylamine diamine in dipropyleneglycol comprises 33% triethylenediamine in 67% dipropyleneglycol.

17. A method of forming a biodegradable scaffold, the method comprising:
blending the thioketal of claim 1 with an isocyanate, forming a prepolymer;
mixing the thioketal, the prepolymer, and a ceramic; and then
adding a catalyst to form the biodegradable scaffold;
wherein the thioketal is a low-molecular weight thioketal having at least two hydroxyl terminal groups.

* * * * *